US010000570B2

(12) United States Patent
Labrijn et al.

(10) Patent No.: US 10,000,570 B2
(45) Date of Patent: Jun. 19, 2018

(54) ANTIBODY VARIANTS HAVING MODIFICATIONS IN THE CONSTANT REGION

(71) Applicant: Genmab A/S, Copenhagen V (DK)

(72) Inventors: Aran Frank Labrijn, Amsterdam (NL); Stefan Loverix, Ternat (BE); Paul Parren, Odijk (NL); Jan Van De Winkel, Zeist (NL); Janine Schuurman, Diemen (NL); Ignace Lasters, Antwerp (BE)

(73) Assignee: Genmab A/S, Copenhagen V (DK)

( * ) Notice: Subject to any disclaimer, the term of this patent is extended or adjusted under 35 U.S.C. 154(b) by 0 days. days.

(21) Appl. No.: 14/739,768

(22) Filed: Jun. 15, 2015

(65) Prior Publication Data
US 2015/0376282 A1 Dec. 31, 2015

Related U.S. Application Data

(62) Division of application No. 13/132,423, filed as application No. PCT/EP2009/066290 on Dec. 3, 2009, now Pat. No. 9,085,625.

(30) Foreign Application Priority Data
Dec. 3, 2008 (DK) .................................. 200801709

(51) Int. Cl.
C07K 16/28 (2006.01)
C07K 16/00 (2006.01)
A61K 39/395 (2006.01)
A61K 47/48 (2006.01)
A61K 51/10 (2006.01)
A61K 39/00 (2006.01)

(52) U.S. Cl.
CPC ...... *C07K 16/2863* (2013.01); *A61K 39/3955* (2013.01); *A61K 47/48561* (2013.01); *A61K 51/103* (2013.01); *C07K 16/00* (2013.01); *A61K 2039/505* (2013.01); *C07K 2317/21* (2013.01); *C07K 2317/52* (2013.01); *C07K 2317/524* (2013.01); *C07K 2317/526* (2013.01); *C07K 2317/53* (2013.01); *C07K 2317/76* (2013.01)

(58) Field of Classification Search
CPC .................. C07K 2317/52; C07K 2317/53
See application file for complete search history.

(56) References Cited

U.S. PATENT DOCUMENTS

| 2010/0306867 A1* | 12/2010 | Schuurman | ............ C07K 16/00 800/18 |
| 2010/0325744 A1* | 12/2010 | Schuurman | ............ C07K 16/00 800/13 |
| 2011/0293607 A1* | 12/2011 | Labrijn | ................... C07K 16/00 424/133.1 |
| 2011/0300156 A1* | 12/2011 | Verploegen | ............ C07K 16/36 424/158.1 |
| 2012/0020952 A1* | 1/2012 | Parren | .................... C07K 16/00 424/130.1 |
| 2015/0368345 A1* | 12/2015 | Labrijn | .................. C07K 16/00 530/387.3 |
| 2016/0053020 A1* | 2/2016 | Verploegen | ............ C07K 16/36 424/172.1 |

FOREIGN PATENT DOCUMENTS

| EP | 1 810 979 A1 | 7/2007 |
| WO | WO 97/13852 | 4/1997 |
| WO | WO 00/05266 | 2/2000 |
| WO | WO 2005/063816 A2 | 7/2005 |
| WO | WO 2007/059782 A1 | 5/2007 |
| WO | WO 2007/068255 A1 | 6/2007 |
| WO | WO 2008/119353 A1 | 10/2008 |
| WO | WO 2008/145140 A2 | 12/2008 |
| WO | WO 2008/145142 A1 | 12/2008 |

OTHER PUBLICATIONS

Labrijn et al.Current Opinion in Immunology 2008, 20:479-485.*
Rosati et al.mAbs 5:6, 917-924; Nov./Dec. 2013.*
Rose et al.Structure 19, 1274-1282, Sep. 7, 2011.*
Ibragimova and Eade (Biophysical Journal, Oct. 1999, vol. 77, pp. 2191-2198).
Burgess et al, Journal of Cell Biology vol. 111 Nov. 1990 2129-2138.
Lazar et al Molecular and Cellular Biology Mar. 1988 vol. 8 No. 3 1247-1252.
Schwartz et al, Proc Natl Acad Sci USA vol. 84:6408-6411 (1987).
Lin et al Biochemistry USA vol. 14:1559-1563 (1975).
Salfeld (Nature Biotech. 25(12): 1369-1372 (2007).
Dall'Acqua (J. Immunol. 177:1129-1138 (2006).
International Search Report from counterpart International Application No. PCT/EP2009/066290, dated Jun. 16, 2010.
Written Opinion of the International Preliminary Examining Authority from counterpart International Application No. PCT/EP2009/066290, dated Jun. 16, 2010.
Angal, S., et al., "A single amino acid substitution abolishes the heterogeneity of chimeric mouse/human (IgG4) antibody", *Molecular Immunology*, 30(1): 105-108 (Jan. 1, 1993).
Kolfschoten, M., et al., "Anti-Inflammatory Activity of Human IgG4 Antibodies by Dynamic Fab Arm Exchange," *Science*, 317: 1554-1557 (Sep. 14, 2007).
Labrijn, A. F., et al., "When binding is enough: nonactivating antibody formats," *Current Opinion in Immunology*, 20(4): 479-485 (Aug. 1, 2008).
Sheridan, C., "Pharma consolidates its grip on post-antibody landscape," *Nature Biotechnology*, 25(4): 365-366 (Apr. 2007).

(Continued)

*Primary Examiner* — Lynn A Bristol
(74) *Attorney, Agent, or Firm* — Finnegan, Henderson, Farabow, Garrett & Dunner, LLP

(57) ABSTRACT

The present invention relates to positions in the constant region of antibodies, in particular the CH3 region of IgG4, which affect the strength of CH3-CH3 interactions. Mutations that either stabilize or destabilize this interaction are disclosed.

17 Claims, 17 Drawing Sheets

(56) References Cited

OTHER PUBLICATIONS

Strohl, William R., "Optimization of Fc-mediated effector functions of monoclonal antibodies," *Current Opinion in Biotechnology*, 20(6): 685-691 (Dec. 1, 2009).

Lu, Y., et al., "The Effect of a Point Mutation on the Stability of IgG4 as Monitored by Analytical Ultracentrifugation", *Journal of Pharmaceutical Sciences*, 97(2): 960-969 (Feb. 2008).

Deng, L., et al., "Detection and quantification of the human IgG4 half-molecule, HL, from unpurified cell-culture supernatants", *Biotechnol. Appl. Biochem.*, 40: 261-269 (2004).

Gallango, M., et al., "An Unusual Case of Waldenström Macroglobulinemia with Half Molecules of IgG in Serum and Urine", *Blut*, 48: 91-97 (1983).

Gregory, L., et al., "The Solution Conformations of the Subclasses of Human IgG Deduced from Sedimentation and Small Angle X-Ray Scattering Studies", *Molecular Immunology*, 24(8): 821-829 (1987).

Hobbs, J.R., "Immunocytoma o' Mice an' Men", *British Medical Journal*, pp. 67-72 (Apr. 10, 1971).

Hobbs, J.R., et al., "A Half-Molecule GK Plasmacytoma", *Clin. ex. Immunol.*, 5: 199-207 (1969).

Horgan, C., et al., "Studies on Antigen Binding by Intact and Hinge-Deleted Chimeric Anitbodies", *The Journal of Immunology*, 150(12): 5400-5407 (Jun. 15, 1993).

Junghans, R. P., et al., "The protection receptor for IgG catabolism is the $\beta_2$-microglobulin—containing neonatal intestinal transport receptor," *Proc. Natl. Acad. Sci.*, 93: 5512-5516 (May 1996).

Mushinski, J.F.,"γA A Half Molecules: Defective Heavy Chain Mutants in Mouse Myeloma Proteins", *The Journal of Immunology*, 106(1): 41-50 (Jan. 1971).

Mushinski, J.F., et al., "IgA Half Molecules II. Genetic Variants of IgA Detected in Normal Mouse Intestinal Contents", *The Journal of Immunology*, 117(5): 1668-1675 (Nov. 1976).

Parham, P., "On the Fragmentation of Monoclonal IgG1, IgG2a, and IgG2b From BALB/c Mice", *The Journal of Immunology*, 131(6): 2895-2902 (Dec. 1983).

Potter, M., et al., Disorders in the Differentiation of Protein Secretion in Neoplastic Plasma Cells, *J Mol. Biol.*, 9: 537-544 (1964).

Robinson, E. A., et al., "Chemical Characterization of a Mouse Immunoglobin A Heavy Chain with a 100-Residue Deletion", *The Journal of Biological Chemistry*, 249(20): 6605-6610 (1974).

Schuurman, J., et al., "The inter-heavy chain disulfide bonds of IgG4 are in equilibrium with intra-chain disulfide bonds", *Molecular Immunology*, 38: 1-8 (2001).

Seligmann, M. et al., "Immunochemical Study of a Human Myeloma IgG1 Half Molecule", *Ann. Immunol.*, 129C: 855-870 (1978).

Spiegelberg, H.L., "Human Myeloma IgG Half-Molecules Catabolism and Biological Properties", *The Journal of Clinical Investigation*, 56: 588-594 (1975).

Spiegelberg, H.L., et al., "Human Myeloma IgG Half-Molecules. Structural and Antigenic Analyses", *Biochemistry*, 14(10): 2157-2163 (1975).

Spiegelberg, H.L., et al., "IgG Half-Molecules: Clinical and Immunologic Features in a Patient With Plasma Cell Leukemia", *Blood*, 45(3): 305-313 (Mar. 1975).

Zack, D. J., et al., Somatically Generated Mouse Myeloma Variants Synthesizing IgA Half-Molecules, *J Exp. Med.*, 154: 1554-1569 (Nov. 1981).

Dall'Acqua W. et al., "A Mutational Analysis of Binding Interactions in an Antigen-Antibody Protein-Protein Complex," *Biochemistry*, 1998, vol. 37, pp. 7981-7991.

Deisenhofer J., "Crystallographic Refinement and Atomic Models of a Human Fc Fragment and ItsComplex with Fragment B of Protein a from *Staphylococcus aureus* at 2.9- and 2.8-A Resolution," *Biochemistry*, 1981, vol. 20, No. 9, pp. 2361-2370.

Idusogie E. et al., Mapping of the C1q Binding Site on Rituxan, a Chimeric Antibody with a Human IgG1 Fc, "*The Journal of Immunology*," 2000, vol. 164, pp. 4178-4184.

Labrijn A. et al., "Therapeutic IgG4 antibodies engage in Fab-arm exchange with endogenous human IgG4 in vivo", *Nature Biotechnology*, Aug. 2009, vol. 27, No. 8, pp. 767-773.

Labrijn A. et al., "Species-Specific Determinants in the IgG CH3 Domain Enable Fab-Arm Exchange by Affecting the Noncovalent CH3—CH3 Interaction Strength", *The Journal of Immunology*, 2011, vol. 187, pp. 3238-3246.

Rose R. et al., "Quantitative Analysis of the Interaction Strength and Dynamics of Human IgG4 Half Molecules by Native Mass Spectrometry," *Structure*, 2011, vol. 19, pp. 1274-1282.

\* cited by examiner

FIG. 15

SEQUENCE LISTING

<160> NUMBER OF SEQ ID NOS: 11

<210> SEQ ID NO 1
<211> LENGTH: 1588
<212> TYPE: DNA
<213> ORGANISM: Homo sapiens

```
<400> SEQUENCE: 1
gctagcacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttggtgag     300
aggccagcac agggagggag ggtgtctgct ggaagccagg ctcagccctc ctgcctggac     360 gcacccggc tgtgcagccc cagcccaggc agcaaggca tgccccatct gtctcctcac     420
ccggaggcct ctgaccaccc cactcatgct cagggagagg gtcttctgga ttttccacc     480 aggctccggg cagccacagg ctggatgccc ctacccagg ccctgcgcat acaggggcag     540
gtgctgcgct cagacctgcc aagagccata tccggagga ccctgcccct gacctaagcc     600
caccccaaag gccaaactct ccactccctc agctcagaca ccttctctcc tcccagatct     660
gagtaactcc caatcttctc tctgcagagt ccaaatatgg tccccatgc ccatcatgcc      720 caggtaagcc aacccaggcc tcgccctcca gctcaaggcg gacaggtgc cctagagtag      780 cctgcatcca gggacaggcc ccagccgggt gctgacgcat ccacctccat ctcttcctca     840
gcacctgagt tcctggggg accatcagtc ttcctgttcc ccccaaaacc caaggacact     900
ctcatgatct cccggacccc tgaggtcacg tgcgtggtgg tggacgtgag ccaggaagac     960
cccgaggtcc agttcaactg gtacgtggat ggcgtggagg tgcataatgc caagacaaag    1020 ccgcgggag agcagttcaa cagcacgtac cgtgtggtca gcgtcctcac cgtcctgcac    1080
caggactggc tgaacggcaa ggagtacaag tgcaaggtct ccaacaaagg cctcccgtcc    1140
tccatcgaga aaaccatctc caaagccaaa gtgggacccc acggggtgcg agggccacat    1200
ggacagaggt cagctcggcc caccctctgc cctgggagtg accgctgtgc caacctctgt    1260
ccctacaggg cagccccgag agccacaggt gtacaccctg cccccatccc aggaggagat    1320
gaccaagaac caggtcagcc tgacctgcct ggtcaaaggc ttctaccca gcgacatcgc    1380 cgtggagtgg gagagcaatg gcagccgga gaacaactac aagaccacgc tcccgtgct    1440 ggactccgac ggctccttct cctctacag caggctaacc gtggacaaga gcaggtggca    1500
ggaggggaat gtcttctcat gctccgtgat gcatgaggct ctgcacaacc actacacaca    1560
gaagagcctc tccctgtctc tgggtaaa                                       1588

<210> SEQ ID NO 2
<211> LENGTH: 327
<212> TYPE: PRT
<213> ORGANISM: Homo sapiens
<220> FEATURE:
<221> NAME/KEY: VARIANT
<222> LOCATION: (189)..(189)
<223> OTHER INFORMATION: Xaa = Leu or Val
<220> FEATURE:
<221> NAME/KEY: VARIANT
<222> LOCATION: (289)..(289)
<223> OTHER INFORMATION: Xaa = Arg or Lys

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
                35                  40                  45
Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
             100                 105                 110

Glu Phe Leu Gly Gly Pro Ser Val Phe Leu Phe Pro Pro Lys Pro Lys
         115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Xaa His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Xaa Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 3
<211> LENGTH: 1588
<212> TYPE: DNA
<213> ORGANISM: Homo sapiens

<400> SEQUENCE: 3
gctagcacca agggcccatc cgtcttcccc ctggcgccct gctccaggag cacctccgag    60
agcacagccg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacgaagacc   240
tacacctgca acgtagatca caagcccagc aacaccaagg tggacaagag agttggtgag   300
aggccagcac agggagggag ggtgtctgct ggaagccagg ctcagccctc ctgcctggac   360
gcaccccggc tgtgcagccc cagcccaggg cagcaaggca tgccccatct gtctcctcac   420
ccggaggcct ctgaccaccc cactcatgct cagggagagg gtcttctgga ttttccacc   480
```

```
aggctccggg cagccacagg ctggatgccc ctaccccagg ccctgcgcat acaggggcag      540
gtgctgcgct cagacctgcc aagagccata tccggggagga ccctgcccct gacctaagcc     600
```
(correcting) 
```
aggctccggg cagccacagg ctggatgccc ctaccccagg ccctgcgcat acaggggcag      540
gtgctgcgct cagacctgcc aagagccata tccggggaga ccctgcccct gacctaagcc     600
caccccaaag gccaaactct ccactccctc agctcagaca ccttctctcc tcccagatct      660
gagtaactcc caatcttctc tctgcagagt ccaaatatgg tccccatgc ccaccatgcc      720 cgggtaagcc aacccaggcc tcgccctcca gctcaaggcg ggacaggtgc cctagagtag      780
cctgcatcca gggacaggcc ccagccgggt gctgacgcat ccacctccat ctcttcctca      840
gcacctgagt tcctgggggg accatcagtc ttcctgttcc ccccaaaacc caaggacact      900
ctcatgatct cccggacccc tgaggtcacg tgcgtggtgg tggacgtgag ccaggaagac      960
cccgaggtcc agttcaactg gtacgtggat ggcgtggagg tgcataatgc caagacaaag     1020
ccgcggggag agcagttcaa cagcacgtac cgtgtggtca gcgtcctcac cgtcctgcac     1080
caggactggc tgaacggcaa ggagtacaag tgcaaggtct ccaacaaagg cctcccgtcc     1140
tccatcgaga aaaccatctc caaagccaaa ggtgggaccc acggggtgcg agggccacat     1200
ggacagaggt cagctcggcc caccctctgc cctgggagtg accgctgtgc caacctctgt     1260
ccctacaggg cagccccgag agccacaggt gtacaccctg cccccatccc aggaggagat     1320
gaccaagaac caggtcagcc tgacctgcct ggtcaaaggc ttctacccca gcgacatcgc     1380
cgtggagtgg gagagcaatg ggcagccgga gaacaactac aagaccacgc ctcccgtgct     1440
ggactccgac ggctccttct tcctctacag caggctaacc gtggacaaga gcaggtggca     1500
ggaggggaat gtcttctcat gctccgtgat gcatgaggct ctgcacaacc actacacaca     1560
gaagagcctc tccctgtctc tgggtaaa                                        1588
```

<210> SEQ ID NO 4
<211> LENGTH: 315
<212> TYPE: PRT
<213> ORGANISM: Homo sapiens

<400> SEQUENCE: 4

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Ala Pro Glu Phe Leu Gly Gly Pro Ser Val Phe Leu Phe Pro
            100                 105                 110

Pro Lys Pro Lys Asp Thr Leu Met Ile Ser Arg Thr Pro Glu Val Thr
        115                 120                 125

Cys Val Val Val Asp Val Ser Gln Glu Asp Pro Glu Val Gln Phe Asn
    130                 135                 140

Trp Tyr Val Asp Gly Val Glu Val His Asn Ala Lys Thr Lys Pro Arg
145                 150                 155                 160

Glu Glu Gln Phe Asn Ser Thr Tyr Arg Val Val Ser Val Leu Thr Val
                165                 170                 175
```

-continued

Leu His Gln Asp Trp Leu Asn Gly Lys Glu Tyr Lys Cys Lys Val Ser
            180                 185                 190

Asn Lys Gly Leu Pro Ser Ser Ile Glu Lys Thr Ile Ser Lys Ala Lys
        195                 200                 205

Gly Gln Pro Arg Glu Pro Gln Val Tyr Thr Leu Pro Pro Ser Gln Glu
210                 215                 220

Glu Met Thr Lys Asn Gln Val Ser Leu Thr Cys Leu Val Lys Gly Phe
225                 230                 235                 240

Tyr Pro Ser Asp Ile Ala Val Glu Trp Glu Ser Asn Gly Gln Pro Glu
            245                 250                 255

Asn Asn Tyr Lys Thr Thr Pro Pro Val Leu Asp Ser Asp Gly Ser Phe
            260                 265                 270

Phe Leu Tyr Ser Arg Leu Thr Val Asp Lys Ser Arg Trp Gln Glu Gly
            275                 280                 285

Asn Val Phe Ser Cys Ser Val Met His Glu Ala Leu His Asn His Tyr
            290                 295                 300

Thr Gln Lys Ser Leu Ser Leu Ser Leu Gly Lys
305                 310                 315

<210> SEQ ID NO 5
<211> LENGTH: 105
<212> TYPE: PRT
<213> ORGANISM: Homo sapiens

<400> SEQUENCE: 5

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 6
<211> LENGTH: 106
<212> TYPE: PRT
<213> ORGANISM: Homo sapiens

<400> SEQUENCE: 6

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 7
<211> LENGTH: 330
<212> TYPE: PRT
<213> ORGANISM: Homo sapiens

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

-continued

<210> SEQ ID NO 8
<211> LENGTH: 326
<212> TYPE: PRT
<213> ORGANISM: Homo sapiens

<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 9
<211> LENGTH: 377
<212> TYPE: PRT
<213> ORGANISM: Homo sapiens

<400> SEQUENCE: 9

Ala Ser Thr Lys Gly Pro Ser Val Phe Pro Leu Ala Pro Cys Ser Arg

```
  1               5                   10                  15
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
                115                 120                 125

Cys Pro Glu Pro Lys Ser Cys Asp Thr Pro Pro Cys Pro Arg Cys
            130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
                275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
                355                 360                 365

Lys Ser Leu Ser Leu Ser Pro Gly Lys
                370                 375

<210> SEQ ID NO 10
<211> LENGTH: 4
<212> TYPE: PRT
<213> ORGANISM: Homo sapiens

<400> SEQUENCE: 10
```

```
Cys Pro Pro Cys
1

<210> SEQ ID NO 11
<211> LENGTH: 4
<212> TYPE: PRT
<213> ORGANISM: Homo sapiens

<400> SEQUENCE: 11

Cys Pro Ser Cys
1
```

ANTIBODY VARIANTS HAVING MODIFICATIONS IN THE CONSTANT REGION

This application is a divisional of U.S. Application No. 13/132,423, filed Aug. 16, 2011, which is a U.S. National Stage of International Application No. PCT/EP2009/066290, filed Dec. 3, 2009, which claims priority to DK Application No. PA 2008 01709, filed Dec. 3, 2008, all of which are incorporated herein by reference in their entireties.

FIELD OF INVENTION

The present invention relates to modified antibodies that may be used in therapeutic applications. The invention also relates to methods for producing the antibodies, pharmaceutical compositions comprising the antibodies and use thereof for different therapeutic applications.

BACKGROUND OF THE INVENTION

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each light chain is comprised of a light chain variable region (abbreviated herein as VL) and a light chain constant region (abbreviated herein as CL). Each heavy chain is comprised of a heavy chain variable region (VH) and a heavy chain constant region (CH) consisting of three domain, CH1, CH2 and CH3). CH1 and CH2 of the heavy chain are separated from each other by the so-called hinge region. The hinge region normally comprises one or more cysteine residues, which may form disulphide bridges with the cysteine residues of the hinge region of the other heavy chain in the antibody molecule.

Recently, antibodies have become a major focus area for therapeutic applications, and many antibody drug products have been approved or are in the process of being approved for use as therapeutic drugs. The desired characteristics of therapeutic antibodies may vary according to the specific condition which is to be treated. For some indications, only antigen binding is required, for instance where the therapeutic effect of the antibody is to block interaction between the antigen and one or more specific molecules otherwise capable of binding to the antigen. For such indications, the use of Fab fragments, the only function of which is to bind antigen, may be preferred. For other indications, further effects may also be required, such as for instance the ability to induce complement activation and/or the ability to for instance bind Fc receptors, protect from catabolism, recruit immune cells, etc. For such use, other parts of the antibody molecule, such as the Fc region, may be required. Some full-length antibodies may exhibit agonistic effects (which may be considered to be undesirable) upon binding to the target antigen, even though the antibody works as an antagonist when used as a Fab fragment. In some instances, this effect may be attributed to "cross-linking" of the bivalent antibodies, which in turn promotes target dimerization, which may lead to activation, especially when the target is a receptor. In the case of soluble antigens, dimerization may form undesirable immune complexes.

For some indications, monovalent antibodies may thus be preferable. The presently available Fab fragments show inferior pharmacokinetics due to their small size resulting to filtration in the kidneys as well as their inability to interact with the Brambell receptor FcRn (Junghans R P et al., Proc Natl Acad Sci USA 93(11), 5512-6 (1996)), therefore being unstable in vivo and having very rapid clearance after administration.

There is thus a need for stable monovalent antibodies which can be used as therapeutics.

Dimeric, monovalent antibodies (Fab/c), wherein the Fc region comprises two Fc polypeptides, have been described (WO200563816 to Genentech and Parham P, J Immunol. 131(6), 2895-902 (1983).

Ig half-molecules, which have a dimeric configuration consisting of only one light chain and only one heavy chain, have been described as the result of rare deletions in human and murine plasmacytomas. Studies on the biochemical nature of these half-molecules showed that they consist of IgG1 molecules in which the heavy chain CH1, hinge and CH2 regions appeared normal, whereas deletions were found in the CH3 region. The mutations appeared to be located in CH3 and the hinge peptide appeared normal (Hobbs, J R et al., Clin Exp Immunol 5, 199 (1969); Hobbs, J R, Br Med J 2, 67 (1971); Spiegelberg, H L et al., Blood 45, 305 (1975); Spiegelberg, H L et al., Biochemistry 14, 2157 (1975); Seligmann M E et al., Ann Immunol (Paris) 129C 855-870 (1978); Gallango, M L et al., Blut 48, 91 (1983)). It was also showed that this human IgG1 half-molecule is rapidly catabolized (half-life in man was 4.3 days) and, in monomeric form, is unable to bind C1q or Fc receptors on human lymphocytes, monocytes or neutrophils (Spiegelberg, H L. J Clin Invest 56, 588 (1975)).

Murine IgA half-molecules which were generated by somatic mutation have also been described (Mushinski, J F, J Immunol 106, 41 (1971); Mushinski, J F et al., J Immunol 117, 1668 (1976); Potter, M et al., J Mol Biol 93, 537 (1964); Robinson, E A et al., J Biol Chem 249, 6605 (1974); Zack, D J et al., J Exp Med 154, 1554 (1981)). These molecules were shown to all contain deletions of the CH3 domain or mutations at the CH2-CH3 boundary.

WO2007059782 (Genmab) describes human monovalent antibodies comprising a light chain and a heavy chain, wherein a) said light chain comprises the amino acid sequence of the variable (VL) region of a selected antigen specific antibody and the amino acid sequence of the constant (CL) region of an Ig, and wherein, in case of an IgG1 subtype, the amino sequence of the constant (CL) region has been modified so that it does not contain any amino acids capable of participating in the formation of disulfide bonds or covalent bonds with other peptides comprising an identical amino acid sequence of the constant (CL) region of the Ig, in the presence of polyclonal human IgG or when administered to an animal or human being, and b) said heavy chain comprises the amino acid sequence of the variable (VH) region of said selected antigen specific antibody and the amino acid sequence of the constant (CH) region of human Ig, wherein the amino acid sequence of the constant (CH) region has been modified so that the hinge region and, as required by the Ig subtype, other regions of the CH region, such as the CH3 region, does not contain any amino acid residues which participate in the formation of disulphide bonds or covalent or stable non-covalent inter-heavy chain bonds with other peptides comprising an identical amino acid sequence of the constant (CN) region of the human Ig, in the presence of polyclonal human IgG or when administered to an animal or human being.

As shown in WO2007059782, these monovalent antibodies have a more favorable in vivo half-life than Fab fragments. WO2008145140 describes variants of these monovalent antibodies wherein intermolecular CH3-CH3 interactions are destabilized. The present application describes alternative and improved variants of the monovalent antibodies disclosed in WO2007059782 and WO2008145140. These variants remain monovalent even under conditions that favor intermolecular CH3-CH3 interactions.

Human IgG4 molecules exist in various molecular forms which differ by the absence or presence of inter-heavy chain disulphide bonds located in the hinge region. Thus IgG4 molecules exist in which two, one or no inter-heavy chain disulphide bonds have been formed (Schuurman, J. et al., Mol Immunol 38, 1 (2001)). Under physiological conditions, these molecular forms of IgG4 may be in equilibrium with each other. Human IgG4s exist as tetramers in solution consisting of two Ig heavy and two light chains, as common for immunoglobulin G molecules, irrespective of the absence or presence of these interchain disulphide bonds (Schuurman 2001 supra; Gregory, L. et al. Mol Immunol 24, 821 (1987)). Only upon denaturation under non-reducing conditions, the two non-covalently associated half-molecules dissociate as demonstrated by size-determination analysis such as SDS-PAGE (Schuurman, J. et al. Mol Immunol 38, 1 (2001); Deng, L. et al. Biotechnol Appl Biochem 40, 261 (2004)). It has been shown that mutation of the residues of the hinge region which are involved in inter-chain disulphide bond formation or deletion of the hinge region lead to creation of a homogeneous pool of IgG4 molecules in solution, which pool consists of tetrameric molecules consisting of two light chains and two heavy chains (Schuurman, J. et al. Mol Immunol 38, 1 (2001); Horgan, C. et al. J Immunol 150, 5400 (1993)). The IgG4 hinge-deleted and mutated antibodies also demonstrated an improved capability of antigen crosslinking when compared to native $IgG_4$ molecules (Horgan, C. (1993) supra).

It has been shown that administration of two recombinant monoclonal IgG4 antibodies having different antigen-binding specificities to a mouse leads to in vivo formation of bispecific antibodies. The phenomenon can be reproduced in vitro by incubating IgG4 antibodies with cells or under reducing conditions. It has been shown that IgG4 antibodies having different antigen-binding specificities engage in Fab arm exchange which is stochastic and in which all IgG4 molecules seem to participate. Thus, IgG4 antibodies form bispecific antibodies without concomitant formation of aggregates.

IgG4 antibodies therefore have unusual properties which are undesirable in vivo: IgG4 antibodies are unstable, dynamic, molecules which engage in Fab arm exchange. An administered therapeutic IgG4 antibody may exchange with endogenous IgG4 antibodies with undesired specificities. The random nature of this process introduces unpredictability which is highly undesirable for human immunotherapy.

In one aspect, the present invention relates to stabilized forms of IgG4 antibodies that have a reduced ability to undergo Fab-arm exchange. Stabilized forms of IgG4 have previously been described in WO2008145142 (Genmab). It has now surprisingly been found that specific alternative substitutions in human IgG4 can prevent Fab arm exchange, and thus stabilize IgG4.

In summary, the present invention relates to positions in the constant region of antibodies, in particular the CH3 region of IgG4, which affect the strength of CH3-CH3 interactions. Mutations that either stabilize or destabilize this interaction are disclosed herein.

When introduced in the monovalent antibody context described in WO2007059782, the destabilizing mutations contribute to keeping the antibodies monovalent even under conditions that favor intermolecular CH3-CH3 interactions. When introduced in the IgG4 context, the stabilizing mutations contribute to preventing undesired Fab arm exchange.

SUMMARY OF THE INVENTION

In a first main aspect, the invention relates to a monovalent antibody, which comprises
(i) a variable region of a selected antigen specific antibody or an antigen binding part of the said region, and
(ii) a CH region of an immunoglobulin or a fragment thereof comprising the CH2 and CH3 regions, wherein the CH region or fragment thereof has been modified such that the region corresponding to the hinge region and, if the immunoglobulin is not an IgG4 subtype, other regions of the CH region, such as the CH3 region, do not comprise any amino acid residues which are capable of forming disulfide bonds with an identical CH region or other covalent or stable non-covalent inter-heavy chain bonds with an identical CH region in the presence of polyclonal human IgG,
wherein the antibody is of the IgG4 type and the constant region of the heavy chain has been modified so that one or more of the following amino acid substitutions have been made relative to the sequence set forth in SEQ ID NO: 4: Tyr (Y) in position 217 has been replaced by Arg (R), Leu (L) in position 219 has been replaced by Asn (N) or Gln (Q), Glu (E) in position 225 has been replaced by Thr (T), Val (V) or Ile (I), Ser (S) in position 232 has been replaced by Arg (R) or Lys (K), Thr (T) in position 234 has been replaced by Arg (R), Lys (K) or Asn (N), Leu (L) in position 236 has been replaced by Ser (S) or Thr (T), Lys (K) in position 238 has been replaced by Arg (R), Asp (D) in position 267 has been replaced by Thr (T) or Ser (S), Phe (F) in position 273 has been replaced by Arg (R), Gln (Q), Lys (K) or Tyr (Y), Tyr (Y) in position 275 has been replaced by Gln (Q), Lys (K) or Phe (F), Arg (R) in position 277 has been replaced by Glu (E), Thr (T) in position 279 has been replaced by Asp (D), Val (V) and Asn (N),
or the antibody is of another IgG type and the constant region of the heavy chain has been modified so that one or more of the same amino-acid substitutions have been made at the positions that correspond to the before-mentioned positions for IgG4.

As explained above, mutations at the above specified positions disfavor intermolecular CH3-CH3 interactions. Thus, monovalent antibodies carrying these mutations are less likely to dimerize through non-covalent interactions. This may be an advantage for therapeutic applications wherein such dimerization is highly undesired. Furthermore, a reduced tendency of the monovalent antibodies to associate non-covalently through the CH3 regions may make pharmaceutical compositions comprising such antibodies more stable and homogenous than pharmaceutical compositions of monovalent antibodies that do not comprise the above-specified mutations.

Thus, in another aspect, the invention relates to a pharmaceutical composition comprising the monovalent antibody according to the invention as defined herein.

In a further aspect, the invention relates to a method of treating a disease or disorder as described herein, wherein said method comprises administering to a subject in need of such treatment a therapeutically effective amount of a monovalent antibody according to the invention.

In a further aspect, the invention relates to a stabilized IgG4 antibody for use as a medicament, comprising a heavy chain and a light chain, wherein said heavy chain comprises a human IgG4 constant region having the sequence set forth in SEQ ID NO:2, wherein Lys (K) in position 250 has been replaced by Gln (Q) or Glu (E) and wherein the antibody optionally comprises one or more further substitutions, deletions and/or insertions in the constant region as set forth in SEQ ID NO:2.

As explained above, and shown herein below in the Examples, the mutations at position 250 stabilize the IgG4 molecule and prevent undesired Fab arm exchange.

DESCRIPTION OF FIGURES

FIG. 15: Sequence alignment of anti-EGFr antibody 2F8 in an IgG1, IgG4 and (partial) IgG3 backbone. Amino acid numbering according to Kabat and according to the EU-index are depicted (both described in Kabat et al., Sequences of Proteins of Immunological Interest, 5th Ed. Public Health Service, National Institutes of Health, Bethesda, Md. (1991)).

DETAILED DESCRIPTION OF THE SEQUENCE LISTINGS

Figure 1:
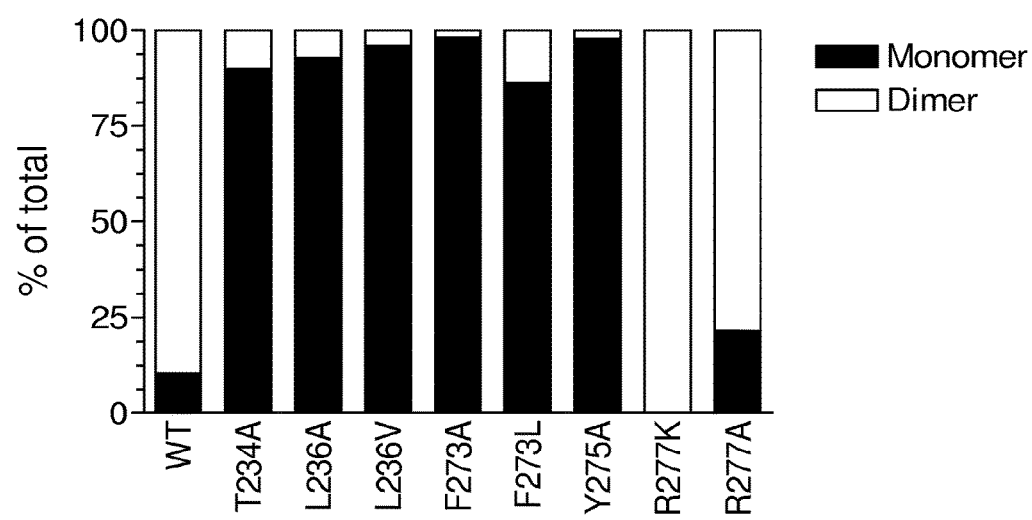
FIG. 1: Percentage of molecules present as monomers for each HG mutant tested using non-covalent nano-electrospray mass spectrometry. HG mutant samples were prepared in aqueous 50 mM ammonium acetate solutions at a concentration of 1 μM.

SEQ ID No: 1: The nucleic acid sequence of the wildtype CH region of human IgG4 SEQ ID No: 2: The amino acid sequence of the wildtype CH region of human IgG4. Sequences in italics represent the CH1 region, highlighted sequences represent the hinge region, regular sequences represent the CH2 region and underlined sequences represent the CH3 region.

SEQ ID No: 3: The nucleic acid sequence of the CH region of human IgG4 (SEQ ID No: 1) mutated in positions 714 and 722

SEQ ID No: 4: The amino acid sequence of the hingeless CH region of a human IgG4. Underlined sequences represent the CH3 region.

SEQ ID No: 5: The amino acid sequence of the lambda chain constant human (accession number S25751)

SEQ ID No: 6: The amino acid sequence of the kappa chain constant human (accession number P01834)

SEQ ID No: 7: The amino acid sequence of IgG1 constant region (accession number P01857). Sequences in italics represent the CH1 region, highlighted sequences represent the hinge region, regular sequences represent the CH2 region and underlined sequences represent the CH3 region SEQ ID No: 8: The amino acid sequence of the IgG2 constant region (accession number P01859). Sequences in italics represent the CH1 region, highlighted sequences represent the hinge region, regular sequences represent the CH2 region and underlined sequences represent the CH3 region SEQ ID No: 9: The amino acid sequence of the IgG3 constant region (accession number A23511). Sequences in italics represent the CH1 region, highlighted sequences represent the hinge region, regular sequences represent the CH2 region and underlined sequences represent the CH3 region

DETAILED DESCRIPTION OF THE INVENTION

Definitions

The term "antibody" as referred to herein includes whole antibody molecules, antigen binding fragments, monovalent antibodies, and single chains thereof. Antibody molecules belong to a family of plasma proteins called immunoglobulins, whose basic building block, the immunoglobulin fold or domain, is used in various forms in many molecules of the immune system and other biological recognition systems. Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain may also have regularly spaced intrachain disulfide bridges. Each light chain is comprised of a light chain variable region (abbreviated herein as VL) and a light chain constant region (abbreviated herein as CL). Each heavy chain is comprised of a heavy chain variable region (VH) and a heavy chain constant region (CH) consisting of three domains, CH1, CH2 and CH3, and the hinge region). The three CH domains and the hinge region have been indicated for IgG1, IgG2, IgG3 and IgG4 in SEQ ID NO: 7, 8, 9 and 2, respectively (see below) The constant domain of the light chain is aligned with the first constant domain (CH1) of the heavy chain, and the light chain variable domain is aligned with the variable domain of the heavy chain forming what is known as the "Fab fragment". CH1 and CH2 of the heavy chain are separated form each other by the so-called hinge region, which allows the Fab "arms" of the antibody molecule to swing to some degree. The hinge region normally comprises one or more cysteine residues, which are capable of forming disulphide bridges with the cysteine residues of the hinge region of the other heavy chain in the antibody molecule.

The variable regions of the heavy and light chains contain a binding domain that interacts with an antigen. The constant regions of the antibodies may mediate the binding of the immunoglobulin to host tissues or factors, including various cells of the immune system (for instance effector cells) and the first component (C1q) of the classical complement system Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), for instance IgG1, IgG2, IgG3 and IgG4; IgA1 and IgA2. The genes for the heavy chains constant domains that correspond to the different classes of immunoglobulins are called alpha (α), delta (δ), epsilon (ε), gamma (γ) and mu (μ), respectively. Immunoglobulin subclasses are encoded by different genes such as γ1, γ2, γ3 and γ4. The genes for the light chains of antibodies are assigned to one of two clearly distinct types, called kappa (κ) and lambda (λ), based on the amino sequences of their constant domain. The subunit structures and three-dimensional configurations of different classes of immunoglobulins are well known. Distinct allotypes of immunoglobulins exist within the human population such as G1m(a), G1m(x), G1m(f) and G1m(z) for IgG1 heavy chain and Km1, Km1,2 and Km3 for the kappa light chain. These allotypes differ at distinct amino acids in their region encoding the constant regions.

The term antibody also encompasses "derivatives" of antibodies, wherein one or more of the amino acid residues have been derivatised, for instance by acylation or glycosylation, without significantly affecting or altering the binding characteristics of the antibody containing the amino acid sequences.

In addition, the term antibody covers variants, e.g. variants wherein the in vivo half-life of the antibodies has been improved by modifying the salvage receptor epitope of the Ig constant domain or an Ig-like constant domain such that the molecule does not comprise an intact CH2 domain or an intact Ig Fc region, cf. U.S. Pat. No. 6,121,022 and U.S. Pat. No. 6,194,551. The in vivo half-life may be furthermore increased by making mutations in the Fc region, for instance by substituting threonine for leucine at the position corresponding to position 252 of an intact antibody molecule, threonine for serine at the position corresponding to position 254 of an intact antibody molecule, or threonine for phenylalanine at the position corresponding to position 256 of an intact antibody molecule, cf. U.S. Pat. No. 6,277,375.

Furthermore, antibodies, and particularly Fab or other fragments, may be pegylated to increase the half-life. This can be carried out by pegylation reactions known in the art, as described, for example, in Focus on Growth Factors 3, 4-10 (1992), EP 154 316 and EP 401 384.

The term "antibody half-molecule" is used herein to mean an antibody molecule as described above, but comprising no more than one light chain and no more than one heavy chain, and which exists in water solutions as a heterodimer of said single light and single heavy chain. Such antibody is by nature monovalent as only one antigen-binding portion is present.

The term "human antibody", as used herein, is intended to include antibodies having variable and constant regions derived from human germline immunoglobulin sequences. The human antibodies of the invention may include amino acid residues not encoded by human germline immunoglobulin sequences (for instance mutations introduced by random or site-specific mutagenesis in vitro or by somatic mutation in vivo). However, the term "human antibody", as used herein, is not intended to include antibodies in which CDR1 or CDR2 sequences derived from the germline of another mammalian species, such as a mouse, or the CDR3 region derived from an antibody from another species, such as mouse, have been grafted onto human framework sequences. Human monoclonal antibodies directed may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. No. 5,545,806, U.S. Pat. No. 5,569,825, U.S. Pat. No. 5,625,126, U.S. Pat. No. 5,633,425, U.S. Pat. No. 5,789,650, U.S. Pat. No. 5,877,397, U.S. Pat. No. 5,661,016, U.S. Pat. No. 5,814,318, U.S. Pat. No. 5,874,299, U.S. Pat. No. 5,770,429, U.S. Pat. No. 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo7 human heavy chain transgene (as described in U.S. Pat. No. 5,770,429).

The HCo12 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424).

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478.

Splenocytes from these transgenic mice may be used to generate hybridomas that secrete human monoclonal stabilized IgG4 antibodies according to well known techniques. Such transgenic non-human animals, non-human animals comprising an operable nucleic acid sequence coding for expression of antibody used in the invention, non-human animals stably transfected with one or more target-encoding nucleic acid sequences, and the like, are additional features of the present invention. The term "$K_D$" (M), as used herein, refers to the dissociation equilibrium constant of a particular antibody-antigen interaction.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences.

The term "monovalent antibody" means in the present context that an antibody molecule is capable of binding a single molecule of the antigen, and thus is not able of antigen crosslinking.

As used herein, "specific binding"refers to the binding of an antibody, or antigen-binding fragment thereof, to a predetermined antigen. Typically, the antibody binds with an affinity corresponding to a $K_D$ of about $10^{-7}$ M or less, such as about $10^{-8}$ M or less, such as about $10^{-8}$ M or less, about $10^{-10}$ M or less, or about $10^{-11}$M or even less, when measured for instance using sulfon plasmon resonance on BIAcore or as apparent affinities based on $IC_{50}$ values in FACS or ELISA, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antigen binding peptide, so that when the $K_D$ of the antigen binding peptide is very low (that is, the antigen binding peptide is highly specific), then the amount with which the affinity for the antigen is lower than the affinity for a non-specific antigen may be at least 10,000 fold.

The terms "transgenic, non-human animal" refers to a non-human animal having a genome comprising one or more human heavy and/or light chain transgenes or transchromosomes (either integrated or non-integrated into the animal's natural genomic DNA) and which is capable of expressing human antibodies. For example, a transgenic mouse can have a human light chain transgene and either a human heavy chain transgene or human heavy chain transchromosome, such that the mouse produces human antibodies when immunized with an antigen and/or cells expressing an antigen. The human heavy chain transgene can be integrated into the chromosomal DNA of the mouse, as is the case for transgenic, for instance HuMAb mice, such as HCo7 or HCo12 mice, or the human heavy chain transgene can be maintained extrachromosomally, as is the case for transchromosomal KM mice as described in WO 02/43478. Such transgenic and transchromosomal mice are capable of producing multiple classes and isotypes of monovalent antibodies to a given antigen (for instance IgM, IgG, IgA and/or IgE) by undergoing V-D-J recombination and isotype switching.

The term "acceptor site for N-linked glycosylation" refers to a site on a polypeptide which is susceptible of becoming glycosylated on an Asn residue. The typical consensus site for this type of glycosylation is Asn-X-Ser/Thr, wherein X can be any amino acid, except for Pro.

As explained above, the characteristic IgG structure in which two heavy-light chain heterodimers are linked is maintained by the inter-heavy chain disulphide bridges of the hinge region and the non-covalent interactions of the CH3 domains.

It has been shown in WO2007059782 that removal of the hinge region in IgG4 results in the formation of monovalent antibodies in which the linkage between the two heavy-light chain heterodimers is lost or diminished. Consequently, changes in hinge region disulphide bridges of other IgG subclasses alone or in combination with mutations in the CH3 domain interactions may result in the formation of monovalent antibodies for these other subclasses as well. It is well within the capability of the skilled artisan to use the intimate knowledge of structure of Ig subclasses, and the knowledge provided in the present invention, to select and to modify selected amino acids to prevent light chain interactions.

In a first main aspect, the invention relates to a monovalent antibody, which comprises
    a variable region of a selected antigen specific antibody or an antigen binding part of the said region, and (ii) a CH region of an immunoglobulin or a fragment thereof comprising the CH2 and CH3 regions, wherein the CH region or fragment thereof has been modified such that the region corresponding to the hinge region and, if the immunoglobulin is not an IgG4 subtype, other regions of the CH region, such as the CH3 region, do not comprise any amino acid residues which are capable of forming disulfide bonds with an identical CH region or other covalent or stable non-covalent inter-heavy chain bonds with an identical CH region in the presence of polyclonal human IgG, wherein the antibody is of the IgG4 type and the constant region of the heavy chain has been modified so that one or more of the following amino acid substitutions have been made relative the sequence set forth in SEQ ID NO: 4: Tyr (Y) in position 217 has been replaced by Arg (R), Leu (L) in position 219 has been replaced by Asn (N) or Gln (G), Glu (E) in position 225 has been replaced by Thr (T), Val (V) or Ile (I), Ser (S) in position 232 has been replaced by Arg (R) or Lys (K), Thr (T) in position 234 has been replaced by Arg (R), Lys (K) or Asn (N), Leu (L) in position 236 has been replaced by Ser (S) or Thr (T), Lys (K) in position 238 has been replaced by Arg (R), Asp (D) in position 267 has been replaced by Thr (T) or Ser (S), Phe (F) in position 273 has been replaced by Arg (R), Gln (Q), Lys (K) or Tyr (Y), Tyr (Y) in position 275 has been replaced by Gln (Q), Lys (K) or Phe (F), Arg (R) in position 277 has been replaced by Glu (E), Thr (T) in position 279 has been replaced by Asp (D), Val (V) and Asn (N), or the antibody is of another IgG type and the constant region of the heavy chain has been modified so that one or more of the same amino-acid substitutions have been made at the positions that correspond to the before-mentioned positions for IgG4. See e.g. SEQ ID NO: 7, 8 and 9 for the corresponding positions in other isotypes.

In one embodiment, the monovalent antibody comprises
(i) a variable region of a selected antigen specific antibody or an antigen binding part of the said region, and
(ii) a CH region of an immunoglobulin or a fragment thereof comprising the CH2 and CH3 regions, wherein the CH region or fragment thereof has been modified such that the region corresponding to the hinge region and, if the immunoglobulin is not an IgG4 subtype, other regions of the CH region, such as the CH3 region, do not comprise any amino acid residues which are capable of forming disulfide bonds with an identical CH region or other covalent or stable non-covalent inter-heavy chain bonds with an identical CH region in the presence of polyclonal human IgG, wherein the antibody is of the IgG4 type and the constant region of the heavy chain has been modified so that one or more of the following amino acid substitutions have been made relative the sequence set forth in SEQ ID NO: 4: Glu (E) in position 225 has been replaced by Val (V), Ser (S) in position 232 has been replaced by Arg (R), Leu (L) in position 236 has been replaced by Ser (S) or Thr (T), Asp (D) in position 267 has been replaced by Thr (T) or Ser (S), Phe (F) in position 273 has been replaced by Arg (R), Gln (Q) or Tyr (Y), Tyr (Y) in position 275 has been replaced by Gln (Q) or Lys (K).

In another embodiment, the antibody is of the IgG4 type and the constant region of the heavy chain has been modified so that one or more of the following combinations of amino acid substitutions have been made relative the sequence set forth in SEQ ID NO: 4:

Asp (D) in position 267 has been replaced by Ser (S) and Tyr (Y) in position 275 has been replaced by Gln (Q) or Lys (K), Arg (R), Asp (D) in position 267 has been replaced by Thr (T) and Tyr (Y) in position 275 has been replaced by Gln (Q) or Lys (K), Arg (R), or the antibody is of another IgG type and the constant region of the heavy chain has been modified so that the same combinations of amino-acid substitutions have been made at the positions that correspond to the before-mentioned positions for IgG4.

Typically, the variable region and the $C_H$ region of the monovalent antibody are connected to each other via peptide bonds and are produced from a single open reading frame. Without being bound to any theory, it is believed that the monovalent antibodies according to the invention are capable of binding to the FcRn. Such binding may be determined by use of methods for determining binding as it is known in the art, for instance by use of ELISA assays. The binding of a monovalent antibody of the invention to FcRn may for instance be compared to the binding of a $F(ab')_2$ fragment, which $F(ab')_2$ fragment has a VH region and a VL region, which are identical to the VH region and the VL region of the monovalent antibody of the invention, to FcRn in the same assay. In one embodiment, the binding of a monovalent antibody of the invention to FcRn is more than 10 times stronger than the binding of the $F(ab')_2$ fragment to FcRn.

In one embodiment, the antibody (further) comprises a CH1 region.

In another embodiment, the monovalent antibody consists of said variable region and said CH region.

In another embodiment, the variable region is a VH region. In a further embodiment, the variable region is a VL region. In an even further embodiment, the antibody does not comprise a CL region.

In an important embodiment, the monovalent antibody of the invention comprises a heavy chain and a light chain, wherein the heavy chain comprises
(i) a VH region of a selected antigen specific antibody or an antigen binding part of the said region, and
(ii) a CH region as defined above,
and the light chain comprises
(i) a VL region of a selected antigen specific antibody or an antigen binding part of the said region, and
(ii) a CL region which, in case of an IgG1 subtype, has been modified such that the CL region does not contain any amino acids, which are capable of forming disulfide bonds with an identical CL region or other covalent bonds with an identical CL region in the presence of polyclonal human IgG.

Typically, the light chain and the heavy chain of the monovalent antibody defined above are connected to each other via one or more disulfide bonds. It is evident that for such disulphide bonds, neither of the binding partners in the disulphide bond is present in the region corresponding to the hinge region. In one embodiment however the light chain and the heavy chain of the monovalent antibody are connected to each other via one or more amide bonds.

Furthermore, typically, the VL region and the CL region of the light chain are connected to each other via peptide bonds and produced from a single open reading frame.

In one embodiment, the VH and VL region of an antibody molecule of the invention are derived from the same antigen specific antibody.

According to the invention, the sequence of the CL region of the light chain of the antibody molecule may be derived from the sequence of CL region of an immunoglobulin. In one embodiment, the CL region is the constant region of the kappa light chain of human IgG. In one embodiment, the CL region comprises the amino acid sequence of SEQ ID No: 2. In one embodiment, the CL region is the constant region of the lambda light chain of human IgG. In one embodiment, the CL region comprises the amino acid sequence of SEQ ID No: 4.

In one embodiment, the monovalent antibody of the invention is an IgG1, IgG2, IgG3, IgG4, IgA or IgD antibody, such as an IgG1, IgG2 or IgG4 antibody. In a further embodiment, the monovalent antibody is a human antibody.

A monovalent antibody of the present invention may also be a variant of any of the above isotypes. For example, a variant IgG4 antibody may be an antibody that differs from a IgG4 antibody by one or more suitable amino acid residue alterations, that is substitutions, deletions, insertions, or terminal sequence additions, for instance in the constant domain, and/or the variable regions (or any one or more CDRs thereof) in a single variant antibody. Typically, amino acid sequence alterations, desirably do not substantially change the structural characteristics of the parent sequence (e.g., a replacement amino acid should not tend to disrupt secondary structure that characterizes the function of the parent sequence), but which may be associated with advantageous properties, such as changing the functional or pharmacokinetic properties of the antibodies, for example increasing the half-life, altering the immunogenicity, providing a site for covalent or non-covalent binding to another molecule, reducing susceptibility to proteolysis or reducing susceptibility to oxidation. Examples of variants include variants which have a modification of the CH3 region, such as a substitution or deletion at any one or more of the positions 225, 234, 236, 238, 273 or 275 of SEQ ID NO: 4 or the corresponding residues in non-IgG4 isotypes. Modifications at these positions may e.g. further reduce intermolecular interactions between hinge-modified antibodies of the invention. Other examples include variants which have a modification of the constant region, such as a substitution or deletion, at any one or more of the positions 118, 120, 122, 124, 175, 248, 296, 302 of SEQ ID NO: 4 or the corresponding residues in non-IgG4 isotypes. Modifications at these positions may e.g. increase the half-life of hinge-modified antibodies of the invention.

In one embodiment, the monovalent antibody of the invention comprises the CH3 region as set as set forth in SEQ ID NO: 7, but wherein the CH3 region has been modified so that one or more of the following amino acid substitutions have been made: Arg (R) in position 238 has been replaced by Gln (Q); Asp (D) in position 239 has been replaced by Glu (E); Thr (T) in position 249 has been replaced by Ala (A); Leu (L) in position 251 has been replaced by Ala (A); Leu (L) in position 251 has been replaced by Val (V); Phe (F) in position 288 has been replaced by Ala (A); Phe (F) in position 288 has been replaced by Leu (L); Tyr (Y) in position 290 has been replaced by Ala (A); Lys (K) in position 292 has been replaced by Arg (R); Lys (K) in position 292 has been replaced by Ala (A); Gln (Q) in position 302 has been replaced by Glu (E); and Pro (P) in position 328 has been replaced by Leu (L).

In a further embodiment hereof, one or more of the following amino acid substitutions have been made: Arg (R) in position 238 has been replaced by Gln (Q); Asp (D) in position 239 has been replaced by Glu (E); Lys (K) in position 292 has been replaced by Arg (R); Gln (Q) in position 302 has been replaced by Glu (E); and Pro (P) in position 328 has been replaced by Leu (L). In an even further embodiment:

(i) Arg (R) in position 238 has been replaced by Gln (Q),
(ii) Arg (R) in position 238 has been replaced by Gln (Q), and Pro (P) in position 328 has been replaced by Leu (L), or
(iii) all five substitutions as defined above have been made.

In another further embodiment hereof, the monovalent antibody further comprises the CH1 and/or CH2 regions as set forth in SEQ ID NO: 7, with the proviso that the CH2 region has been modified so that it does not comprise any acceptor sites for N-linked glycosylation.

In one embodiment, the monovalent antibody of the invention comprises the kappa CL region having the amino acid sequence as set forth in SEQ ID NO: 6, but wherein the sequence has been modified so that the terminal cysteine residue in position 106 has been replaced with another amino acid residue or has been deleted.

In another embodiment, the monovalent antibody of the invention comprises the lambda CL region having the amino acid sequence as set forth in SEQ ID NO: 5, but wherein the sequence has been modified so that the cysteine residue in position 104 has been replaced with another amino acid residue or has been deleted.

In a further embodiment, the monovalent antibody of the invention comprises the CH1 region as set forth in SEQ ID NO: 7, but wherein the CH1 region has been modified so that Ser (S) in position 14 has been replaced by a cysteine residue.

In a different embodiment, the monovalent antibody of the invention comprises the CH3 region as set forth in SEQ ID NO: 8, but wherein the CH3 region has been modified so that one or more of the of the following amino acid substitutions have been made: Arg (R) in position 234 has been replaced by Gln (Q); Thr (T) in position 245 has been replaced by Ala (A); Leu (L) in position 247 has been replaced by Ala (A); Leu (L) in position 247 has been replaced by Val (V); Met (M) in position 276 has been replaced by Val (V); Phe (F) in position 284 has been replaced by Ala (A); Phe (F) in position 284 has been replaced by Leu (L); Tyr (Y) in position 286 has been replaced by Ala (A); Lys (K) in position 288 has been replaced by Arg (R); Lys (K) in position 288 has been replaced by Ala (A); Gln (Q) in position 298 has been replaced by Glu (E); and Pro (P) in position 324 has been replaced by Leu (L).

In a further embodiment hereof, one or more of the of the following amino acid substitutions have been made: Arg (R) in position 234 has been replaced by Gln (Q); Met (M) in position 276 has been replaced by Val (V); Lys (K) in position 288 has been replaced by Arg (R); Gln (Q) in position 298 has been replaced by Glu (E); and Pro (P) in position 324 has been replaced by Leu (L). In an even further embodiment:

(i) Arg (R) in position 234 has been replaced by Gln (Q);
(ii) Arg (R) in position 234 has been replaced by Gln (Q); and Pro (P) in position 324 has been replaced by Leu (L); or
(iii) all five substitutions as defined above have been made.

In another further embodiment hereof, the monovalent antibody further comprises the CH1 and/or CH2 regions as set forth in SEQ ID NO: 8, with the proviso that the CH2 region has been modified so that it does not comprise any acceptor sites for N-linked glycosylation.

In a further different embodiment, the monovalent antibody of the invention comprises the CH3 region as set forth in SEQ ID NO: 9, but wherein the CH3 region has been modified so that one or more of the following amino acid substitutions have been made: Arg (R) in position 285 has been replaced by Gln (Q); Thr (T) in position 296 has been replaced by Ala (A); Leu (L) in position 298 has been replaced by Ala (A); Leu (L) in position 298 has been replaced by Val (V); Ser (S) in position 314 has been replaced by Asn (N); Asn (N) in position 322 has been replaced by Lys (K); Met (M) in position 327 has been replaced by Val (V); Phe (F) in position 335 has been replaced by Ala (A); Phe (F) in position 335 has been replaced by Leu (L); Tyr (Y) in position 337 has been replaced by Ala (A); Lys (K) in position 339 has been replaced by Arg (R); Lys (K) in position 339 has been replaced by Ala (A); Gln (Q) in position 349 has been replaced by Glu (E); Ile (I) in position 352 has been replaced by Val (V); Arg (R) in position 365 has been replaced by His (H); Phe (F) in position 366 has been replaced by Tyr (Y); and Pro (P) in position 375 has been replaced by Leu (L), with the proviso that the CH3 region has been modified so that it does not comprise any acceptor sites for N-linked glycosylation.

In a further embodiment hereof, one or more of the of the following amino acid substitutions have been made: Arg (R) in position 285 has been replaced by Gln (Q); Ser (S) in position 314 has been replaced by Asn (N); Asn (N) in position 322 has been replaced by Lys (K); Met (M) in position 327 has been replaced by Val (V); Lys (K) in position 339 has been replaced by Arg (R); Gln (Q) in position 349 has been replaced by Glu (E); Ile (I) in position 352 has been replaced by Val (V); Arg (R) in position 365 has been replaced by His (H); Phe (F) in position 366 has been replaced by Tyr (Y); and Pro (P) in position 375 has been replaced by Leu (L). In an even further embodiment: (i) Arg (R) in position 285 has been replaced by Gln (Q), (ii) Arg (R) in position 285 has been replaced by Gln (Q); and Pro (P) in position 375 has been replaced by Leu (L), or (iii) all ten substitutions as defined above have been made.

In another further embodiment hereof, the monovalent antibody further comprises the CH1 and/or CH2 regions as set forth in SEQ ID NO: 9, with the proviso that the CH2 region has been modified so that it does not comprise any acceptor sites for N-linked glycosylation.

In further embodiments, the monovalent antibody according to the invention has been further modified e.g. in the CH2 and/or CH3 region, for example, to reduce the ability of the monovalent antibody to dimerize or to improve the pharmacokinetic profile, e.g. via improving the binding to FcRn.

Examples of such modifications include the following substitutions (reference is here made to IgG4 residues given in SEQ ID NO:4, but the same substitutions may be made in corresponding residues in other isotypes, such as IgG1. These corresponding residues may be found by simply alignment of the sequence): in the CH3 region: T234A, L236A, L236V, F273A, F273L, Y275A, E225A, D267A, L236E, L236G, F273D, F273T, Y275E, and in the CH2 region: T118Q, M296L, M120Y, S122T, T124E, N302A, T175A, E248A, N302A. Two or more of the above mentioned substitutions made combined to obtain the combined effects.

Thus, in one embodiment, the monovalent antibody comprises the CH3 region as set forth in SEQ ID NO: 4.

However, in another embodiment, the monovalent antibody comprises the CH3 region as set forth in SEQ ID NO: 4, but:
  Glu (E) in position 225 has been replaced by Ala (A), and/or
  Thr (T) in position 234 has been replaced by Ala (A), and/or
  Leu (L) in position 236 has been replaced by Ala (A), Val (V), Glu (E) or Gly (G), and/or
  Asp (D) in position 267 has been replaced by Ala (A), and/or
  Phe (F) in position 273 has been replaced by Ala (A) or Leu (L).
  Tyr (Y) in position 275 has been replaced by Ala (A).

In another embodiment, the monovalent antibody comprises the CH3 region as set forth in SEQ ID NO: 4, but:
  Glu (E) in position 225 has been replaced by Ala (A), and/or
  Thr (T) in position 234 has been replaced by Ala (A), and/or
  Leu (L) in position 236 has been replaced by Ala (A), Val (V), Glu (E) or Gly (G), and/or
  Asp (D) in position 267 has been replaced by Ala (A), and/or
  Phe (F) in position 273 has been replaced by Asp (D) and Tyr (Y) in position 275 has been replaced by Glu (E).

In another embodiment, the monovalent antibody comprises the CH3 region as set forth in SEQ ID NO: 4, but:
  Glu (E) in position 225 has been replaced by Ala (A), and/or
  Thr (T) in position 234 has been replaced by Ala (A), and/or
  Leu (L) in position 236 has been replaced by Ala (A), Val (V), Glu (E) or Gly (G), and/or
  Asp (D) in position 267 has been replaced by Ala (A), and/or
  Phe (F) in position 273 has been replaced by Thr (T) and Tyr (Y) in position 275 has been replaced by Glu (E).

In one embodiment, the monovalent antibody comprises the CH2 region as set forth in SEQ ID NO: 4, but wherein Thr (T) in position 118 has been replaced by Gln (Q) and/or Met (M) in position 296 has been replaced by Leu (L).

In another embodiment, the monovalent antibody comprises the CH2 region as set forth in SEQ ID NO: 4, but wherein one, two or all three of the following substitutions have been made: Met (M) in position 120 has been replaced by Tyr (Y); Ser (S) in position 122 has been replaced by Thr (T); and Thr (T) in position 124 has been replaced by Glu (E).

In another embodiment, the monovalent antibody comprises the CH2 region as set forth in SEQ ID NO: 4, but wherein Asn (N) in position 302 has been replaced by Ala (A).

In a yet other embodiment, the monovalent antibody comprises the CH2 region as set forth in SEQ ID NO: 4, but wherein Asn (N) in position 302 has been replaced by Ala (A) and Thr (T) in position 175 has been replaced by Ala (A) and Glu (E) in position 248 has been replaced by Ala (A).

In an even further different embodiment, the antibody of the invention comprises the CH3 region as set forth in SEQ ID NO: 4, and wherein the CH3 region has been modified so that one or more of the following amino acid substitutions have been made: Thr (T) in position 234 has been replaced by Ala (A); Leu (L) in position 236 has been replaced by Ala (A); Leu (L) in position 236 has been replaced by Val (V); Phe (F) in position 273 has been replaced by Ala (A); Phe (F) in position 273 has been replaced by Leu (L); Tyr (Y) in position 275 has been replaced by Ala (A); Arg (R) in position 277 has been replaced by Ala (A).

Preferred substitutions include: replacement of Leu (L) in position 236 by Val (V), replacement of Phe (F) in position 273 by Ala (A) and replacement of Tyr (Y) in position 275 by Ala (A).

In one embodiment of the invention, the monovalent antibody does not bind to the synthetic antigen (Tyr, Glu)-Ala-Lys.

The hinge region is a region of an antibody situated between the CH1 and CH2 regions of the constant domain of the heavy chain. The extent of the hinge region is determined by the separate exon, which encodes the hinge region. The hinge region is normally involved in participating in ensuring the correct assembly of the four peptide chains of an antibody into the traditional tetrameric form via the formation of disulphide bonds, or bridges, between one or more cysteine residues in the hinge region of one of the heavy chains and one or more cysteine residues in the hinge region of the other heavy chain. A modification of the hinge region so that none of the amino acid residues in the hinge region are capable of participating in the formation of disulphide bonds may thus for instance comprise the deletion and/or substitution of the cysteine residues present in the unmodified hinge region. A region corresponding to the hinge region should for the purpose of this specification be construed to mean the region between region CH1 and CH2 of a heavy chain of an antibody. In the context of the present invention, such a region may also comprise no amino acid residues at all, corresponding to a deletion of the hinge region, resulting in the CH1 and CH2 regions being connected to each other without any intervening amino acid residues. Such a region may also comprise only one or a few amino acid residues, which residues need not be the amino acid residues present in the N- or C-terminal of the original hinge region.

Accordingly, in one embodiment of the antibody of the invention, the CH region has been modified such that the region corresponding to the hinge region of the CH region does not comprise any cysteine residues. In another embodiment, the CH region has been modified such that at least all cysteine residues have been deleted and/or substituted with other amino acid residues. In a further embodiment, the CH region has been modified such that the cysteine residues of the hinge region have been substituted with amino acid residues that have an uncharged polar side chain or a nonpolar side chain. Preferably, the amino acids with uncharged polar side chains are independently selected from asparagine, glutamine, serine, threonine, tyrosine, and tryptophan, and the amino acid with the nonpolar side chain are independently selected from alanine, valine, leucine, isoleucine, proline, phenylalanine, and methionine.

In an even further embodiment, the monovalent antibody is a human IgG4, wherein the amino acids corresponding to amino acids 106 and 109 of the CH sequence of SEQ ID No: 2 have been deleted.

In a yet further embodiment, the monovalent antibody is a human IgG4, wherein one of the amino acid residues corresponding to amino acid residues 106 and 109 of the sequence of SEQ ID No: 2 has been substituted with an amino acid residue different from cysteine, and the other of the amino acid residues corresponding to amino acid residues 106 and 109 of the sequence of SEQ ID No: 2 has been deleted.

In a yet further embodiment, the amino acid residue corresponding to amino acid residue 106 has been substituted with an amino acid residue different from cysteine, and the amino acid residue corresponding to amino acid residue 109 has been deleted.

In a yet further embodiment, the amino acid residue corresponding to amino acid residue 106 has been deleted, and the amino acid residue corresponding to amino acid residue 109 has been substituted with an amino acid residue different from cysteine.

In a yet further embodiment, the monovalent antibody is a human IgG4, wherein at least the amino acid residues corresponding to amino acid residues 106 to 109 of the CH sequence of SEQ ID No: 2 have been deleted.

In a yet further embodiment, the monovalent antibody is a human IgG4, wherein at least the amino acid residues corresponding to amino acid residues 99 to 110 of the sequence of SEQ ID No: 2 have been deleted.

In a yet further embodiment, the CH region comprises the amino acid sequence of SEQ ID No: 4.

In a yet even further embodiment, the monovalent antibody is a human IgG4, wherein the CH region has been modified such that the entire hinge region has been deleted.

In a further embodiment, the sequence of the antibody has been modified so that it does not comprise any acceptor sites for N-linked glycosylation. In a further embodiment hereof, the NST acceptor site for N-linked glycosylation in the CH2 region has been modified to a sequence selected from the group consisting of: GST, MST, CSE, DSE, DSP, ESP, GSP, HSE, NSE, PSP and SSE.

In one embodiment, the monovalent antibody of the invention is monovalent in the presence of physiological concentrations of polyclonal human IgG.

The antibodies of the present invention has the advantage of having a long half-life in vivo, leading to a longer therapeutic window, as compared to e.g. a FAB fragment of the same antibody which has a considerably shorter half-life in vivo.

Further, due to the long half-life and small size, the monovalent antibodies of the invention will have a potential having a better distribution in vivo, in example by being able to penetrate solid tumors. This leads to a great use potential of the monovalent antibodies of the invention, e.g. for treatment of cancer, since the antibodies of the invention could be used either to inhibit a target molecule, or as a target specific delivery mechanism for other drugs that would treat the disease.

Accordingly, in one embodiment, the monovalent antibody of the invention has a plasma concentration above 10 µg/ml for more than 7 days when administered in vivo at a dose of 4 mg per kg, as measured in an pharmacokinetic study in SCID mice (for instance as shown in the WO2007059782). The clearance rate of a monovalent antibody of the invention may be measured by use of pharmacokinetic methods as it is known in the art. The antibody may for instance be injected intravenously (other routes such as i.p. or i.m. may also be used) in a human or animal after which blood samples are drawn by venipuncture at several time points, for instance 1 hour, 4 hours, 24 hours, 3 days, 7 days, 14 days, 21 days and 28 days after initial injection). The concentration of antibody in the serum is determined by an appropriate assay such as ELISA. Pharmacokinetic analysis can performed as known in the art and described in WO2007059782. Monovalent antibodies of the invention may have a plasma residence time, which is as much as 100 times longer than the plasma residence time of for instance Fab fragments which are frequently used as monovalent antibodies.

In one embodiment, a monovalent antibody of the invention has a plasma clearance, which is more than 10 times slower than the plasma clearance of a F(ab')$_2$ fragment, which has a comparable molecular size. This may be an indication of the capability of the antibodies of the invention to bind to FcRn. FcRn is a major histocompatibility complex class I-related receptor and plays a role in the passive delivery of immunoglobulin (Ig)Gs from mother to young and in the regulation of serum IgG levels by protecting IgG from intracellular degradation (Ghetie V et al., Annu Rev Immunol. 18, 739-66 (2000)). In one embodiment, the F(ab')$_2$ fragment is directed at the same antigen as the monovalent antibody of the invention. In one embodiment, the F(ab')$_2$ fragment is directed at the same epitope as the monovalent antibody of the invention. In one embodiment, the VH region and the VL region of the F(ab')$_2$ fragment are identical to the VH region and the VL region of the monovalent antibody of the invention.

In one embodiment, a monovalent antibody of the invention has a half-life of at least 5 days when administered in vivo. The half-life of a monovalent antibody of the invention may be measured by any method known in the art, for instance as described above.

In one embodiment, a monovalent antibody of the invention has a half-life of at least 5 days and up to 14 days, when administered in vivo.

In one embodiment, the monovalent antibody of the invention has a half-life of at least 5 days and up to 21 days, when administered in vivo.

In an even further embodiment, the monovalent antibody has a serum half-life of at least 5 days, such as of at least 14 days, for example of from 5 and up to 21 days when administered in vivo to a human being or a SCID mouse.

In one embodiment, the monovalent antibody of the invention binds to a tumor antigen with a dissociation constant ($k_d$) of $10^{-7}$ M or less, such as $10^{-8}$ M or less.

In another embodiment, the monovalent antibody of the invention binds to a cell surface receptor with a dissociation constant ($k_d$) of $10^{-7}$ M or less, such as $10^{-8}$ M or less, which cell surface receptor is activated upon receptor dimerization.

In a further embodiment, the monovalent antibody binds to a target with a dissociation constant ($k_d$) of $10^{-7}$ M or less, such as $10^{-8}$ M or less, which target is selected from: erythropoietin, beta-amyloid, thrombopoietin, interferon-alpha (2a and 2b), -beta (1b), -gamma, TNFR I (CD120a), TNFR II (CD120b), IL-1R type 1 (CD121a), IL-1R type 2 (CD121b), IL-2, IL2R (CD25), IL-2R-beta (CD123), IL-3, IL-4, IL-3R (CD123), IL-4R (CD124), IL-5R (CD125), IL-6R-alpha (CD126), -beta (CD130), IL-10, IL-11, IL-15BP, IL-15R, IL-20, IL-21, TCR variable chain, RANK, RANK-L, CTLA4, CXCR4R, CCR5R, TGF-beta1, -beta2, -beta3, G-CSF, GM-CSF, MIF-R (CD74), M-CSF-R (CD115), GM-CSFR (CD116), soluble FcRI, sFcRll, sFcRIII, FcRn, Factor VII, Factor VIII, Factor IX, VEGF, VEGFxxxb, anti-psychotic drugs, anti-depressant drugs, anti-Parkinson drugs, anti-seizure agents, neuromuscular blocking drugs, anti-epileptic drugs, adrenocorticosteroids, insulin, proteins or enzymes involved in regulation of insulin, incretins (GIP and GLP-1) or drugs mimicking incretin action such as Exenatide and sitagliptin, thyroid hormones, growth hormone, ACTH, oestrogen, testosterone, anti-diuretic hormone, diuretics, blood products such as heparin and EPO, beta-blocking agents, cytotoxic agents, anti-viral drugs, anti-bacterial agents, anti-fungal agents, anti-parasitic drugs, anti-coagulation drugs, anti-inflammatory drugs, anti-asthma drugs, anti-COPD drugs, opiates, morphine, vitamins (such as vitamin C for conservation), hormones involved in pregnancy such as LH and FSH, hormones involved in sex changes, anti-conceptives and antibodies.

In one embodiment, a monovalent antibody of the invention specifically binds a cell surface receptor that is activated upon receptor dimerization. Monovalent antibodies, such as the monovalent antibodies of the invention, may often be useful in the treatment of diseases or disorders, where receptor activation is undesirable, since the antibody molecules of the inventions due to their monovalent nature are unable to induce such dimerization and thereby such activation. Without being limited to specific receptors, examples of such receptors could be erb-B1, erb-B2, erb-B3, erb-B4 and members of the ephrins and ephrin receptors such as ephrin-A1 through A6, ephA1 through A8, ephrin B1 through B3 and eph-B1 through eph-B6.

In one embodiment, a monovalent antibody of the invention, when bound to a target molecule, inhibits target molecule multimerization (such as dimerization). Again, monovalent antibodies, such as the monovalent antibodies of the invention, may often be useful in the treatment of diseases or disorders, where multimerization of the target antigen is undesirable, since the antibody molecules of the inventions due to their monovalent nature are unable to induce such multimerization. In the case of soluble antigens, multimerization may form undesirable immune complexes. Without being limited to specific targets, examples of such targets could be Toll-like receptors such as TLR-3 and TLR-9, or angiopoietin-1, or angiopoietin-2, or TNF receptor family members such as CD30, CD40 and CD95.

In one embodiment, a monovalent antibody of the invention is an inhibitor of TNF-alpha. In one embodiment of the invention, the monovalent antibody of the invention is a monovalent form of adalimumab, etanercept, or infliximab.

In a further embodiment, the monovalent antibody binds to a target with a dissociation constant ($k_d$) of $10^{-7}$ M or less, such as $10^{-8}$ M or less, which target is selected from VEGF, c-Met, CD20, CD38, IL-8, CD25, CD74, FcalphaRI, FcepsilonRI, acetyl choline receptor, f as, fasL, TRAIL, hepatitis virus, hepatitis C virus, envelope E2 of hepatitis C virus, tissue factor, a complex of tissue factor and Factor VII, EGFr, CD4, and CD28.

In one embodiment, an anti-VEGF monovalent antibody is used for treatment of AMD (acute macular degeneration), and other diseases.

In one embodiment, the anti-VEGF monovalent antibody used is a monovalent form of bevacizumab (Avastin).

In an even further embodiment, the monovalent antibody is a human IgG4 antibody and which binds to c-Met with a dissociation constant ($k_d$) of $10^{-7}$ M or less, such as $10^{-8}$ M or less.'

In one embodiment, a monovalent antibody of the invention is incapable of effector binding. The expression "incapable of effector binding" or "inability of effector binding" in the present context means that a monovalent antibody of the invention is incapable of binding to the C1q component of the first component of complement (C1) and therefore is unable of activating the classical pathway of complement mediated cytotoxicity. In addition, the monovalent antibodies of the invention are unable to interact with Fc receptors and may therefore be unable to trigger Fc receptor-mediated effector functions such as phagocytosis, cell activation, induction of cytokine release In one embodiment, a monovalent antibody of the invention is produced by use of recombinant DNA technologies. Antibodies may be produced using recombinant eukaryotic host cells, such as Chinese hamster ovary (CHO) cells, NS/0 cells, HEK293 cells, insect cells, plant cells, or fungi, including yeast cells. Both stable as well as transient systems may be used for this purpose. Transfection may be done using plasmid expression vectors by a number of established methods, such as electroporation, lipofection or nucleofection. Alternatively, infection may be used to express proteins encoded by recombinant viruses such as adeno, vaccinia or baculoviruses. Another method may be to use transgenic animals for production of antibodies.

Thus, in a further main aspect, the invention relates to a nucleic acid construct encoding the monovalent antibody of the invention as described herein. In one embodiment, said nucleic acid construct is an expression vector.

Furthermore, the invention relates to a method of preparing a monovalent antibody according to the invention comprising culturing a host cell comprising a nucleic acid construct according to invention, so that the monovalent antibody is produced, and recovering the said monovalent antibody from the cell culture.

A DNA sequence encoding the antibody may be prepared synthetically by established standard methods. The DNA sequence may then be inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e. a vector that exists as an extrachromosomal entity, the replication of which is independent of chromosomal replication, for instance a plasmid. Alternatively, the vector may be one which, when introduced into a host cell, is integrated into the host cell genome and replicated together with the chromosome(s) into which it has been integrated. In the vector, a DNA sequence encoding the antibody should be operably connected to a suitable promoter sequence. The coding DNA sequence may also be operably connected to a suitable terminator and the vector may further comprise elements such as polyadenylation signals (for instance from SV40 or the adenovirus 5 Elb region), transcriptional enhancer sequences (for instance the SV40 enhancer) and translational enhancer sequences (for instance the ones encoding adenovirus VA RNAs). Other such signals and enhancers are known in the art.

To obtain recombinant monovalent antibodies of the invention, the DNA sequences encoding different parts of the polypeptide chain(s) of the antibody may be individually expressed in a host cell, or may be fused, giving a DNA construct encoding the fusion polypeptide, such as a polypeptide comprising both light and heavy chains, inserted into a recombinant expression vector, and expressed in host cells.

Thus, in a further aspect, the invention relates to a host cell comprising a nucleic acid according to the invention.

The invention also relate to a non-human transgenic animal comprising a nucleic acid construct according to the invention.

The host cell into which the expression vector may be introduced, may be any cell which is capable of expression of full-length proteins, and may for instance be a prokaryotic or eukaryotic cell, such as yeast, insect or mammalian cells. Examples of suitable mammalian cell lines are the HEK293 (ATCC CRL-1573), COS (ATCC CRL-1650), BHK (ATCC CRL-1632, ATCC CCL-10), NS/0 (ECACC 85110503) or CHO (ATCC CCL-61) cell lines. Other suitable cell lines are known in the art. In one embodiment, the expression system is a mammalian expression system, such as a mammalian cell expression system comprising various clonal variations of HEK293 cells.

Methods of transfecting mammalian cells and expressing DNA sequences introduced in the cells are well known in the art. To obtain a monovalent antibody of the invention, host cells of the expression system may in one embodiment to be cotransfected with two expression vectors simultaneously, wherein first of said two expression vectors comprises a DNA sequence encoding the heavy chain of the antibody, and second of said two expression vectors comprises a DNA sequence encoding the light chain of the antibody. The two sequences may also be present on the same expression vector, or they may be fused giving a DNA construct encoding the fusion polypeptide, such as a polypeptide comprising both light and heavy chains.

The recombinantly produced monovalent antibody may then be recovered from the culture medium by conventional procedures including separating the host cells from the medium by centrifugation or filtration, precipitating the proteinaceous components of the supernatant or filtrate by means of a salt, for instance ammonium sulphate, purification by a variety of chromatographic procedures, for instance HPLC, ion exchange chromatography, affinity chromatography, Protein A chromatography, Protein G chromatography, or the like.

The present invention also relates to a method of preparing a monovalent antibody of the invention, wherein said method comprises the steps of:
(a) culturing a host cell comprising a nucleic acid encoding said monovalent antibody; and
(b) recovering the monovalent antibody from the host cell culture.

In one embodiment, said host cell is a prokaryotic host cell. In one embodiment, the host cell is an E. coli cell. In one embodiment, the E. coli cells are of a strain deficient in endogenous protease activities.

In one embodiment, said host cell is a eukaryotic cell. In one embodiment, the host cell is a HEK-293F cell. In another embodiment, the host cell is a CHO cell.

In one embodiment, the monovalent antibody is recovered from culture medium. In another embodiment, the monovalent antibody is recovered from cell lysate.

In a further main aspect, the invention relates to a pharmaceutical composition comprising the monovalent antibody according to the invention. In one embodiment, the composition further comprises one or more further therapeutic agents described herein.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, $19^{th}$ Edition, Gennaro, Ed., Mack Publishing Co., Easton, Pa., 1995. As used herein, "pharmaceutically acceptable carrier" includes any and all solvents, dispersion media, coatings, antibacterial and antifungal agents, isotonicity agents, antioxidants and absorption delaying agents, and the like that are physiologically compatible.

The pharmaceutical composition may be administered by any suitable route and mode. As will be appreciated by the skilled artisan, the route and/or mode of administration will vary depending upon the desired results.

In one embodiment, the pharmaceutical composition is suitable for parenteral administration. The phrase "parenteral administration" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In one embodiment the pharmaceutical composition is administered by intravenous or subcutaneous injection or infusion.

Regardless of the route of administration selected, the monovalent antibodies of the present invention, which may be used in the form of a pharmaceutically acceptable salt or in a suitable hydrated form, and/or the pharmaceutical compositions of the present invention, are formulated into pharmaceutically acceptable dosage forms by conventional methods known to those of skill in the art.

Dosage regimens are adjusted to provide the optimum desired response (for instance a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of monovalent antibody calculated to produce the desired therapeutic effect in association with the required pharmaceutical carrier. The specification for the dosage unit forms of the invention are dictated by and directly dependent on (a) the unique characteristics of the monovalent antibody and the particular therapeutic effect to be achieved, and (b) the limitations inherent in the art of compounding such a monovalent antibody for the treatment of sensitivity in individuals.

Actual dosage levels of the monovalent antibodies in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular monovalent antibodies of the present invention employed, the route of administration, the time of administration, the rate of excretion of the particular monovalent antibody being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable dose of a pharmaceutical composition of the invention will be that amount of the monovalent antibody which is the lowest dose effective to produce a therapeutic effect. Such an effective dose will generally depend upon the factors described above. As another example, the physician or veterinarian may start with a high loading dose followed by repeated administration of lower doses to rapidly build up a therapeutically effective dose and maintain it over longer periods of time.

A pharmaceutical composition of the invention may contain one or a combination of different monovalent antibodies of the invention. Thus, in a further embodiment, the pharmaceutical compositions include a combination of multiple (for instance two or more) monovalent antibodies of the invention which act by different mechanisms. The monovalent antibodies may also be thus combined with divalent antibodies.

The monovalent antibody of the present invention have numerous in vitro and in vivo diagnostic and therapeutic utilities involving the diagnosis and treatment of disorders involving cells expressing the antigen which the antibody can recognize and bind to. In certain pathological conditions, it is necessary and/or desirable to utilize monovalent antibodies. Also, in some instances, it is preferred that a therapeutic antibody effects its therapeutic action without involving immune system-mediated activities, such as the effector functions, ADCC, phagocytosis and CDC. In such situations, it is desirable to generate forms of antibodies in which such activities are substantially reduced or eliminated. It is also advantageous if the antibody is of a form that can be made efficiently and with high yield. The present invention provides such antibodies, which may be used for a variety of purposes, for example as therapeutics, prophylactics and diagnostics.

In one embodiment, a monovalent antibody of the invention is directed to CD74 and inhibits MIF-induced signaling, but lacks Fc-mediated effector functions.

In one embodiment, a monovalent antibody of the invention may prevent binding of a virus or other pathogen to its receptor, such as inhibition of HIV binding to CD4 or coreceptor such as CCR5 or CXCR4.

The scientific literature is abundant with examples of targets, where the binding of antibodies against said target, or specific epitopes of said target, is shown to have, or is expected to have, a therapeutic effect. Given the teaching of this specification and as described elsewhere herein, it is within the skill of a person skilled in the art to determine, whether the use of a monovalent antibody, such as a monovalent antibody of the present invention, against such targets would be expected to produce the therapeutic effect.

Accordingly, in a further aspect, the invention relates to the monovalent antibody according to the invention as described herein for use as a medicament.

In another aspect, the invention relates to the monovalent antibody according to the invention for use in the treatment of cancer.

In another aspect, the invention relates to the monovalent antibody according to the invention for use in the treatment of an inflammatory condition.

In another aspect, the invention relates to the monovalent antibody according to the invention for use in the treatment of an auto(immune) disorder.

In another aspect, the invention relates to the monovalent antibody according to the invention for use in the treatment of a disorder involving undesired angiogenesis.

In a further aspect, the invention relates to the monovalent antibody according to the invention for use in the treatment of a disease or disorder, which disease or disorder is treatable by administration of an antibody against a certain target, wherein the involvement of immune system-mediated activities is not necessary or is undesirable for achieving the effects of the administration of the antibody, and wherein said antibody specifically binds said antigen.

In a further aspect, the invention relates to the monovalent antibody according to the invention for use in the treatment of a disease or disorder, which disease or disorder is treatable by blocking or inhibiting a soluble antigen, wherein multimerization of said antigen may form undesirable immune complexes, and wherein said antibody specifically binds said antigen.

In a further aspect, the invention relates to the monovalent antibody according to the invention for use in the treatment of a disease or disorder, which disease or disorder is treatable by blocking or inhibiting a cell membrane bound receptor, wherein said receptor may be activated by dimerization of said receptor, and wherein said antibody specifically binds said receptor.

In one embodiment of any of the above treatments, the treatment comprises administering one or more further therapeutic agents.

Similarly, the invention relates to the use of the monovalent antibody according to the invention as described herein as a medicament.

The invention also relates to a method of treating a disease or disorder as defined herein, wherein said method comprises administering to a subject in need of such treatment a therapeutically effective amount of a monovalent antibody according the invention, a pharmaceutical composition according to the invention or a nucleic acid construct according to the invention. In one embodiment, the treatment comprises administering one or more further therapeutic agents.

Furthermore, the invention relates to the use of the monovalent antibody according to the invention in the preparation of a medicament for the treatment of a disease or disorder as defined herein.

In one embodiment of the invention, the disease or disorder to be treated is treatable by interference with cell activation through FcαRI, by interference with FcαRI function, by inhibition of subsequent FcαRI activated IgE mediated responses, or by binding of soluble FcαRI. In one embodiment of the invention, the monovalent antibody is directed against FcαRI and induces apoptosis of FcαRI expressing cells. In one embodiment, such disease or disorder may for instance be allergic asthma or other allergic diseases such as allergic rhinitis, seasonal/perennial allergies, hay fever, nasal allergies, atopic dermatitis, eczema, hives, urticaria, contact allergies, allergic conjunctivitis, ocular allergies, food and drug allergies, latex allergies, or insect allergies, or IgA nephropathy, such as IgA pemphigus. In one such embodiment, the monovalent antibody of the invention is directed at FcαRI. Such monovalent antibodies may also be used for in vitro or in vivo screening for FcαRI in sample or patient or in an immunotoxin or radiolabel approach to treating these diseases and disorders.

In one embodiment of the invention, the disease or disorder to be treated is treatable by downregulating Fc receptor γ-chain mediated signaling through FcεR1 or Fcγ receptors. Monomeric binding of antibody to FcαRI is known to effect such inhibition. Monovalent antibodies may thus be used to inhibit immune activation through a range of Fc receptors including Fcγ, Fcα and FCε receptors. Thus, in one embodiment, the monovalent antibody of the invention may bind an Fcα, Fcε or Fcγ receptor, such as CD32b.

In one such embodiment, the monovalent antibody of the invention is directed at CD25. Such monovalent antibodies may also be used for in vitro or in vivo screening for CD25 in sample or patient or in an immunotoxin or radiolabel approach to treating these diseases and disorders.

In one embodiment of the invention, the disease or disorder to be treated is treatable by antagonizing and/or inhibiting IL-15 or IL15 receptor functions. In one embodiment, such disease or disorder may for instance be arthritides, gout, connective, neurological, gastrointestinal, hepatic, allergic, hematologic, skin, pulmonary, malignant, endocrinological, vascular, infectious, kidney, cardiac, circulatory, metabolic, bone, and muscle disorders. In one such embodiment, the monovalent antibody of the invention is directed at IL-15. Such monovalent antibodies may also be used for in vitro or in vivo screening for IL-15 in a sample or patient or in an immunotoxin or radiolabel approach to treating these diseases and disorders.

In one embodiment of the invention, the disease or disorder to be treated is treatable by interfering with CD20 activity, by depleting B cells, interfering with B cell growth and/or proliferation through for instance an immunotoxin or radiolabel approach. In one embodiment, such disease or disorder may for instance be rheumatoid arthritis, (auto) immune and inflammatory disorders (as described above for IL-8 related diseases and disorders), non-Hodgkin's lymphoma, B-CLL, lymphoid neoplasms, malignancies and hematological disorders, infectious diseases and connective, neurological, gastrointestinal, hepatic, allergic, hematologic, skin, pulmonary, malignant, endocrinological, vascular, infectious, kidney, cardiac, circulatory, metabolic, bone and muscle disorders, and immune mediated cytopenia.

In one such embodiment, the monovalent antibody of the invention is directed at CD20. Such monovalent antibodies may also be used for in vitro or in vivo screening for CD20 in a sample or patient.

In one embodiment of the invention, the disease or disorder to be treated is treatable by interfering with CD38 activity, by depleting CD38 expressing cells, interfering with $CD38^+$ cell growth and/or proliferation through for instance an immunotoxin or radiolabel approach.

In one embodiment of the invention, the disease or disorder to be treated is treatable by blocking ligand-EGFr interaction, blocking EGFr function, depletion of EGFr expressing cells/interference with EGFr+ cell growth and/or proliferation through for instance an immunotoxin or radiolabel approach.

In one such embodiment, the monovalent antibody of the invention is directed at EGFr. Such monovalent antibodies may also be used for in vitro or in vivo screening for EGFr in a sample or patient.

In one embodiment of the invention, the disease or disorder to be treated is treatable by interfering with CD4 function, depletion of CD4 expressing cells/interference with CD4+ cell growth and/or proliferation through for instance an immunotoxin or radiolabel approach. In one embodiment, such disease or disorder may for instance be rheumatoid arthritis, (auto)immune and inflammatory disorders (as described above for IL-8 related diseases and disorders), cutaneous T cell lymphomas, non-cutaneous T cell lymphomas, lymphoid neoplasms, malignancies and hematological disorders, infectious diseases, and connective, neurological, gastrointestinal, hepatic, allergic, hematologic, skin, pulmonary, malignant, endocrinological, vascular, infectious, kidney, cardiac, circulatory, metabolic, bone, and muscle disorders, and immune mediated cytopenia.

In one such embodiment, the monovalent antibody of the invention is directed at CD4. Such monovalent antibodies may also be used for in vitro or in vivo screening for CD4 in a sample or patient.

In one embodiment of the invention, a monovalent antibody directed at CD4 is used for treatment of HIV infection, or for the treatment of AIDS.

In one embodiment of the invention, the monovalent antibodies of the invention are monovalent antibodies of the CD4 antibodies disclosed in WO97/13852.

In one embodiment of the invention, the disease or disorder to be treated is treatable by antagonizing and/or inhibiting CD28 functions, such as preventing of co-stimulatory signals needed in T cell activation. In one embodiment, such disease or disorder may for instance be an inflammatory, autoimmune and immune disorder as indicated above. In one such embodiment, the monovalent antibody of the invention is directed at CD28.

In one embodiment of the invention, the disease or disorder to be treated is treatable by altering Tissue Factor functions, such as altering coagulation or inhibition of tissue factor signalling. In one embodiment, such disease or disorder may for instance be vascular diseases, such as myocardial vascular disease, cerebral vascular disease, retinopathia and macular degeneration, and inflammatory disorders as indicated above.

In one embodiment of the invention, the monovalent antibodies are directed at Tissue factor, or at a complex of Factor VII and Tissue Factor.

In one embodiment of the invention, the disease or disorder to be treated is treatable by interfering with Hepatitis C Virus (HCV) infection. In one such embodiment, the monovalent antibody of the invention is directed at HCV or an HCV receptor such as CD81.

In one embodiment of the invention, the monovalent antibody is a monovalent antibody according to the invention of an antibody as disclosed in WO2000/05266.

In one embodiment of the invention, the disease or disorder to be treated is treatable by prevention of binding of allergen to IgE-sensitized on mast cell. In one embodiment, such disease or disorder may for instance be allergen-immunotherapy of allergic diseases such as asthma, allergic rhinitis, seasonal/perennial allergies, hay fever, nasal allergies, atopic dermatitis, eczema, hives, urticaria, contact allergies, allergic conjunctivitis, ocular allergies, food and drug allergies, latex allergies, and insect allergies.

In one such embodiment, the monovalent antibody(s) of the invention are IgG4 hingeless antibodies directed towards allergen(s).

In certain embodiments, an immunoconjugate comprising a monovalent antibody conjugated with a cytotoxic agent is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell.

Examples of such cytotoxic agents include any of the chemotherapeutic agents noted herein (such as a maytansinoid or a calicheamicin), a radioactive isotope, or a ribonuclease or a DNA endonuclease.

Monovalent antibodies of the invention may be used either alone or in combination with other compositions in a therapy. For instance, a monovalent antibody of the invention may be co-administered with one or more other antibodies, such as monovalent antibodies of the present invention, one or more chemotherapeutic agent(s) (including cocktails of chemotherapeutic agents), one or more other cytotoxic agent(s), one or more anti-angiogenic agent(s), one or more cytokines, one or more growth inhibitory agent(s), one or more anti-inflammatory agent(s), one or more disease modifying antirheumatic drug(s) (DMARD), or one or more immunosuppressive agent(s), depending on the disease or condition to be treated. Where a monovalent antibody of the invention inhibits tumor growth, it may be particularly desirable to combine it with one or more other therapeutic agent(s) which also inhibits tumor growth. For instance, anti-VEGF antibodies blocking VEGF activities may be combined with anti-ErbB antibodies (for instance Trastuzumab (Herceptin), an anti-HER2 antibody) in a treatment of metastatic breast cancer. Alternatively, or additionally, the patient may receive combined radiation therapy (for instance external beam irradiation or therapy with a radioactive labeled agent, such as an antibody). Such combined therapies noted above include combined administration (where the two or more agents are included in the same or separate formulations), and separate administration, in which case, administration of the antibody of the invention may occur prior to, and/or following, administration of the adjunct therapy or therapies.

In one embodiment, the monovalent antibody of the invention is a monovalent form of trastuzumab, for treatment of Her2 positive cancer.

For the prevention or treatment of disease, the appropriate dosage of a monovalent antibody of the invention (when used alone or in combination with other agents such as chemotherapeutic agents) will depend on the type of disease to be treated, the type of antibody, the severity and course of the disease, whether the monovalent antibody is administered for preventive, therapeutic or diagnostic purposes, previous therapy, the patient's clinical history and response to the antibody, and the discretion of the attending physician. The monovalent antibody may be suitably administered to the patient at one time or over a series of treatments.

Such dosages may be administered intermittently, for instance every week or every three weeks (for instance such that the patient receives from about two to about twenty, for instance about six doses of the monovalent antibody). An initial higher loading dose, followed by one or more lower doses may be administered. An exemplary dosing regimen comprises administering an initial loading dose of about 4 mg/kg, followed by a weekly maintenance dose of about 2 mg/kg of the monovalent antibody. However, other dosage regimens may be useful. In one embodiment, the monovalent antibodies of the invention are administered in a weekly dosage of from 50 mg to 4000 mg, for instance of from 250 mg to 2000 mg, such as for example 300 mg, 500 mg, 700 mg, 1000 mg, 1500 mg or 2000 mg, for up to 8 times, such as from 4 to 6 times. The weekly dosage may be divided into two or three subdosages and administered over more than one day. For example, a dosage of 300 mg may be administered over 2 days with 100 mg on day one (1), and 200 mg on day two (2). A dosage of 500 mg may be administered over 3 days with 100 mg on day one (1), 200 mg on day two (2), and 200 mg on day three (3), and a dosage of 700 mg may be administered over 3 days with 100 mg on day 1 (one), 300 mg on day 2 (two), and 300 mg on day 3 (three). The regimen may be repeated one or more times as necessary, for example, after 6 months or 12 months.

The dosage may be determined or adjusted by measuring the amount of circulating monovalent antibodies of the invention upon administration in a biological sample for instance by using anti-idiotypic antibodies which target said monovalent antibodies.

In one embodiment, the monovalent antibodies of the invention may be administered by maintenance therapy, such as, for instance once a week for a period of 6 months or more.

In one embodiment, the monovalent antibodies of the invention may be administered by a regimen including one infusion of a monovalent antibody of the invention followed by an infusion of same monovalent antibody conjugated to a radioisotope. The regimen may be repeated, for instance 7 to 9 days later.

In another main aspect, the invention relates to the use of a monovalent antibody according to the invention as a diagnostic agent.

As described above, in a further aspect, the invention relates to a stabilized IgG4 antibody for use as a medicament, comprising a heavy chain and a light chain, wherein said heavy chain comprises a human IgG4 constant region having the sequence set forth in SEQ ID NO:2, wherein Lys (K) in position 250 has been replaced by Gln (Q) or Glu (E) and wherein the antibody optionally comprises one or more further substitutions, deletions and/or insertions in the constant region as set forth in SEQ ID NO:2.

In one embodiment thereof, the human IgG4 constant region has the sequence set forth in SEQ ID NO:2, wherein X1 at position 189 is Leu and X2 at position 289 is Arg. In another embodiment thereof, the human IgG4 constant region has the sequence set forth in SEQ ID NO:2, wherein X1 at position 189 is Leu and X2 at position 289 is Lys. In yet another embodiment thereof, the human IgG4 constant region has the sequence set forth in SEQ ID NO:2, wherein X1 at position 189 is Val and X2 at position 289 is Arg.

In one further aspect, the invention relates to an isolated stabilized IgG4 antibody for use as a medicament, comprising a heavy chain and a light chain, wherein said heavy chain comprises a human IgG4 constant region having the sequence set forth in SEQ ID NO:2, wherein Lys (K) in position 250 has been replaced by Gln (Q) or Glu (E) and wherein the antibody optionally comprises one or more further substitutions, deletions and/or insertions in the constant region as set forth in SEQ ID NO:2.

In one embodiment thereof, the human IgG4 constant region has the sequence set forth in SEQ ID NO:2, wherein X1 at position 189 is Leu and X2 at position 289 is Arg. In another embodiment thereof, the human IgG4 constant region has the sequence set forth in SEQ ID NO:2, wherein X1 at position 189 is Leu and X2 at position 289 is Lys. In yet another embodiment thereof, the human IgG4 constant region has the sequence set forth in SEQ ID NO:2, wherein X1 at position 189 is Val and X2 at position 289 is Arg.

The stabilized IgG4 antibodies according to the invention have the advantage that they contain a minimal number of sequence changes in the constant region as compared to naturally occurring IgG4. This reduces the risk of immunogenicity when the antibody is used for human therapy.

In one embodiment thereof the stabilized IgG4 antibody does not comprise a Cys-Pro-Pro-Cys sequence in the hinge region.

In one embodiment thereof the CH3 region of the stabilized IgG4 antibody has been replaced by the CH3 region of human IgG1, of human IgG2 or of human IgG3.

In one embodiment thereof the stabilized IgG4 antibody does not comprise a substitution of the Leu (L) residue at the position corresponding to 115 by a Glu (E).

In one embodiment thereof the stabilized IgG4 antibody does comprise a substitution of the Leu (L) residue at the position corresponding to 115 by a Glu (E).

In one embodiment thereof the stabilized IgG4 antibody comprises one or more of the following substitutions an Ala (A) at position 114, an Ala (A) at position 116, an Ala (A) at position 117, an Ala (A) at position 177, an Ala (A) or Val (V) at position 198, an Ala (A) at position 200, an Ala (A) or Gln (Q) at position 202.

In one embodiment thereof the stabilized IgG4 antibody comprises a CXPC or CPXC sequence in the hinge region, wherein X can be any amino acid except for Pro (P).

Figure 14:
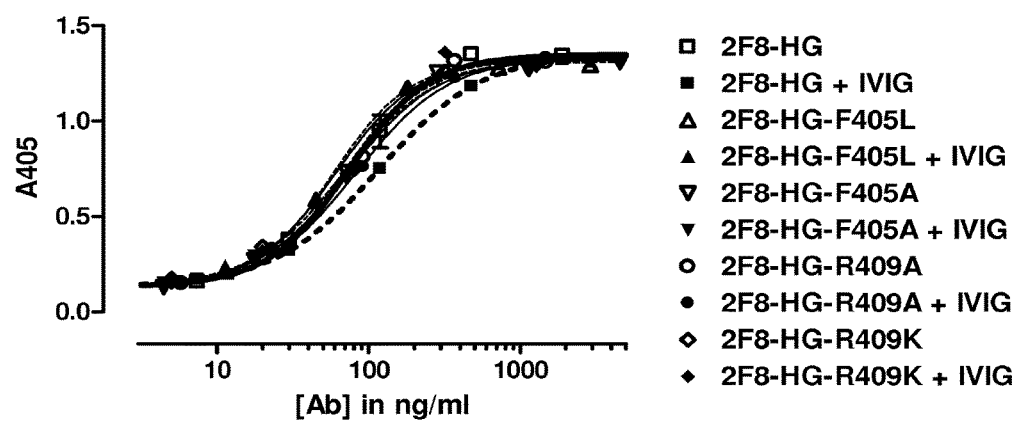
FIG. 14: Binding of hingeless IgG4 antibody 2F8-HG and CH3 variants 2F8-HG-F405L, 2F8-HG-F405A, 2F8-HG-R409A and 2F8-HG-R409K to EGFr (residues are numbered according to EU numbering, see table Example 16). Binding was tested in an EGFR ELISA in the presence and absence of polyclonal human IgG (IVIG).

In one embodiment thereof the stabilized IgG4 antibody does not comprise an extended IgG3-like hinge region, such as the extended hinge region as set forth in FIG. 14.

In one embodiment thereof the stabilized IgG4 antibody comprises a CPSC sequence in the hinge region.

In one embodiment thereof the stabilized IgG4 antibody has less than 25, such as less than 10, e.g. less than 9, 8, 7, 6, 5, 4, 3, or 2 substitutions, deletions and/or insertions in the constant region as set forth in SEQ ID NO:2.

Typically, the stabilized IgG4 antibody of the invention has a lower ability to activate effector functions as compared to IgG1 and IgG3. In one embodiment thereof the antibody is less efficient in mediating CDC and/or ADCC than a corresponding IgG1 or IgG3 antibody having the same variable regions. Assays for measuring CDC or ADCC activity are well known in the art.

In one embodiment thereof the stabilized IgG4 antibody is selected from the group consisting of a human monoclonal antibody, a humanized monoclonal antibody and a chimeric monoclonal antibody.

In one embodiment thereof the stabilized IgG4 antibody comprises a human kappa light chain.

In one embodiment thereof the stabilized IgG4 antibody comprises a human lambda light chain.

In one embodiment thereof the stabilized IgG4 antibody is a bivalent antibody, for example an antibody which is bivalent even in the presence of excess of irrelevant antibodies, as explained in the Examples herein.

In one embodiment thereof the stabilized IgG4 antibody is a full-length antibody.

Methods for the production of stabilized IgG4 antibodies are well-known in the art. In a preferred embodiment, antibodies of the invention are monoclonal antibodies. Monoclonal antibodies may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

Further modifications, such as amino acid substitutions, deletions or insertion as described above, may be performed using standard recombinant DNA techniques well-known in the art.

In one embodiment, the stabilized IgG4 antibody of the invention is a human antibody.

In a further main aspect, the invention relates to a method for producing a stabilized IgG4 antibody of the invention, said method comprising expressing a nucleic acid construct encoding said antibody in a host cell and optionally purifying said antibody.

In one embodiment, the stabilized IgG4 antibody of the invention is linked to a compound selected from the group consisting of a cytotoxic agent; a radioisotope; a prodrug or drug, such as a taxane; a cytokine; and a chemokine. Methods for linking (conjugating) such compounds to an antibody are well-known in the art. References to suitable methods have been given in WO 2004/056847 (Genmab).

In one embodiment thereof the stabilized IgG4 antibody is linked to a compound selected from the group consisting of a cytotoxic agent; a radioisotope; a prodrug or drug, such as a taxane; a cytokine; and a chemokine.

In a further main aspect, the invention relates to a pharmaceutical composition comprising a stabilized IgG4 antibody as defined herein above. The pharmaceutical compositions may be formulated with pharmaceutically acceptable carriers or diluents as well as any other known adjuvants and excipients in accordance with conventional techniques, such as those disclosed in Remington: The Science and Practice of Pharmacy, 19th Edition, Gennaro, Ed., Mack Publishing Co., Easton, Pa., 1995.

In one embodiment, a pharmaceutical composition of the present invention is administered parenterally. The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

The stabilized IgG4 antibodies of the invention can be used in the treatment and/or prevention of a number of diseases, and be directed to an antigen selected from a broad variety of suitable target molecules.

In one embodiment thereof the stabilized IgG4 antibody according to any one of the above embodiments binds to an antigen selected from the group consisting of erythropoietin, beta-amyloid, thrombopoietin, interferon-alpha (2a and 2b), interferon-beta (1b), interferon-gamma, TNFR I (CD120a), TNFR II (CD120b), IL-1R type 1 (CD121a), IL-1R type 2 (CD121b), IL-2, IL2R (CD25), IL-2R-beta (CD123), IL-3, IL-4, IL-3R (CD123), IL-4R (CD124), IL-5R (CD125), IL-6R-alpha (CD126), -beta (CD130), IL-8, IL-10, IL-11, IL-15, IL-15BP, IL-15R, IL-20, IL-21, TCR variable chain, RANK, RANK-L, CTLA4, CXCR4R, CCR5R, TGF-beta1, -beta2, -beta3, G-CSF, GM-CSF, MIF-R (CD74), M-CSF-R (CD115), GM-CSFR (CD116), soluble FcRI, sFcRII, sFcRIII, FcRn, Factor VII, Factor VIII, Factor IX, VEGF, VEGFxxxb, alpha-4 integrin, Cd11a, CD18, CD20, CD38, CD25, CD74, FcalphaRI, FcepsilonRI, acetyl choline receptor, fas, fasL, TRAIL, hepatitis virus, hepatitis C virus, envelope E2 of hepatitis C virus, tissue factor, a complex of tissue factor and Factor VII, EGFr, CD4, CD28, VLA-1, 2, 3, or 4, LFA-1, MAC-1, I-selectin, PSGL-1, ICAM-I, P-selectin, periostin, CD33 (Siglec 3), Siglec 8, TNF, CCL1, CCL2, CCL3, CCL4, CCL5, CCL11, CCL13, CCL17, CCL18, CCL20, CCL22, CCL26, CCL27, CX3CL1, LIGHT, EGF, VEGF, TGFalpha, HGF, PDGF, NGF, complement or a related components such as: C1q, C4, C2, C3, C5, C6, C7, C8, C9, MBL, factor B, a Matrix Metallo Protease such as any of MMP1 to MMP28, CD32b, CD200, CD200R, Killer Immunoglobulin-Like Receptors (KIRs), NKG2D and related molecules, leukocyte-associated immunoglobulin-like receptors (LAIRs), ly49, PD-L2, CD26, BST-2, ML-IAP (melanoma inhibitor of apoptosis protein), cathepsin D, CD40, CD40R, CD86, a B cell receptor, CD79, PD-1 and a T cell receptor.

In one embodiment thereof
(i) the antibody binds to an alpha-4 integrin and is for use in the treatment of inflammatory and autoimmune diseases, such as rheumatoid arthritis, multiple sclerosis, inflammatory bowel disease, asthma and sepsis;
(ii) the antibody binds to VLA-1, 2, 3, or 4 and is for use in the treatment of inflammatory and autoimmune diseases, such as rheumatoid arthritis, multiple sclerosis, inflammatory bowel disease, asthma, type-1 diabetes, SLE, psoriasis, atopic dermatitis, COPD and sepsis;
(iii) the antibody binds to a molecule selected from the group consisting of LFA-1, MAC-1, I-selectin and PSGL-1 and is for use in the treatment of inflammatory and autoimmune diseases, such as rheumatoid arthritis, multiple sclerosis, inflammatory bowel disease, asthma, type-1 diabetes, SLE, psoriasis, atopic dermatitis, and COPD;
(iv) the antibody binds to a molecule selected from the group consisting of LFA-1, MAC-1, 1-selectin and PSGL-1 and is for use in the treatment of a disease selected from the group consisting of ischemia-reperfusion injury, cystic fibrosis, osteomyelitis, glomerulonepritis, gout and sepsis;
(v) the antibody binds to CD18 and is for use in the treatment of inflammatory and autoimmune diseases, such as rheumatoid arthritis, multiple sclerosis, inflammatory bowel disease, asthma, type-1 diabetes, SLE, psoriasis, atopic dermatitis and COPD;
(vi) the antibody binds to Cd11a and is for use in the treatment of inflammatory and autoimmune diseases, such as rheumatoid arthritis, multiple sclerosis, inflammatory bowel disease, asthma, type-1 diabetes, SLE, psoriasis, atopic dermatitis and COPD;
(vii) the antibody binds ICAM-1 and is for use in the treatment of inflammatory and autoimmune diseases, such as rheumatoid arthritis, multiple sclerosis, inflammatory bowel disease, asthma, type-1 diabetes, SLE, psoriasis, atopic dermatitis and COPD;
(viii) the antibody binds to P-selectin and is for use in the treatment of cardiovascular diseases, post-thrombotic vein wall fibrosis, ischemia reperfusion injury, inflammatory diseases or sepsis;
(ix) the antibody binds to periostin and is for use in the treatment of malignant diseases and/or metastasizing diseases, such as ovary cancer, endometrial cancer, NSCLC, glioblastoma, brain-related tumors, breast cancer, OSCC, colon cancer, pancreatic cancer, HNSCC, kidney cancer, thymoma, lung cancer, skin cancer, larynx cancer, liver cancer, parotid tumors, gastric cancer, esophagus cancer, prostate cancer, bladder cancer and cancer of the testis;
(x) the antibody binds to CD33 (Siglec 3), is optionally coupled to a toxin, cytotoxic or cytostatic drug, and is for use in the treatment of tumors expressing CD33 or acute myeloid leukemia;
(xi) the antibody binds to Siglec 8 and is for use in the treatment of asthma, inflammatory or autoimmune diseases, such as rheumatoid arthritis, multiple sclerosis, inflammatory bowel disease, asthma, type-1 diabetes, SLE, psoriasis, atopic dermatitis and COPD;
(xii) the antibody binds to TNF and is for use in the treatment of inflammatory and autoimmune diseases, such as rheumatoid arthritis, multiple sclerosis, inflammatory bowel disease, asthma, type-1 diabetes, SLE, psoriasis, atopic dermatitis, COPD and sepsis;
(xiii) the antibody binds to CCL1, CCL2, CCL3, CCL4, CCL5, CCL11, CCL13, CCL17, CCL18, CCL20, CCL22, CCL26, CCL27 or CX3CL1 and is for use in the treatment of atopic dermatitis, inflammatory and autoimmune diseases, such as rheumatoid arthritis, multiple sclerosis, inflammatory bowel disease, asthma, type-1 diabetes, SLE, psoriasis, COPD and sepsis;
(xiv) the antibody binds to LIGHT and is for use in the treatment of a disease selected from the group consisting of: hepatitis, inflammatory bowel disease, GVHD and inflammation;
(xv) the antibody binds to EGF, VEGF, TGFalpha or HGF and is for use in the treatment of: malignant diseases, such as solid cancers;

(xvi) the antibody binds to PDGF and is for use in the treatment of diseases in which abnormal cell proliferation cell migration and/or angiogenesis occurs, such as atherosclerosis, fibrosis, and malignant diseases;

(xvii) the antibody binds to NGF and is for use in the treatment of neurological diseases, neurodegenerative diseases, such as Alzheimer's disease and Parkinson's disease, or cancer, such as prostate cancer;

(xviii) the antibody binds to complement or a related components such as C1q, C4, C2, C3, C5, C6, C7, C8, C9, MBL, or factor B and is for use in diseases in which complement and related components play a detrimental role, such as organ transplant rejection, multiple sclerosis, Guillain-Barré syndrome, hemolytic anemia, Paroxysmal Nocturnal Hemoglobinuria, stroke, heart attacks, burn injuries, age-related macular degeneration, asthma, lupus, arthritis, myasthenia gravis, anti-phospholipid syndrome, sepsis and ischemia reperfusion injury;

(xix) the antibody binds to a Matrix Metallo Protease such as any of MMP1 to MMP28 and is for use in the treatment of inflammatory and autoimmune diseases, cancer, including metastatic cancer; arthritis, inflammation, cardiovascular diseases, cerebrovascular diseases such as stroke or cerebral aneurysms, pulmonary diseases such as asthma, ocular diseases such as corneal wound healing or degenerative genetic eye diseases, gastrointestinal diseases such as inflammatory bowel disease or ulcers, oral diseases such as dental caries, oral cancer or periodontitis, ischemia reperfusion injury or sepsis;

(xx) the antibody binds to CD32b and is for use in enhancement of T-cell responses to tumor antigens and ADCC/phagocytosis by macrophages, in combination with another therapeutic antibody; vaccination, immunotherapy of B-cell lymphoma's, asthma or allergy;

(xxi) the antibody binds to CD200 or CD200R and is for use in the treatment of: asthma, rheumatoid arthritis, GVHD, other autoimmune diseases, or cancer, such as solid tumors or lymphomas;

(xxii) the antibody binds to Killer Immunoglobulin-Like Receptors (KIRs), NKG2D or related molecules, leukocyte-associated immunoglobulin-like receptors (LAIRs), or ly49 and is for use in the treatment of: cancer, such as solid tumors or lymphomas; asthma, rheumatoid arthritis, GVHD or other autoimmune diseases;

(xxiii) the antibody binds to PD-L2 and is for use in the treatment of cancer, asthma, or for use in vaccine enhancement;

(xxiv) the antibody binds to CD26 and is for use in the treatment of: atherosclerosis, GVHD, or auto-immune diseases;

(xxv) the antibody binds to BST-2 and is for use in the treatment of asthma, atherosclerosis, rheumatoid arthritis, psoriasis, Crohn's disease, ulcerative cholitis, atopic dermatitis, sepsis or inflammation;

(xxvi) the antibody binds to ML-IAP (melanoma inhibitor of apoptosis protein) and is for use in the treatment of melanoma;

(xxvii) the antibody binds to cathepsin D and is for use in the treatment of malignant diseases such as breast cancer, ovarian cancer, glioma, NSCLC, bladder cancer, endometrial cancer, liver cancer, sarcoma, gastric cancer, SCCHN, prostate cancer or colorectal cancer;

(xxviii) the antibody binds to CD40 or CD40R and is for use in the treatment of cancer, in particular B-cell lymphomas, B-cell-related or -mediated diseases, autoimmune diseases such as psoriatic arthritis, rheumatoid arthritis, multiple sclerosis, psoriasis, Crohn's disease or ulcerative cholitis;

(xxix) the antibody binds to CD86 and is for use in conjunction with organ transplantation;

(xxx) the antibody binds to a B cell receptor and is for use in the treatment of: B-cell-related or -mediated diseases, such as B cell lymphoma's, leukemia, autoimmune diseases, inflammation or allergy;

(xxxi) the antibody binds to CD79 and is for use in the treatment of B-cell-related or -mediated diseases, such as B-cell lymphomas, leukemia, autoimmune diseases, inflammation or allergy;

(xxxii) the antibody binds to a T cell receptor and is for use in the treatment of T-cell-related or -mediated diseases, such as T-cell lymphomas, leukemia, autoimmune diseases, inflammation or allergy;

(xxxiii) the antibody binds to FcalphaRI and is for use in the treatment of a disease or disorder selected from allergic asthma or other allergic diseases such as allergic rhinitis, seasonal/perennial allergies, hay fever, nasal allergies, atopic dermatitis, eczema, hives, urticaria, contact allergies, allergic conjunctivitis, ocular allergies, food and drug allergies, latex allergies, or insect allergies, or IgA nephropathy, such as IgA pemphigus;

(xxxiv) the antibody binds to CD25 and is for use in the treatment of a disease or disorder selected from the group consisting of transplant rejection, graft-versus-host disease, inflammatory, immune or autoimmune diseases, inflammatory or hyperproliferative skin disorders, lymphoid neoplasms, malignancies, hematological disorders, skin disorders, hepato-gastrointestinal disorders, cardiac disorders, vascular disorders, renal disorders, pulmonary disorders, neurological disorders, connective tissue disorders, endocrinological disorders, and viral infections;

(xxxv) the antibody binds to IL-15 or the IL15 receptor and is for use in the treatment of a disease or disorder selected from the group consisting of: arthritides, gout, connective disorders, neurological disorders, gastrointestinal disorders, hepatic disorders, allergic disorders, hematologic disorders, skin disorders, pulmonary disorders, malignant disorders, endocrinological disorders, vascular disorders, infectious disorders, kidney disorders, cardiac disorders, circulatory disorders, metabolic disorders, bone, disorders and muscle disorders;

(xxxvi) the antibody binds to IL-8 and is for use in the treatment of a disease or disorder selected from the group consisting of palmoplantar pustulosis (PPP), psoriasis, or other skin diseases, inflammatory, autoimmune and immune disorders, alcoholic hepatitis and acute pancreatitis, diseases involving IL-8 mediated angiogenesis;

(xxxvii) the antibody binds to CD20 and is for use in the treatment of a disease or disorder selected from the group consisting of: rheumatoid arthritis, (auto)immune and inflammatory disorders, non-Hodgkin's lymphoma, B-CLL, lymphoid neoplasms, malignancies and hematological disorders, infectious diseases and connective disorders, neurological disorders, gastrointestinal disorders, hepatic disorders, allergic disorders, hematologic disorders, skin disorders, pulmonary disorders, malignant disorders, endocrinological disorders, vascular disorders, infectious disorders, kidney disorders, cardiac disorders, circulatory disorders, metabolic disorders, bone and muscle disorders, and immune mediated cytopenia;

(xxxviii) the antibody binds to CD38 and is for use in the treatment of a disease or disorder selected from the group consisting of tumorigenic disorders, immune disorders in which CD38 expressing B cells, plasma cells, monocytes and T cells are involved, acute respiratory distress syndrome and choreoretinitis, rheumatoid arthritis, inflammatory, immune and/or autoimmune disorders in which autoantibodies and/or excessive B and T lymphocyte activity are prominent, skin disorders, immune-mediated cytopenias, connective tissue disorders, arthritides, hematologic disorders, endocrinopathies, hepato-gastrointestinal disorders, nephropathies, neurological disorders, cardiac and pulmonary disorders, allergic disorders, ophthalmologic disorders, infectious diseases, gynecological-obstetrical disorders, male reproductive disorders, transplantation-derived disorders;

(xxxix) the antibody binds to EGFr and is for use in the treatment of a disease or disorder selected from the group consisting of: cancers (over)expressing EGFr and other EGFr related diseases, such as autoimmune diseases, psoriasis, and inflammatory arthritis;

(xxxx) the antibody binds to CD4 and is for use in the treatment of a disease or disorder selected from the group consisting of rheumatoid arthritis, (auto)immune and inflammatory disorders, cutaneous T cell lymphomas, non-cutaneous T cell lymphomas, lymphoid neoplasms, malignancies and hematological disorders, infectious diseases, and connective disorders, neurological disorders, gastrointestinal disorders, hepatic disorders, allergic disorders, hematologic disorders, skin disorders, pulmonary disorders, malignant disorders, endocrinological disorders, vascular disorders, infectious disorders, kidney disorders, cardiac disorders, circulatory disorders, metabolic disorders, bone disorders, muscle disorders, immune mediated cytopenia, and HIV infection/AIDS;

(xxxxi) the antibody binds CD28 and is for use in the treatment of a disease or disorder selected from the group consisting of an inflammatory disease, autoimmune disease and immune disorder;

(xxxxii) the antibody binds to tissue factor, or a complex of Factor VII and tissue factor and is for use in the treatment of a disease or disorder selected from the group consisting of vascular diseases, such as myocardial vascular disease, cerebral vascular disease, retinopathy and macular degeneration, and inflammatory disorders; or (xxxxiii) the antibody binds to PD-1 and is for use in the treatment of HIV-1/AIDS.

In a further embodiment the invention relates to a pharmaceutical composition, characterized in that it comprises a stabilized IgG4 antibody as defined in any one of the above embodiments and a pharmaceutically acceptable carrier or excipient.

In a further embodiment the invention relates to the use of a stabilized IgG4 antibody according to any one of the above embodiments (i) to (xxxxiii) for the preparation of a medicament for the treatment of a disease as specified in any one of the above related embodiments (i) to (xxxxiii).

In a further embodiment the invention relates to a method for the treatment of a subject suffering from a disease as specified in any one of the above embodiments (i) to (xxxxiii) comprising administering to the subject in need thereof a stabilized IgG4 antibody according to as specified in any one of the above related embodiments (i) to (xxxxiii).

The present invention is further illustrated by the following examples which should not be construed as further limiting.

EXAMPLES

Example 1

Structural Analysis of CH3-CH3 Interface

In human IgG1, the non-covalent interaction between the CH3 domains involves 16 residues located on four anti-parallel δ-strands that make intermolecular contacts and burry 1090 $Å^2$ from each surface (Deisenhofer, J.; Biochemistry, 1981. 20(9): p. 2361-70). Alanine scanning mutagenesis showed that stabilization of the IgG1 CH3-CH3 interaction was largely mediated by 6 of these residues, including K409 (Dall'Acqua, W., et al.; Biochemistry, 1998. 37(26): p. 9266-73). To get a better understanding of the role of K409 in the IgG1 CH3-CH3 interaction, the 1.65 Å 1L6X crystal structure (Idusogie, E. E., et al.; J Immunol, 2000. 164(8): p. 4178-84) was studied in more detail using the Brugel modelling package (Delhaise, P., et al., J. Mol. Graph., 1984. 2(4): p. 103-106).

In order to propose mutations that should lead to a desired stabilization (or destabilization) of IgG4, a quantitative structure-based scoring methodology was employed (Desmet, J., et al., Proteins, 2005. 58(1): p. 53-69). Briefly, each position in the CH3-CH3 dimer interface was subjected to mutagenesis to all natural amino acids, except cysteine and proline. Subsequent to mutagenesis, Exploration of the conformational space was obtained by interdependent optimization of the side chains of all residues located in a sphere of 12 Å of the mutated residue, using the FASTER algorithm (Desmet, J., et al., Proteins, 2002. 48(1): p. 31-43), performed on all macro-rotameric states for the side chain under investigation. Subsequently, on each macro-rotameric state thus obtained, a scoring function for the side chain under investigation was evaluated, as described (Desmet, J., et al., Proteins, 2005. 58(1): p. 53-69). Finally, per position in the CH3-CH3 dimer interface, the highest scores for each mutation were compared, and visual inspection of the resulting conformation was carried out in selected cases.

Example 2

Water Hypothesis

In the IgG1 structure, K409 forms a hydrogen bond with D399' on the opposite CH3 domain. Furthermore, K409 is part of a water-binding pocket together with S364 and T411 in the same CH3 domain and K370' on the opposite CH3 domain. The presence of the water molecule prevents an electrostatic clash between K409 and K370'.

The K409R substitution (as in IgG4) was modelled in the 1L6X structure by optimizing the side chain conformations of the arginine residue and its surrounding residues, using the FASTER algorithm (Desmet, J., et al., Proteins, 2002. 48(1): p. 31-43). In this model, the guanidinium group of R409 takes up the position of the water molecule and causes an electrostatic clash with K370'. The side-chains of T411 and K370' loose their interactions compared to the case with water present (as in IgG1), but D399 keeps its interaction with the side chain at position R409.

Example 3

Destabilization of IgG4

The mutations in the Table below were made in order to destabilize the CH3-CH3 interaction of an IgG4.

KABAT indicates amino acid numbering according to Kabat (Kabat et al., Sequences of Proteins of Immunological Interest, 5th Ed. Public Health Service, National Institutes of Health, Bethesda, Md. (1991). EU index indicates amino acid numbering according to EU index as outlined in Kabat et al., Sequences of Proteins of Immunological Interest, 5th Ed. Public Health Service, National Institutes of Health, Bethesda, Md. (1991)).

| Numbering of CH3 mutations | | |
|---|---|---|
| KABAT | EU index G4 | SEQ ID NO: 4 |
| 370 | Y349R* | Y217R* |
| 372 | L351N* | L219N* |
| 372 | L351Q* | L219Q* |
| 378 | E357A | E225A |
| 378 | E357T* | E225T* |
| 378 | E357V* | E225V* |
| 378 | E357I* | E225I* |
| 387 | S364R* | S232R* |
| 387 | S364K* | S232K* |
| 389 | T366A | T234A |
| 389 | T366R* | T234R* |
| 389 | T366K* | T234K* |
| 389 | T366N* | T234N* |
| 391 | L368A | L236A |
| 391 | L368V | L236V |
| 391 | L368E* | L236E* |
| 391 | L368G* | L236G* |
| 391 | L368S* | L236S* |
| 391 | L368T* | L236T* |
| 393 | K370A | K238A |
| 393 | K370R* | K238R* |
| 393 | K370T | K238T |
| 427 | D399A | D267A |
| 427 | D399T* | D267T* |
| 427 | D399S* | D267S* |
| 436 | F405A | F273A |
| 436 | F405L | F273L |
| 436 | F405T* | F273T* |
| 436 | F405D* | F273D* |
| 436 | F405R* | F273R* |
| 436 | F405Q* | F273Q* |
| 436 | F405K* | F273K* |
| 436 | F405Y | F273Y |
| 438 | Y407A | Y275A |
| 438 | Y407E* | Y275E* |
| 438 | Y407Q* | Y275Q* |
| 438 | Y407K* | Y275K* |
| 438 | Y407F | Y275F |
| 440 | R409A | R277A |
| 440 | R409K | R277K (stabilizing see WO2008145142) |
| 440 | R409E* | R277E* |
| 442 | T411D* | T279D* |
| 442 | T411V* | T279V* |
| 442 | T411N* | T279N* |

Example 4

Various Technical Procedures

The following techniques were performed as described in WO2007059782: Oligonucleotide primers and PCR amplification, agarose gel electrophoresis, analysis and purification of PCR products and enzymatic digestion products, quantification of DNA by UV spectroscopy, restriction enzyme digestions, ligation of DNA fragments, transformation of *E. coli*, screening of bacterial colonies by PCR, plasmid DNA isolation from *E. coli* culture, site-directed mutagenesis, DNA sequencing and transient expression in HEK-293F cells.

Example 5

Constructions and Biochemical Analysis of CH3 Variants of 2F8-HG

The above-described mutations were introduced into the CH3 region of hingeless anti-EGFR antibody 2F8-HG, described in WO2007059782. To make the constructs for the expression of the CH3 mutants, the mutations were introduced into pTomG42F8HG (described in WO2007059782) using site-directed mutagenesis. The constructs were expressed transiently and purified as described in WO2007059782.

In order to investigate whether CH3 variant HG molecules exist as monomers or dimers, a mass spectrometry method was employed as described in WO2007059782.

FIG. 1 shows a summary of the monomer/dimer ratios obtained for each HG mutant using non-covalent nano-electrospray mass spectrometry. CH3 mutants showed a substantial increase in monomer/dimer ratio compared to 2F8-HG (WT). The percentage molecules present as monomers increased from 15% in 2F8-HG (WT) to >80% in most CH3 mutants, except for mutation R277A. HG mutation R277K, which introduces an IgG1 sequence into the IgG4 backbone, was used as negative control. As expected, this mutant behaved as dimer.

Figure 2:
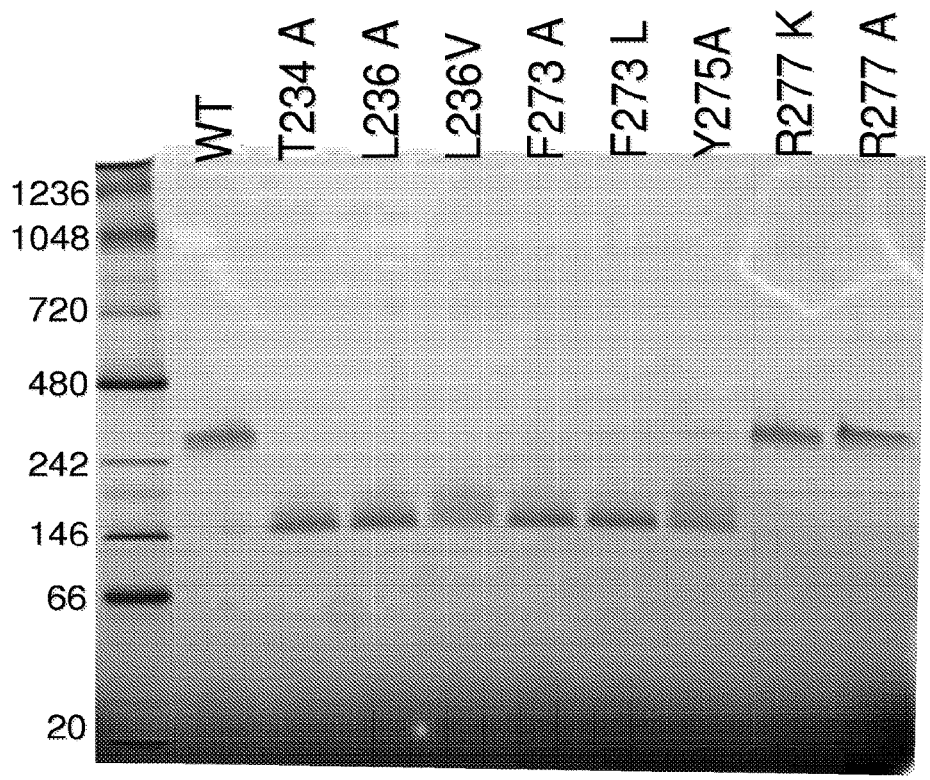
FIG. 2: NativePAGE™ Novex® Bis-Tris gel electrophoresis of CH3 mutants compared to 2F8-HG (WT) and R277K HG mutant control.

The monomer or dimer configuration of CH3 mutants was verified using NativePAGE™ Novex® Bis-Tris gel electrophoresis (Invitrogen, Carlsbad, Calif.) according to the instructions of the manufacturer as shown in FIG. 2. This native gel electrophoresis technique uses Coomassie G-250 as a charge-shift molecule instead of SDS and is able to maintain native protein conformation and protein complex quaternary structures (Schagger H and von Jagow G 1991 Blue native gel electrophoresis for isolation of membrane complexes in enzymatically active form. Anal. Biochem. 199:223-244).

Under these experimental conditions, 2F8-HG (WT) and R277K and R277A showed a protein band corresponding to the size of a full tetrameric (two heavy and two light chains) molecule. The CH3 mutants T234A, L236A, L236V, F273A, F273L, and Y275A were shown to be half molecules (only one heavy and one light chain).

Example 6

Functional Analysis of CH3 Mutants of 2F8-HG

Binding of 2F8-HG (WT) and variants was determined in the absence and presence of 200 µg/ml polyclonal human IgG (Intravenous Immunoglobulin, IVIG, Sanquin Netherlands) (as described in Example 57 of WO2007059782).

Figure 3:
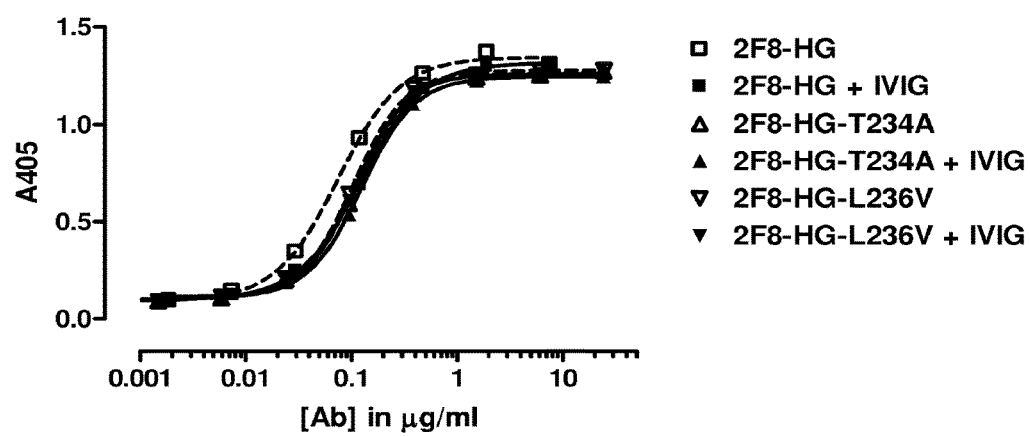
FIG. 3: The binding of 2F8-HG and CH3 variants 2F8-HG-T234A and 2F8-HG-L236V was tested in EGFR ELISA in the presence and absence of polyclonal human IgG.
Figure 4:
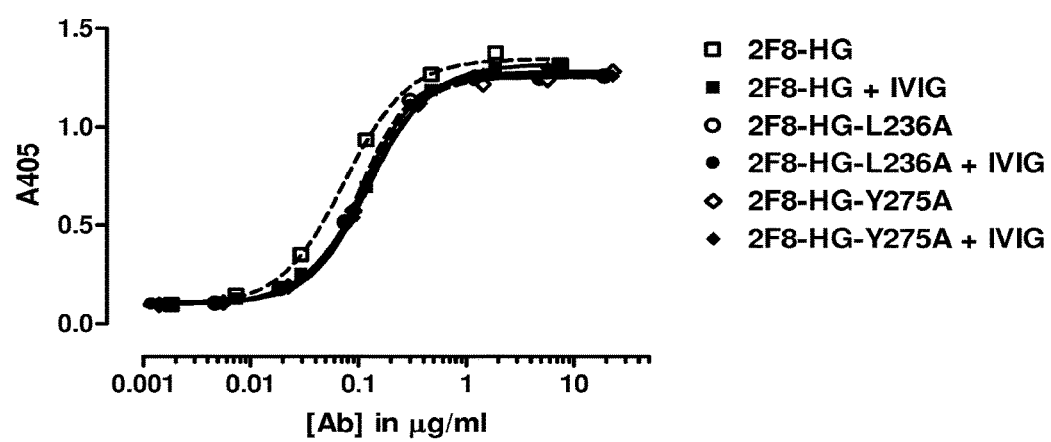
FIG. 4: The binding of 2F8-HG and CH3 variants 2F8-HG-L236A and 2F8-HG-Y275A was tested in EGFR ELISA in the presence and absence of polyclonal human IgG.

FIGS. 3 and 4 show that the binding curve of 2F8-HG in the presence of IVIG clearly right-shifts with respect to the binding curve of 2F8-HG without IVIG. This difference in avidity for the EGFr coat is consistent with the idea that, in the presence of IVIG, 2F8-HG binds monovalently (see Example 57 of WO2007059782). The binding curves of several of the tested mutations, 2F8-HG-T234A, 2F8-HG-L236V, 2F8-HG-L236A and 2F8-HG-Y275A, become insensitive to the addition of IVIG and were super-imposable on the monovalent binding curve of 2F8-HG in the presence of IVIG. These differences in avidity for the EGFr coat are consistent with the idea that the 2F8-HG-T234A, 2F8-HG-L236V, 2F8-HG-L236A and 2F8-HG-Y275A mutations prevent dimerization of the HG molecules.

Example 7

Functional Analysis of CH3 Mutants of 2F8-HG

CH3 mutants of 2F8-HG were shown to bind EGFr with lower apparent affinities than 2F8-HG in a binding ELISA coated with EGFr protein (see above). The potency of 2F8-HG CH3 mutants to inhibit ligand-induced EGFr phosphorylation in cells in vitro was compared to that of 2F8-HG (WT) and 2F8-Fab fragments in the Phosphorylation Inhibition Assay (PIA) as described in example 54 of WO2007059782.

Figure 5:
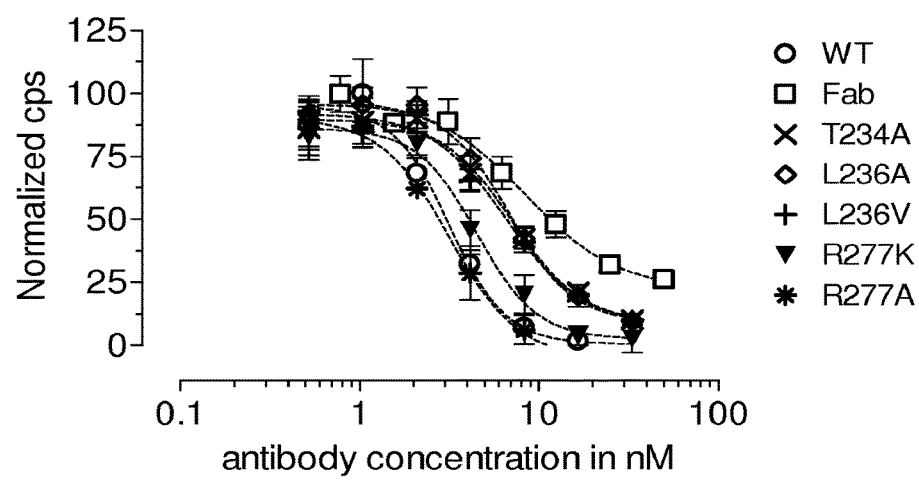
FIG. 5: Dose-response curves showing the inhibition of EGF-induced EGFr phosphorylation in A431 cells by anti-EGFr 2F8-HG (WT) and CH3 mutants thereof.
Figure 5:
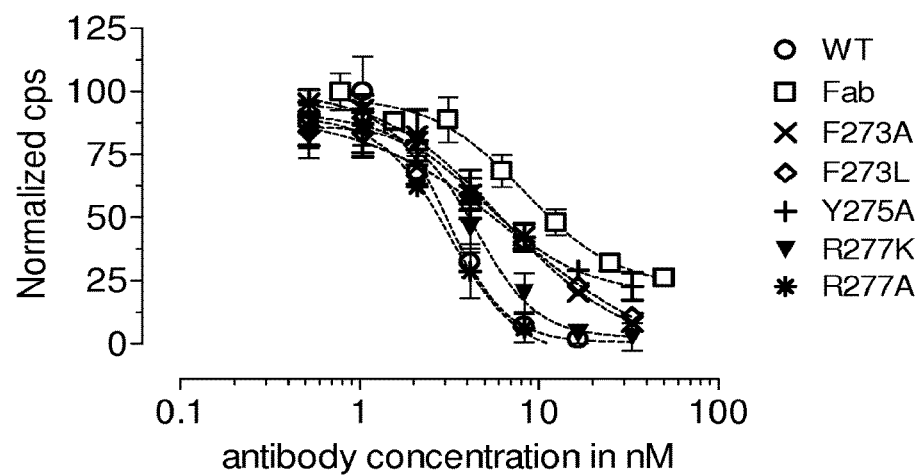

CH3 HG mutants were less potent to inhibit EGFr phosphorylation than 2F8-HG (WT) and the control mutants R277K and R277A, in line with the increase in monomer/dimer ratio of these mutants (FIG. 5).

Example 8

Concentration Dependent Configuration of CH3 Mutants of HG

The monomer/dimer configuration of CH3 mutants F273A, L236V, and Y275A was further investigated at different concentrations, ranging from 0.01-10 µM using non-covalent nano-electrospray mass spectrometry as described in WO2007059782. The monomer/dimer configuration of these CH3 mutants was compared to the configuration of 2F8-HG (WT) and R277K.

Figure 6:
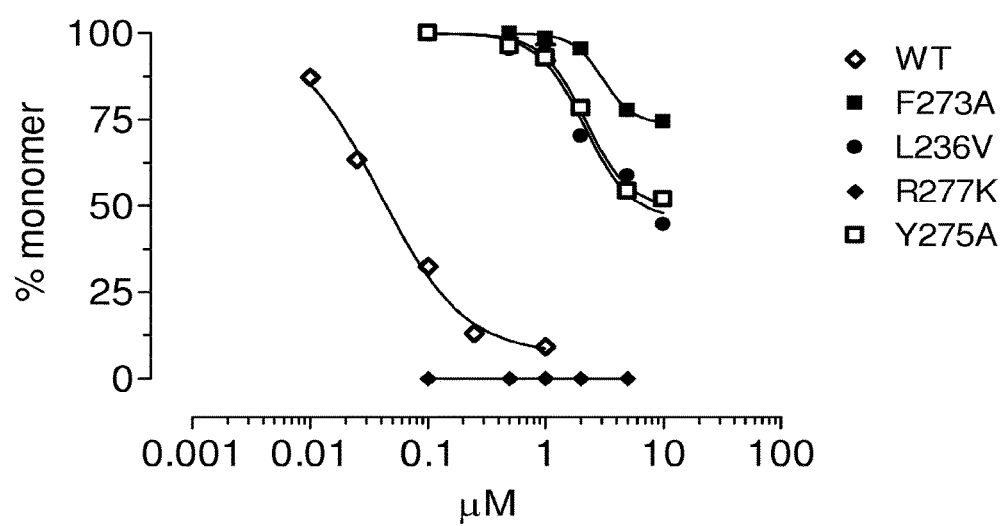
FIG. 6: Percentage molecules present as monomers at different molar concentrations of CH3 mutants compared to 2F8-HG (WT) and R277K.

FIG. 6 shows that all HG mutants were 100% monomeric at low concentrations (except for R277K which behaved as dimer). With increased concentration of HG mutants, a decrease in monomericity was observed. However, the figure shows that the CH3 mutants exhibited such decrease in monomericity at much higher concentration than 2F8-HG (WT). Hence, the CH3 mutants contained a higher percentage of monomer molecules at higher molar concentrations.

For 2F8-HG (WT) and mutants E225A, E225V, S232R, T234A, L236T, L236V, L236E, L236S, L236G, K238A, K238T, D267S, D267A, F273A, F273L, F273Y, F273D, F273T, F273R, F273Q, Y275A, Y275Q, Y275K, Y275E, R277A, R277K, D267S+Y275E, D267S+Y275K, D267S+Y275Q, F273D+Y275E and F273T+Y275E signals corresponding to the monomeric ($M_s$) and dimeric ($D_s$) configurations were integrated and the relative proportion of each configuration at each concentration ($[M]_0$) was determined using the following equations:

$[M]_{eq} = M_S/(M_S+D_S) \cdot [M]_0$; concentration monomer at equilibrium $[D]_{eq} = ([M]_0 - [M]_{eq})/2$; Concentration Dimer at Equilibrium Dissociation constant ($K_D$) values were subsequently calculated for all mutants by plotting the $[D]_{eq}$ against $[M]_{eq}^2$ values of each concentration and determining the gradient by least-squares linear regression using Excell software (Microsoft). The $K_D$ measured for 2F8-HG (WT) was $5.0 \times 10^{-8}$ M. The relative $K_D$ of each mutant compared to the $K_D$ of 2F8-HG (WT) was calculated and plotted.

Figure 7:
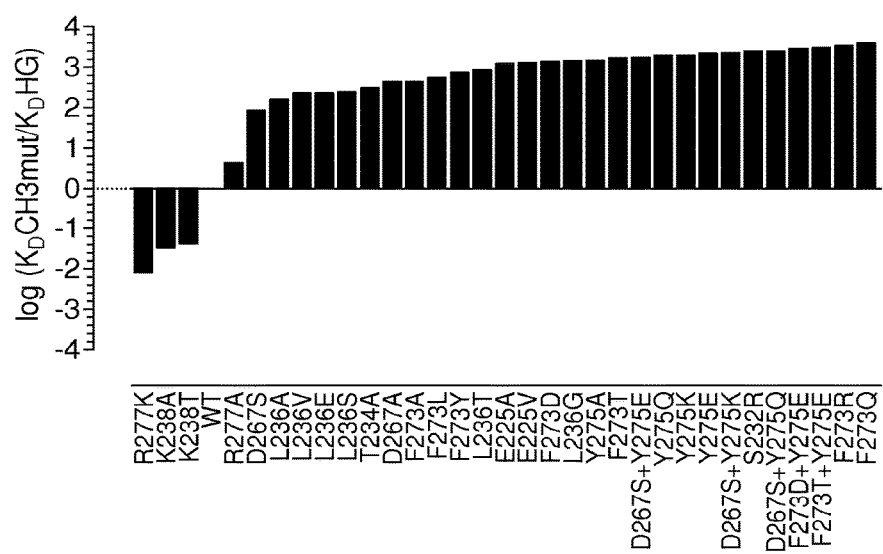
FIG. 7: Relative interaction strength (KD) of CH3 mutants compared to 2F8-HG (WT).

FIG. 7 shows that all HG mutants (except for R277K, K238A and K238T) had a higher relative $K_D$, which translates into an increase in monomeric behavior compared to 2F8-HG (WT). The R277K, K238A and K238T mutants showed a lower relative $K_D$, meaning that they stabilize the CH3-CH3 interaction.

Example 9

Removal of Glycosylation Sites

To remove (potential) acceptor sites for N-linked glycosylation ("glycosylation sites") from the monovalent antibody, alterations to the sequence were made. To examine how this could be achieved with introducing a minimum of T cell epitopes, and without perturbing the native structure of the molecule, an in silico analysis was performed. The HLA binding specificities of all possible 10-mer peptides derived from a target sequence were analyzed (Desmet et al. 1992, 1997, 2002, 2005; Van Walle et al. 2007 Expert Opinion on Biological Therapy 7:405-418). Profiling was done at the allotype level for 20 DRB1, 7 DRB3/4/5, 14 DQ and 7 DP, i.e. 48 HLA class II receptors in total. Quantitative estimates of the free energy of binding deltaGbind of a peptide for each of the 48 HLA class II receptors were calculated. These data were then further processed by classifying peptides as strong, medium, weak and non-binders.

The table below shows the 27 sequence variants which contain only medium epitopes, specific for no more than three different DRB1 allotypes.

TABLE

Summary of sequence variants containing either a single medium DRB1 epitope, or multiple medium epitopes affecting three or less MHC allotypes. The first column contains the specific sequence, the second column the number of medium DRB1 binding epitopes present in the sequence fragment, and the subsequent columns describe the specificity of these epitopes. Allotypes for which no epitopes were found in any of these sequence fragments were not included in the table.

| | DRB1M | DRB1*0101 | DRB1*0102 | DRB1*0401 | DRB1*0402 | DRB1*0405 | DRB1*0407 | DRB1*0801 |
|---|---|---|---|---|---|---|---|---|
| NST | 0 | | | | | | | |
| DST | 1 | | | | | | 1 | 1 |
| EST | 1 | | | | | | 1 | 1 |
| GST | 1 | | | | | | 1 | |
| HST | 1 | | | | | | 1 | 1 |
| MST | 1 | | | | | | 1 | |
| PST | 1 | | | | | | 1 | |
| QST | 1 | | | | | 1 | 1 | 1 |
| SST | 1 | | | | | | 1 | 1 |
| TST | 1 | | | | | | 1 | 1 |
| CSE | 2 | | 1 | 1 | | | | |
| CSP | 2 | | 1 | | | | 1 | |
| DSE | 2 | | 1 | 1 | | | | |
| DSG | 2 | 1 | 1 | | | | | |
| DSP | 2 | | 1 | | | | 1 | |
| ESE | 2 | | 1 | 1 | | 1 | | |
| ESP | 2 | | 1 | | | | 1 | |
| GSE | 2 | | 1 | 1 | | 1 | | |
| GSP | 2 | | 1 | | | | 1 | |
| HSE | 2 | | 1 | 1 | | | | |
| MSE | 2 | | 1 | 1 | | 1 | | |
| NSE | 2 | | 1 | 1 | | | | |
| NSP | 2 | | 1 | | | | 1 | |
| PSE | 2 | | 1 | 1 | | 1 | | |

TABLE-continued Summary of sequence variants containing either a single medium DRB1 epitope, or multiple medium epitopes affecting three or less MHC allotypes. The first column contains the specific sequence, the second column the number of medium DRB1 binding epitopes present in the sequence fragment, and the subsequent columns describe the specificity of these epitopes. Allotypes for which no epitopes were found in any of these sequence fragments were not included in the table.

| | | | | | | |
|---|---|---|---|---|---|---|
| PSP | 2 | 1 | | | | 1 |
| SSE | 2 | 1 | 1 | | | |
| SSP | 3 | 1 | | 1 | | 1 |
| TSP | 3 | 1 | | 1 | | 1 |

| | DRB1*0802 | DRB1*0901 | DRB1*1101 | DRB1*1104 | DRB1*1301 | DRB1*1401 |
|---|---|---|---|---|---|---|
| NST | | | | | | |
| DST | 1 | | | | | 1 |
| EST | | | | | | 1 |
| GST | | | | | | 1 |
| HST | 1 | | | | | 1 |
| MST | | | | | | 1 |
| PST | | | 1 | | | 1 |
| QST | 1 | 1 | 1 | 1 | | 1 |
| SST | | | | | | 1 |
| TST | | | 1 | 1 | | 1 |
| CSE | | | | | | |
| CSP | | | | | | 1 |
| DSE | | | | | | |
| DSG | | | | | 1 | |
| DSP | | | | | | |
| ESE | | | | | | |
| ESP | | | | | | |
| GSE | | | | | | |
| GSP | | | | | | |
| HSE | | | | | | |
| MSE | | | | | | |
| NSE | | | | | | |
| NSP | | 1 | | | | |
| PSE | | | | | | |
| PSP | | | | | | |
| SSE | | | | | | |
| SSP | | | | | | |
| TSP | | | | | | |

The lowest epitope content found in the study was within sequence variants which bind with medium strength to two different DRB1 allotypes (GST, MST, CSE, DSE, DSP, ESP, GSP, HSE, NSE, PSP and SSE). A negative selection for mutations that:

- substitute any positions to cysteine,
- change the final threonine to proline, or
- replace the initial asparagines residue by an aliphatic side chain, lead to the selection of the following preferred candidates: GST, NSE, DSE, HSE and SSE.

To make the constructs for the expression of deglycosylated 2F8-HG, the GST and NSE mutations as identified by the above-described analysis were introduced into pTomG42F8HG (described in WO 2007059782) using site-directed mutagenesis. The constructs were expressed transiently and binding was determined in the absence and presence of polyclonal human IgG (Intravenous Immunoglobulin, IVIG, Sanquin Netherlands) (as described in Example 57 of WO 2007059782).

Figure 8:
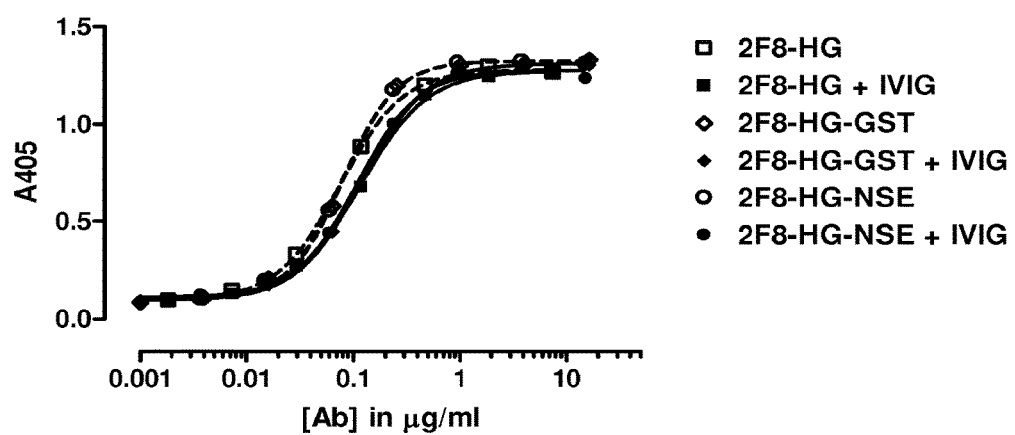
FIG. 8: The binding of 2F8-HG and deglycosylation variants 2F8-HG-GST and 2F8-HG-NSE was tested in EGFR ELISA in the presence and absence of polyclonal human IgG.

FIG. 8 shows that the binding curves of 2F8-HG-GST and 2F8-HG-NSE in the absence and presence of IVIG were identical to the binding curve of 2F8-HG in the absence and presence of IVIG, respectively. This is consistent with the hypothesis that deglycosylation does not effect the binding affinity of the HG-molecules or sensitivity to IVIG.

Example 10

Biochemical Analysis of Non-Glycosylation Mutants of 2F8-HG

Absence of glycosylation in the glycosylation site mutants of 2F8-HG was confirmed using High pH Anion Exchange Chromatography-Pulse Amperometric Detection (HPAEC-PAD).

To investigate the monomeric or dimeric configuration of the mutated HG molecules, a specialized mass spectrometry method was employed to preserve non-covalent interactions between molecules.

HG mutant samples were prepared in aqueous 50 mM ammonium acetate solutions and introduced into an LC-T nano-electrospray ionization orthogonal time-of-flight mass spectrometer (Micromass, Manchester, UK), operating in positive ion mode. Source pressure conditions in the LC-T mass spectrometer and nano-electrospray voltages were optimized for optimal transmission, the pressure in the interface region was adjusted by reducing the pumping capacity of the rotary pump by closing the valve (Pirani Pressure 6.67e0 mbar).

Spraying conditions were as follows: needle voltage 1275 V, cone voltage 200 V, and source temperature 80° C. Borosilicate glass capillaries (Kwik-Fil™, World Precision Instruments Inc., Sarasota, Fla.) were used on a P-97 puller (Sutter Instrument Co., Novato, Calif.) to prepare the nano-electrospray needles. They were subsequently coated with a thin gold layer using an Edwards Scancoat six Pirani 501 sputter coater (Edwards High Vacuum International, Crawley, UK).

Figure 9:
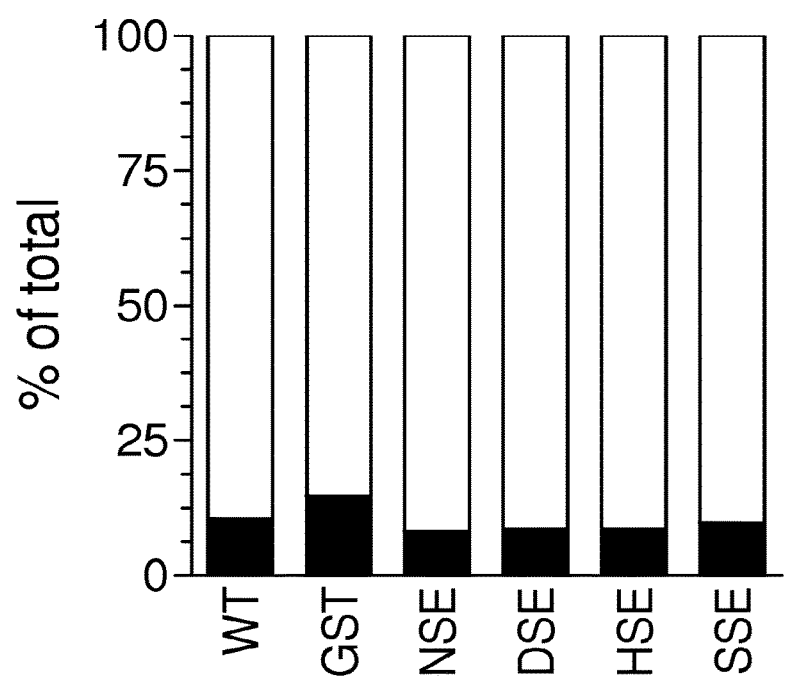
FIG. 9: Percentage of molecules present as monomers for each HG mutant measured using non-covalent nano-electrospray mass spectrometry. HG mutant samples were prepared in aqueous 50 mM ammonium acetate solutions at a concentration of 1 μM.

FIG. 9 shows a summary of the monomer/dimer ratios obtained for each HG mutant using non-covalent nano-electrospray mass spectrometry at 1 μM protein concentrations. In agreement with the observations described in Example 54 of WO2007059782, the data indicate that in the absence of polyclonal human IgG, 2F8-HG may behave as a bivalent antibody.

Under these experimental conditions, non-glycosylation mutants exhibited the same monomer/dimer ratio as 2F8-HG (WT).

Example 11

Functional Analysis of Non-Glycosylation Mutants of 2F8-HG

Figure 10:
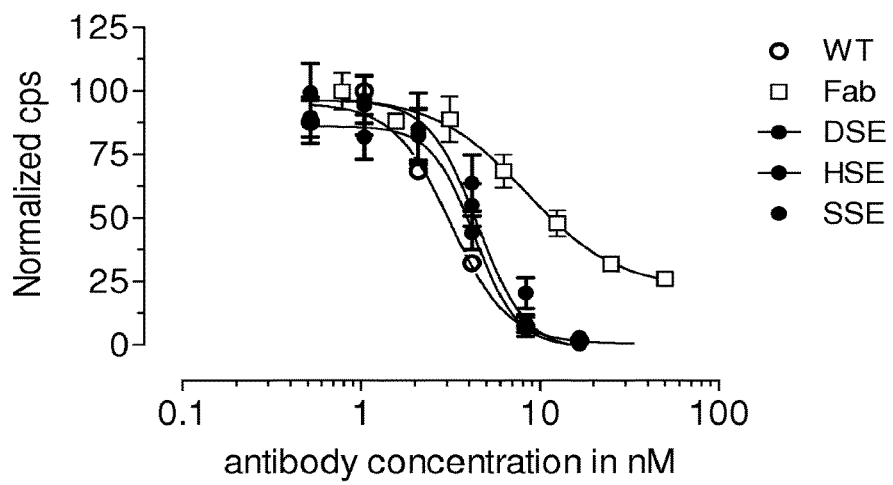
FIG. 10: Dose-response curves showing the inhibition of EGF-induced EGFr phosphorylation in A431 cells by anti-EGFr 2F8-HG (WT) and non-glycosylation mutants thereof.
Figure 10:
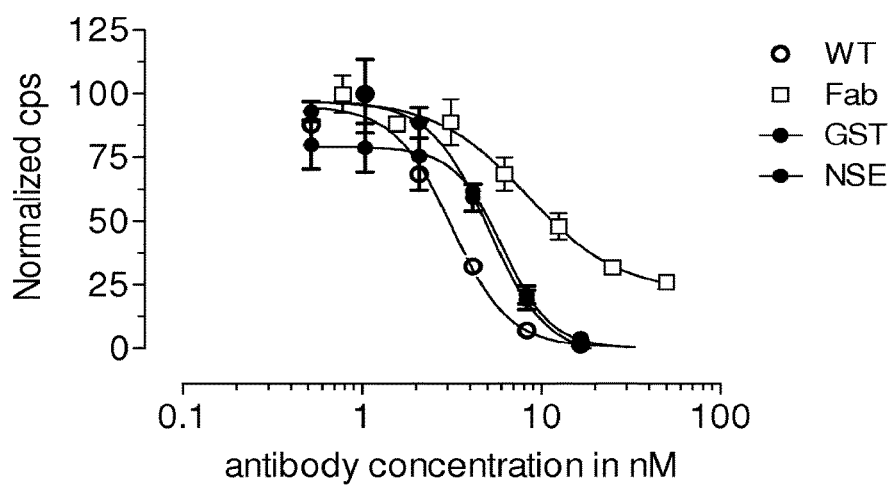

Non-glycosylation HG mutants 2F8-HG-GST, 2F8-HG-NSE, 2F8-HG-DSE, 2F8-HG-HSE, and 2F8-HG-SSE were shown to bind EGFr with apparent affinities similar to 2F8-HG (WT) in a binding ELISA, using EGFr protein as coat (see above). The potency of non-glycosylation 2F8-HG mutants to inhibit ligand-induced EGFr phosphorylation in cells in vitro was compared to that of 2F8-HG (WT) and 2F8-Fab fragments in the Phosphorylation Inhibition Assay (PIA) as described in example 54 of WO2007059782. FIG. 10 shows that the potency of non-glycosylation HG mutants to inhibit EGF-induced phosphorylation of EGFr in vitro was similar to that of 2F8-HG (WT).

Example 12

Pharmacokinetic Evaluation of Non-Glycosylation Mutants

Pharmacokinetic characteristics of non-glycosylation mutant 2F8-HG-GST and 2F8-HG-NSE were analyzed in SCID mice supplemented with 0.1 mg 7D8-IgG1 as internal control. Pharmacokinetic analysis is explained in detail in example 50 of WO2007059782. Internal control 7D8-IgG1 exhibited an equal clearance rate in all mice investigated and was comparable to the clearance rate of 2F8-IgG4.

Figure 11:
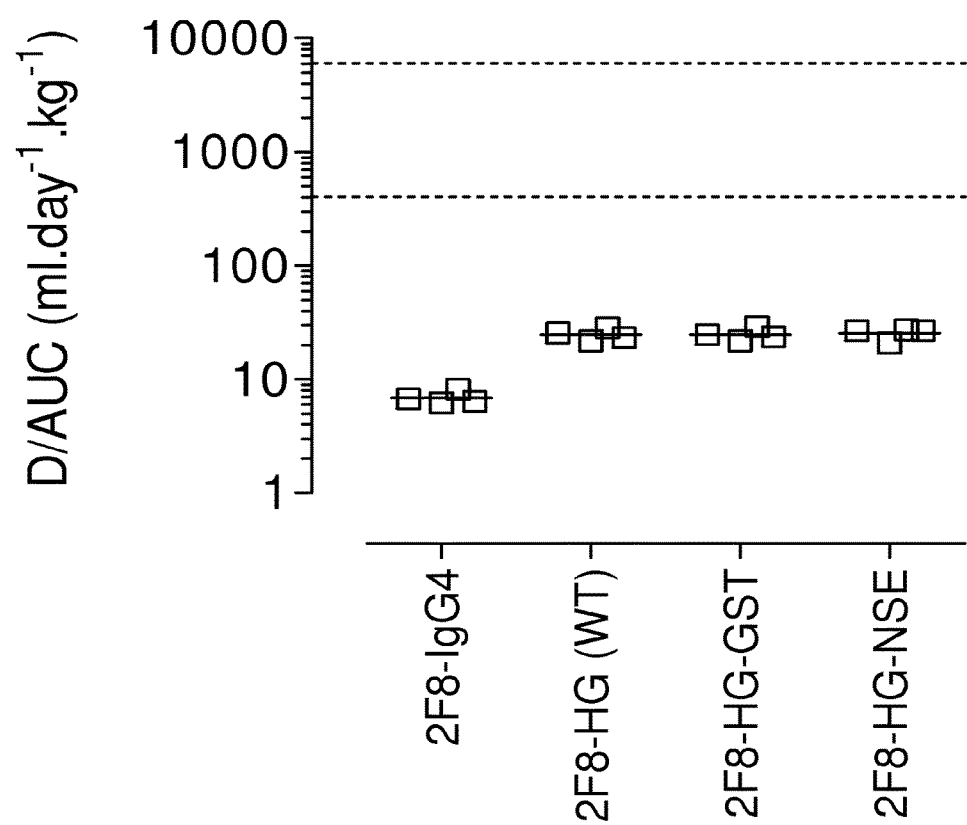
FIG. 11: Clearance (expressed as D/AUC) of non-glycosylation mutants 2F8-HG-GST and 2F8-HG-NSE compared to 2F8-HG (WT) and 2F8-IgG4.

FIG. 11 shows that absence of glycosylation of 2F8-HG did not affect plasma clearance.

Example 13

Figure 12:
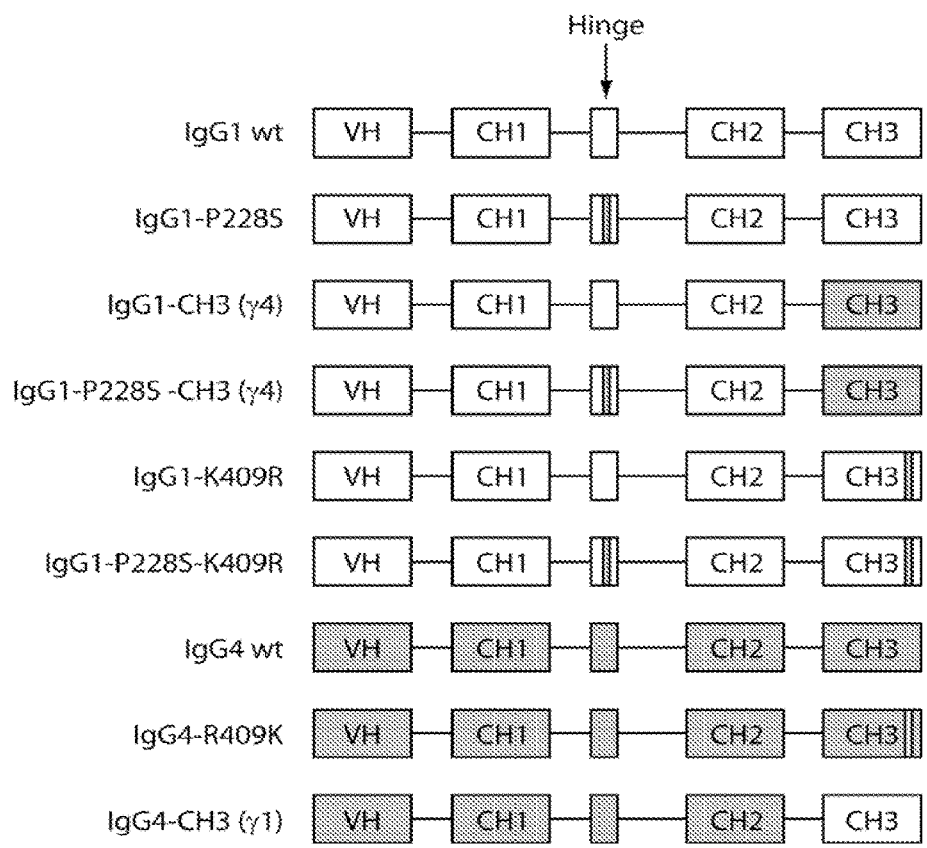
FIG. 12: Schematic representation of constructs for IgG1 and IgG4 containing mutations in the core hinge and/or CH3 domain (residues are numbered according to EU numbering, see table Example 16).

Generation of IgG1 and IgG4 Antibodies with Hinge Region and/or CH3 Domain Mutations To investigate the structural requirements for Fab arm exchange, five IgG1 mutants were made: an IgG1 with an IgG4 core-hinge (IgG1-P228S) (corresponds to 111 in SEQ ID NO:7), two CH3 domain swap mutants (IgG1-CH3(γ4) and IgG1-P228S-CH3(γ4)), one CH3 point mutant in which lysine present at position 409 of IgG1 (within the CH3 domain) (corresponds to 292 in SEQ ID NO:7) is replaced for arginine (IgG1-K409R), and one IgG1 with an IgG4 core hinge and K409R mutation (IgG1-P228S-K409R) (FIG. 12). These mutants were made with either Bet v 1 or Fel d 1 specificity. Please see WO 2008/119353 (Genmab A(S), especially the examples, for a further description of production of antibody mutants as well as the Bet v 1 and Fel d 1 specificities.

Two IgG4 mutants were made: one CH3 point mutant in which arginine present at position 409 of IgG4 (within the CH3 domain) (corresponds to 289 in SEQ ID NO:2) is replaced for lysine (IgG4-R409K), and one CH3 swap mutant (IgG4-CH3(γ1)) (FIG. 12). These mutants were also made with either Bet v 1 or Fel d 1 specificity.

Site directed mutagenesis was used to introduce a P228S mutation in the hinge of IgG1 using pEE-G1-wt a Bet v 1 as a template. Quickchange site-directed mutagenesis kit (Stratagene) was used to create the pEE-G1-CPSC mutant. The polymerase chain reaction (PCR) mix consisted of 5 μl pEE-G1 a Betv1 DNA template (~35 ng), 1.5 μl mutagenic primer-forward (~150 ng), 1.5 μl mutagenic primer-reverse (~150 ng), 1 μl dNTP mix, 5 μl reaction buffer (10×), 36 μl H$_2$O and finally 1 μl Pfu Turbo DNA polymerase. Then the mix was applied to the PCR: 30" 95° C., 30" 95° C. (denaturating), 1' 55° C. (annealing) and 17 minutes 68° C. (elongating). This cycle was repeated 20 times.

DNA digesting and ligation was used to create CH3 domain swap mutant constructs IgG1-CH3(γ4) and IgG1-P228S-CH3(γ4). Digestion reactions to obtain CH3 domains and vectors without CH3 domains were as follows: ~1500 ng DNA (pEE-G1-betv1, pEE-G1-CPSC and pEE-G4-betv1), 2 μl BSA, 2 μl Neb3 buffer, 1 μl SalI and H$_2$O added to a volume of 20 μl. Incubation at 37° C. for 30'. DNA was purified and eluted with 30 μl H$_2$O before 1 μl SanDI and 3 μl universal buffer was added and incubated at 37° C. for 30'. Fragments were subjected to gel electrophoresis on 1% agarose gels with ethidium bromide. Fragments were cut from the gel under ultraviolet light and dissolved using a DNA purification kit (Amersham). The pEE-G4-wt SalI/SanDI (which contained IgG4 CH3 domain) fragment was ligated into pEE-G1-wt and pEE-G1-CPSC using following procedure: 1 μl template DNA (SalI/SanDI digested pEE-G1-wt and pEE-G1-CPSC), 5 μl SalI/SanDI insert, 4 μl Ligate-it buffer, 9 μl H$_2$O and 1 μl ligase in a total volume of 20 μl. Ligation was stopped after 5'.

DNA digestion (using ApaI and HindIII) and ligation was used to replace the VH domain of the bet v 1 mutant antibodies with that of pEE-G4-a-feld1 wt, following a similar procedure as above.

Site-directed mutagenesis was used to introduce point mutations (K409R or R409K) into the pEE-γ4 wt, pEE-γ1 and PEE-γ1-P228S constructs. Site-directed mutagenesis was performed using the QuickChange II XL Site-Directed Mutagenesis Kit (Stratagene, Amsterdam, The Netherlands) according to the manufacturer's instructions, with changes as indicated below to increase mutagenic efficiency. This method included the introduction of a silent extra AccI site to screen for successful mutagenesis. First, a prePCR mix was used containing 3 μl 10×pfu reaction buffer, 1 μl dNTP mix (10 mM), 275 ng forward or reverse primer, 50 ng template DNA and 0.75 μl Pfu turbo hotstart polymerase. A prePCR was run using a GeneAmp PCR system 9700 (Applied Biosystems): initial denaturation at 94° C. for 5 min; 4 cycles of 94° C. for 30 sec, 50° C. for 1 min and 68° C. for 14 min. 25 μl of forward primer containing prePCR mix was added to 25 μl of reverse primer containing prePCR mix. 0.5 μl Pfu turbo hotstart was added and amplification was performed: denaturing at 94° C. for 1 min; 14 cycles of 94° C. for 1 min, 50° C. for 1 min and 68° C. for 8 min; 12 cycles of 94° C. for 30 sec, 55° C. for 1 min and 68° C. for 8 min.

PCR mixtures were stored at 4° C. until further processing. Next, PCR mixtures were incubated with 1 μl DpnI for 60 min at 37° C. and stored at 4° C. until further processing. 2 μl of the digested PCR products was transformed in One Shot DNH5α T1$^R$ competent E. coli cells (Invitrogen, Breda, The Netherlands) according to the manufacturer's instructions (Invitrogen). Next, cells were plated on Luria-Bertani (LB) agar plates containing 50 μg/ml ampicillin. Plates were incubated for 16-18 hours at 37° C. until bacterial colonies became evident. After screening by colony PCR and AccI digestion to check for successful mutagenesis, plasmid was isolated from the bacteria and the mutation was confirmed by DNA sequencing. To check if no unwanted extra mutations were introduced the whole HC coding region was sequenced and did not contain any additional mutations.

Recombinant antibodies from these constructs were transiently expressed in HEK 293 cells in 3 ml, 6-wells plates (NUNC) or in 125 or 250 erlenmeyers (Corning) with 293 Fectin (Invitrogen) as transfection reagent.

Example 14

Fab Arm Exchange of IgG1 and IgG4 Hinge Region or CH3 Domain Mutants

Antibodies were mixed and subsequently incubated with reduced glutathione (GSH) to investigate the exchange of half molecules. GSH (Sigma-Aldrich, St. Louis, Mo.) was dissolved in water before use.

The exchange of half molecules was evaluated by incubating an antibody mixture consisting of Bet v 1 specific antibody (200 ng) and Fel d 1 specific antibody (200 ng) in PBS/Azide containing GSH (1 or 10 mM) at 37° C. Total incubation volume was 50 µl. After 24 hours samples were drawn from the incubation mixture in PBS-AT (PBS supplemented with 0.3% bovine serum albumin, 0.1% Tween-20 and 0.05% (w/v) NaN$_3$). For samples containing 10 mM GSH an equimolar amount of iodine-acetamide, a strongly alkylating agent that inhibits the GSH activity, was added. Samples were stored at 4° C. for measuring of antigen binding and bispecific activity Levels of Bet v 1 binding antibodies were measured in the antigen binding test. Samples were incubated with 0.75 mg of protein G Sepharose (Amersham Biosciences, Uppsala, Sweden) in 750 µl PBS-IAT (PBS-AT supplemented with 1 µg/ml IVIg) in the presence of $^{125}$I-labeled Bet v 1 for 24 h. Next, the Sepharose was washed with PBS-T (PBS supplemented with 0.1% Tween-20 and 0.05% (w/v) NaN$_3$) and the amount of radioactivity bound relative to the amount of radioactivity added was measured. The concentration of Bet v 1 specific IgG was calculated using purified Bet v 1 specific antibodies as a standard (range 0-200 ng per test as determined by nephelometer).

The concentration of bispecific IgG (i.e. Fel d 1-Bet v 1 cross-linking activity) was measured in the heterologous cross-linking assay. In this assay, a sample was incubated for 24 h with 0.5 mg Sepharose-coupled cat extract, in which Fel d 1 antigen is present, in a total volume of 300 µl in PBS-IAT. Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured. The concentration of bispecific IgG (Fel d 1-Bet v 1) was calculated using the same calibration curve as used in the Bet v 1 binding test, which was obtained from purified Bet v 1 binding IgG. Tests were performed using antibody-containing supernatants in FreeStyle 293 expression medium, GIBCO/Invitrogen Corporation.

Figure 13:
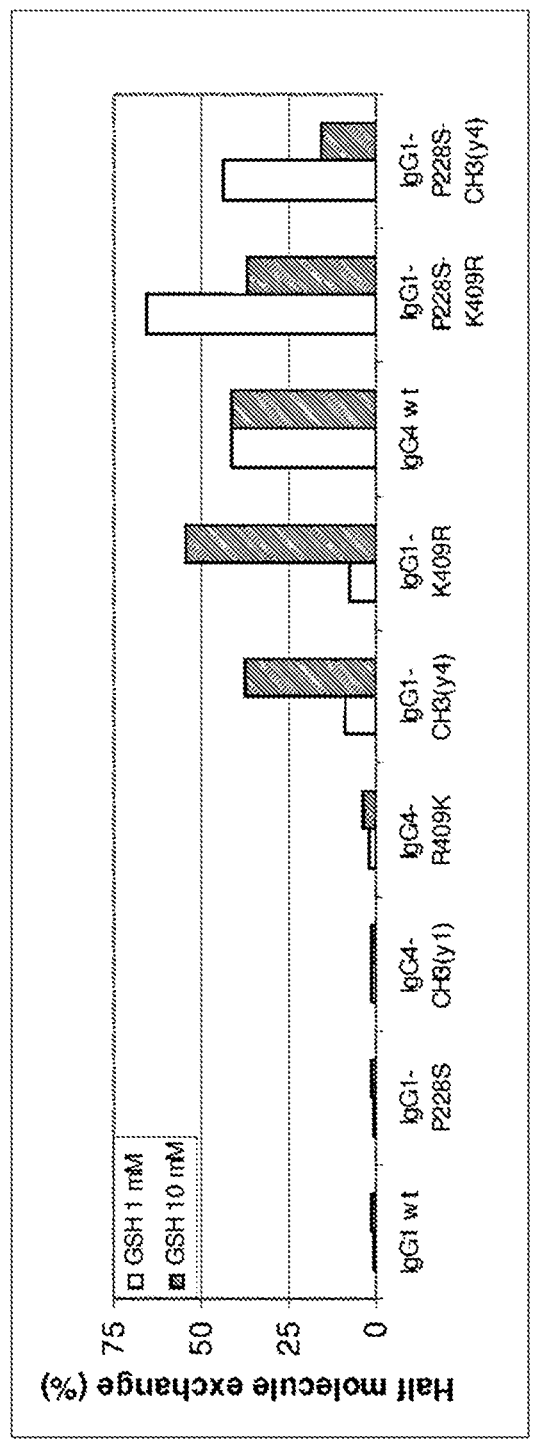
FIG. 13: Fab arm exchange of IgG1 and IgG4 hinge region or CH3 domain mutants (residues are numbered according to EU numbering, see table Example 16).

The following antibody mixtures were used:
Betv1-IgG1 wt with Feld1-IgG1 wt (indicated as IgG1 wt in FIG. 13)
Betv1-IgG1 P228S with Feld1-IgG1-P228S (IgG1-P228S in FIG. 13)
Betv1-IgG4-CH3(γ1) with Feld1-IgG4-CH3(γ1) (IgG4-CH3(γ1) in FIG. 13)
Betv1-IgG4-R409K with Feld1-IgG4-R409K (IgG4-R409K in FIG. 13)
Betv1-IgG1-CH3(γ4) with Feld1-IgG1-CH3(γ4) (IgG1-CH3(γ4) in FIG. 13)
Betv1-IgG1-K409R with Feld1-IgG1-K409R (IgG1-K409R in FIG. 13)
Betv1-IgG4 wt with Feld1-IgG4 wt (IgG4 wt in FIG. 13)
Betv1-IgG1-P228S-CH3(γ4) with Feld1-IgG1-P228S-CH3(γ4) (IgG1-P228S-CH3(γ4) in FIG. 13)
Betv1-IgG1-P228S-K409R with Feld1-IgG1-P228S-K409R (IgG1-P228S-K409R in FIG. 13)

The results (FIG. 13) showed that at 1 mM GSH, half molecule exchange occurs between IgG4 wt, IgG1-P228S-K409R or IgG1-P228S-CH3(γ4) antibodies. Under these conditions, IgG1 wt, IgG1-P228S, IgG4-CH3(γ1), IgG4-R409K, IgG1-CH3(γ4) or IgG1-K409R antibodies showed no or only minimal exchange of half molecules. At 10 mM GSH, half molecule exchange was also seen in the reactions containing IgG1-CH3(γ4) or IgG1-K409R antibodies.

Example 15

Additional CH3 Mutations to Stabilize Dimerization of Hingeless IgG4 Antibody Molecules in the Absence of IVIG Hingeless IgG4 antibody (HG) molecules form dimers by low affinity non-covalent interactions. WO/2007/059782 describes that this dimerization process can be inhibited by using HG IgG4 molecules in the presence of an excess of irrelevant antibodies. WO/2007/059782 describes a hingeless IgG4 anti-EGFR antibody 2F8-HG.

Construction of pHG-2F8: A vector for the expression of the heavy chain of 2F8-HG: The heavy chain cDNA encoding region of 2F8-HG was codon optimized and cloned in the pEE6.4 vector (Lonza Biologics, Slough, UK). The resulting vector was named pHG-2F8.

Construction of pKappa2F8: A vector for the production of the light chain of 2F8 antibodies: The VL region encoding antibody 2F8 was codon optimized and cloned in the pKappa2F2 vector (a vector encoding the codon optimized cDNA region of antibody 2F2 (described in WO2004035607) in vector pEE12.4 (Lonza)), replacing the 2F2 VL region with the 2F8 VL region. The resulting vector was named pKappa-2F8.

Hingeless IgG4 anti-EGFR antibody 2F8-HG has been described in WO/2007/059782. The additional mutations given in the Table below were introduced into the CH3 region of hingeless IgG4 antibody 2F8-HG by site-directed mutagenesis.

KABAT indicates amino acid numbering according to Kabat (Kabat et al., Sequences of Proteins of Immunological Interest, 5th Ed. Public Health Service, National Institutes of Health, Bethesda, Md. (1991).

EU index indicates amino acid numbering according to EU index as outlined in Kabat et al., Sequences of Proteins of Immunological Interest, 5th Ed. Public Health Service, National Institutes of Health, Bethesda, Md. (1991)). See also FIG. 14 for comparison of numbering methods.

| Numbering of CH3 mutations | | |
| --- | --- | --- |
| KABAT | EU index G4 | SEQ ID NO: 2 |
| 436 | F405A | F285A |
| 436 | F405L | F285L |
| 440 | R409A | R289A |
| 440 | R409K | R289K |

To make the constructs for the expression of the CH3 mutants, the mutations were introduced into pHG2F8 using site-directed mutagenesis.

The constructs were expressed transiently in HEK-293F cells by cotransfecting the heavy-chain- and light-chain-encoding plasmids and binding to purified EGFr was determined in the absence and presence of 200 µg/ml polyclonal human IgG (Intravenous Immunoglobulin, IVIG, Sanquin Netherlands).

Binding affinities were determined using an ELISA in which purified EGFr (Sigma, St Louis, Mo.) was coated to 96-well Microlon ELISA plates (Greiner, Germany), 50 ng/well. Plates were blocked with PBS supplemented with 0.05% Tween 20 and 2% chicken serum. Subsequently, samples, serially diluted in a buffer containing 100 µg/ml polyclonal human IgG (Intravenous Immunoglobulin, IVIG, Sanquin Netherlands) were added and incubated for 1 h at room temperature (RT). Plates were subsequently incubated with peroxidase-conjugated rabbit-anti-human kappa light chain (DAKO, Glostrup, Denmark) as detecting antibody and developed with 2,2'-azino-bis(3-ethylbenzthiazoline-6-sulfonic acid) (ABTS; Roche, Mannheim, Germany). Absorbance was measured in a microplate reader (Biotek, Winooski, Vt.) at 405 nm.

FIG. 14 shows that the binding curve of 2F8-HG in the presence of IVIG (thick dotted line with closed boxes) clearly right-shifts with respect to the binding curve of 2F8-HG without IVIG (thick closed line with open boxes). This difference in avidity for the EGFr coat is consistent with the idea that, in the presence of IVIG, 2F8-HG binds monovalently. The binding curves of the tested mutations, 2F8-HG-F405L, 2F8-HG-F405A, 2F8-HG-R409A and 2F8-HG-R409KA, become insensitive to the addition of IVIG and were super-imposable on the bivalent binding curve of 2F8-HG in the absence of IVIG. These differences in avidity for the EGFr coat are consistent with the idea that the 2F8-HG-F405L, 2F8-HG-F405A, 2F8-HG-R409A and 2F8-HG-R409K mutations stabilize dimerization of the HG molecules.

Example 16

Additional CH3 Domain Mutations to Stabilize Dimerization of Human IgG4 Antibodies Following the analysis described in Examples 1 and 2, it was hypothesized that in human IgG4, mutations relieving the electrostatic strain between R409 and K370 (indicated with # in the table below) could possibly be used to stabilize IgG4 and prevent Fab-arm exchange. Mutations were introduced into the CH3 domains of IgG4-CD20 and IgG4-EGFr by site-directed mutagenesis.

Mutations as given in the Table below were introduced into the CH3 domains of IgG4-CD20 and IgG4-EGFr by site-directed mutagenesis.

Figure 15:
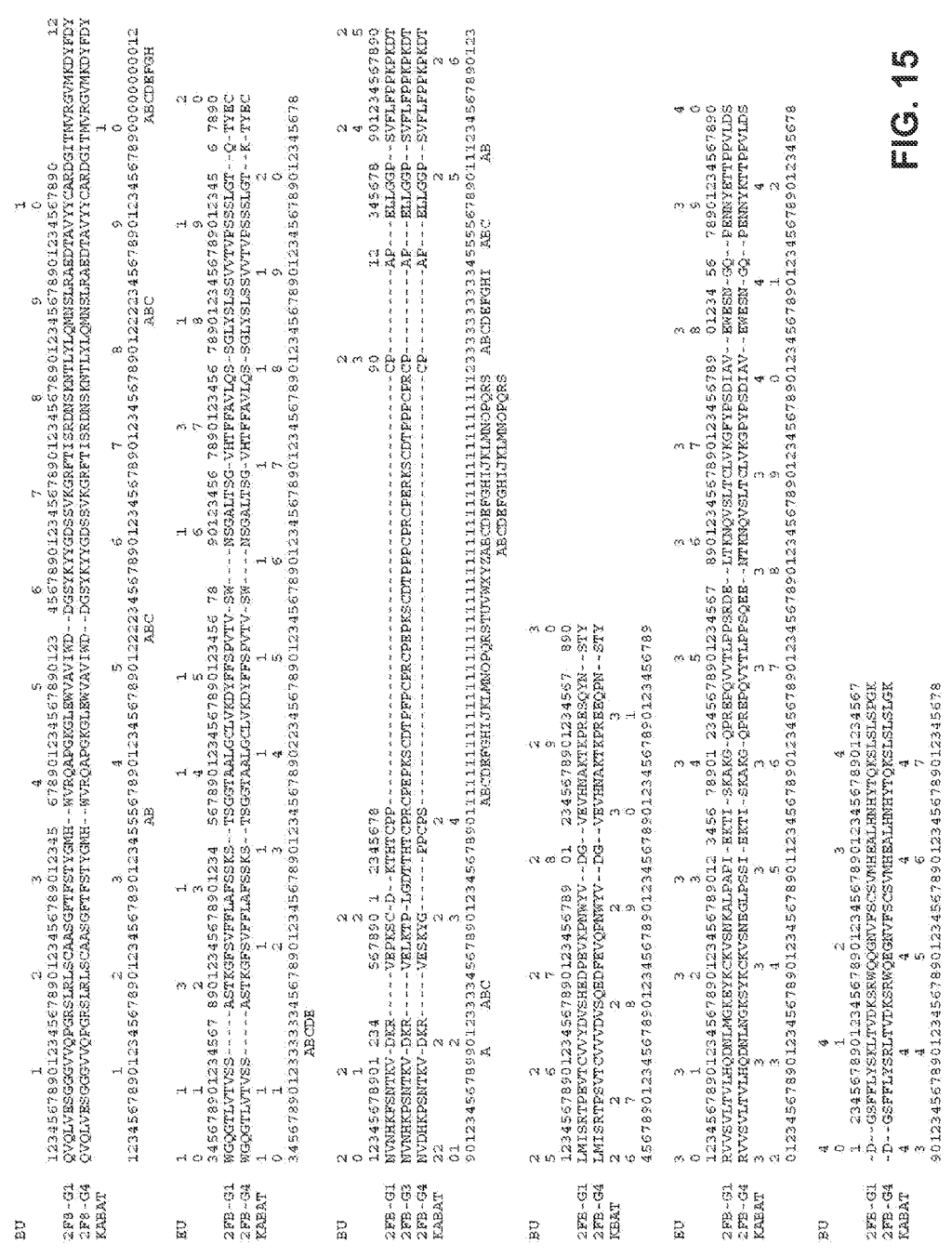

KABAT indicates amino acid numbering according to Kabat (Kabat et al., Sequences of Proteins of Immunological Interest, 5th Ed. Public Health Service, National Institutes of Health, Bethesda, Md. (1991). EU index indicates amino acid numbering according to EU index as outlined in Kabat et al., Sequences of Proteins of Immunological Interest, 5th Ed. Public Health Service, National Institutes of Health, Bethesda, Md. (1991)). See also FIG. 15 for comparison of numbering methods.

| Numbering of CH3 mutations | | |
|---|---|---|
| KABAT | EU index G4 | SEQ ID NO: 2 |
| 370 | Y349D | Y229D |
| 372 | L351K | L231K |
| 376 | Q355R | Q235R |
| 378 | E357T | E237T |
| 387 | S364D | S244D |
| 393 | K370E | K250E |
| 393 | K370Q | K250Q |
| 436 | F405A | F285A |
| 436 | F405L | F285L |
| 440 | R409A | R289A |
| 440 | R409K | R289K |
| 440 | R409L | R289L |
| 440 | R409M | R289M |
| 440 | R409T | R289T |
| 440 | R409W | R289W |
| 442 | T411V | T291V |
| 450 | E419Q | E299Q |
| 476 | L445P | L325P |

IgG1-CD20 and IgG1-EGFr, IgG4-CD20 and IgG4-EGFr, or IgG4-CH3mutant-CD20 and IgG4-CH3mutant-EGFr were mixed and incubated with 0.5 mM GSH as described above. Bispecific activity was determined as described in Example 33 of PCT application, WO 2008/119353 (Genmab A/S).

Figure 16:
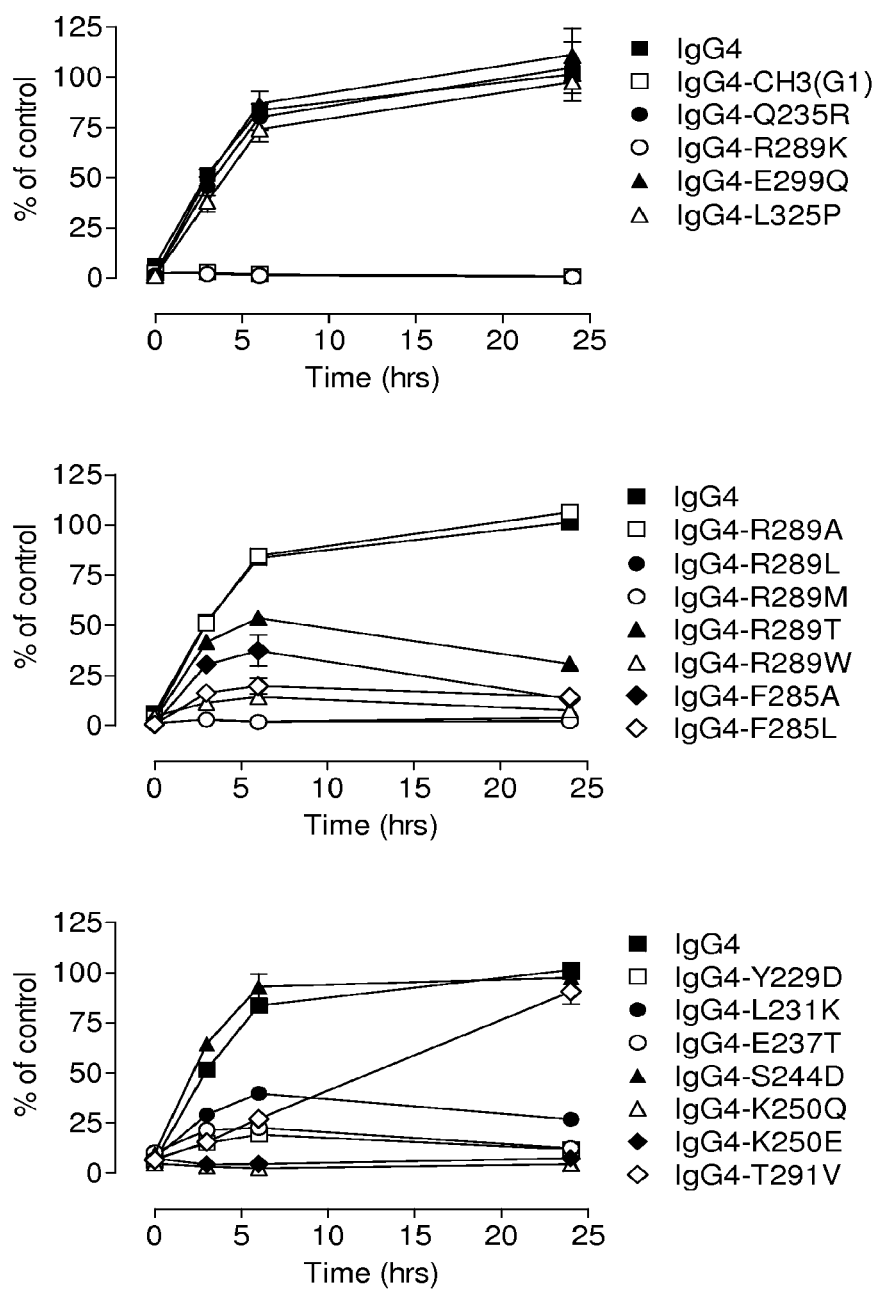
FIG. 16: Fab-arm exchange of CH3 domain mutants of human IgG4 antibodies. Mixtures of two recombinant human IgG4 antibodies (IgG4-CD20 and IgG4-EGFr) and CH3 domain mutants thereof were incubated with 0.5 mM GSH at 37° C. The formation of bispecific antibodies through Fab arm exchange was followed over time and measured in a sandwich ELISA. The bispecific activity of IgG4 at 24 hrs was set as 100%.

FIG. 16 shows that bispecific anti-EGFr/CD20 antibodies were formed in mixtures of IgG4 antibodies as well as in mixtures of CH3 domain mutants Q235R, E299Q, L325P, R289A and S244D. No bispecific activity was measured in mixtures of CH3 domain mutants R289K, R289M, R289L, K250E and K250Q, indicating that these mutations stabilized dimerization of human IgG4 antibodies. For CH3 domain mutants L231K, Y229D, F285A, F285L, R289W and E237T diminished bispecific activity was measured. The CH3 domain mutant T291V was unique in that it slowed down the exchange reaction, but reached the same level of exchange as wild-type IgG4 after 24 hrs.

Example 17

$K_D$ Measurements in CH2-CH3 Constructs Based on IgG4 and IgG4 CH3 Mutants

In order to investigate the CH3-CH3 interaction strength of IgG4, his-tagged constructs were designed based on the Fc-domains human IgG4 lacking the hinge region to prevent covalent inter-heavy chain disulfide bonds, his-CH2-CH3 (G4). Subsequently, variants of these constructs containing mutations in the CH3-CH3 interface listed below were generated by site-directed mutagenesis.

KABAT indicates amino acid numbering according to Kabat (Kabat et al., Sequences of Proteins of Immunological Interest, 5th Ed. Public Health Service, National Institutes of Health, Bethesda, Md. (1991). EU index indicates amino acid numbering according to EU index as outlined in Kabat et al., Sequences of Proteins of Immunological Interest, 5th Ed. Public Health Service, National Institutes of Health, Bethesda, Md. (1991)). See also FIG. 15 for comparison of numbering methods.

| Numbering of CH3 mutations | | |
|---|---|---|
| KABAT | EU index G4 | SEQ ID NO: 2 |
| 370 | Y349D | Y229D |
| 372 | L351K | L231K |

Numbering of CH3 mutations

| KABAT | EU index G4 | SEQ ID NO: 2 |
|---|---|---|
| 378 | E357T | E237T |
| 387 | S364D | S244D |
| 393 | K370E | K250E |
| 393 | K370Q | K250Q |
| 436 | F405A | F285A |
| 436 | F405L | F285L |
| 440 | R409A | R289A |
| 440 | R409K | R289K |
| 440 | R409L | R289L |
| 440 | R409M | R289M |
| 440 | R409W | R289W |

The monomer/dimer configuration of the his-CH2-CH3 (G4) and CH3 mutants was investigated at different concentrations, ranging from 0.01-10 µM using non-covalent nano-electrospray mass spectrometry as described in WO2007059782. For his-CH2-CH3(G4) and CH3 mutants signals corresponding to the monomeric ($M_s$) and dimeric ($D_s$) configurations were integrated and the relative proportion of each configuration at each concentration ($[M]_0$) was determined as described in example 8.

The $K_D$ measured for his-CH2-CH3(G4) (WT) was 4.8× $10^{-8}$ M. The relative $K_D$ of each mutant compared to the $K_D$ of his-CH2-CH3(G4) (WT) was calculated and plotted.

Figure 17:
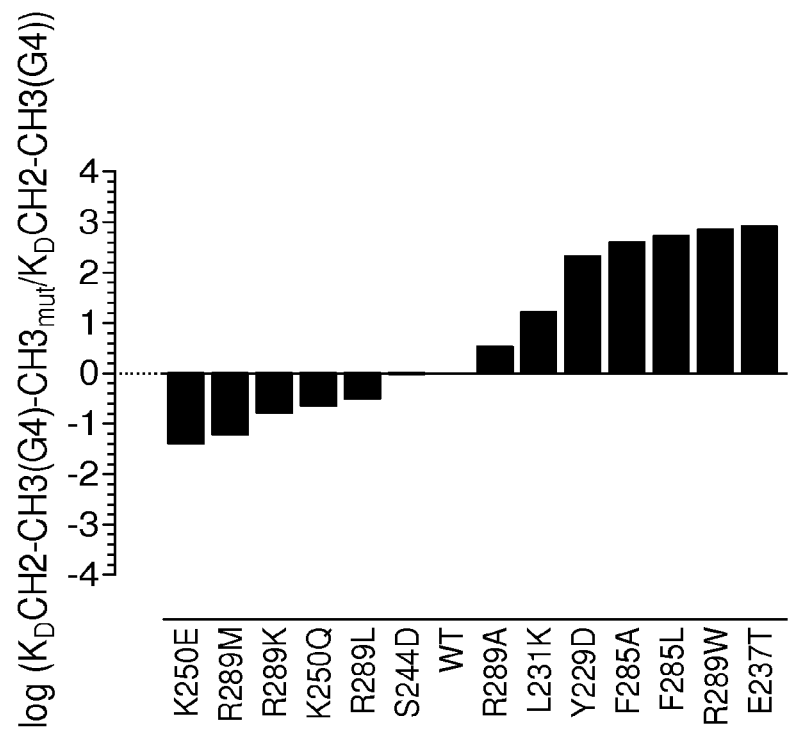
FIG. 17: Relative interaction strength ($K_D$) of CH3 mutants compared to his-CH2-CH3(G4) (WT).

FIG. 17 shows that CH3 mutants K250E, K250Q, R289L, R289M and R289K had a lower relative $K_D$, which translates into stabilization of the CH3-CH3 interaction compared to his-CH2-CH3(G4) (WT). The S244D mutant had a $K_D$ value, which was comparable to his-CH2-CH3(G4) (WT). The CH3 mutants Y229D, L231K, E237T, F285A, F285L, R289A and R289W showed a higher relative $K_D$, meaning an increase in monomeric behavior compared to his-CH2-CH3(G4) (WT).

Figure 18:
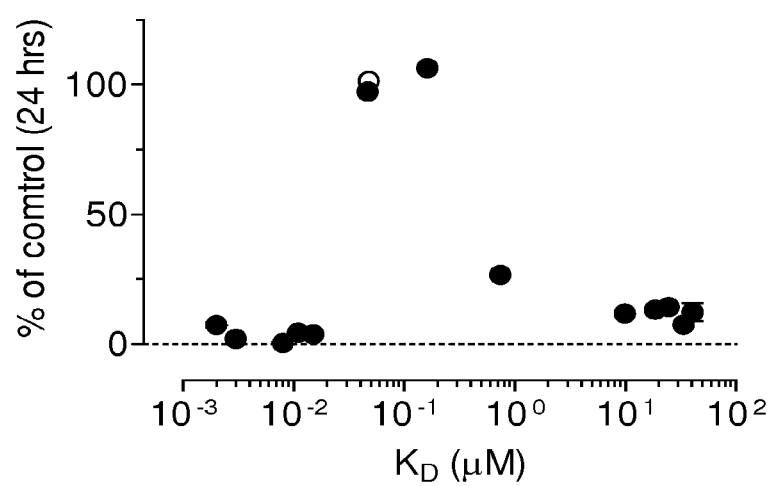
FIG. 18: Correlation between the CH3-CH3 interaction strength ($K_D$) and the bispecific activity. The bispecific activity of IgG4 at 24 hrs was set as 100% (open circle).

FIG. 18 shows the correlation between the $K_D$ values of the CH3 mutants in relation to the % of bispecific activity (after 24 hrs compared to WT IgG4). Mutants that are stabilized do not show bispecific activity, indicating that Fab-arm exchange does not occur in these mutants. Mutants that have $K_D$ values comparable to WT IgG4 behave similar in the generation of bispecific antibodies. FIG. 16 and FIG. 18 together show that mutants that have a weaker CH3-CH3 interaction do form bispecific antibodies, but the amount of bispecific antibodies is much lower and are not stable over time.

SEQUENCE LISTING

SEQ ID No: 1: The nucleic acid sequence of the wildtype $C_H$ region of human IgG4

```
   1 GCTAGCACCA AGGGCCCATC CGTCTTCCCC CTGGCGCCCT GCTCCAGGAG
  51 CACCTCCGAG AGCACAGCCG CCCTGGGCTG CCTGGTCAAG GACTACTTCC
 101 CCGAACCGGT GACGGTGTCG TGGAACTCAG GCGCCCTGAC CAGCGGCGTG
 151 CACACCTTCC CGGCTGTCCT ACAGTCCTCA GGACTCTACT CCCTCAGCAG
 201 CGTGGTGACC GTGCCCTCCA GCAGCTTGGG CACGAAGACC TACACCTGCA
 251 ACGTAGATCA CAAGCCCAGC AACACCAAGG TGGACAAGAG AGTTGGTGAG
 301 AGGCCAGCAC AGGGAGGGAG GGTGTCTGCT GGAAGCCAGG CTCAGCCCTC
 351 CTGCCTGGAC GCACCCCGGC TGTGCAGCCC CAGCCCAGGG CAGCAAGGCA
 401 TGCCCCATCT GTCTCCTCAC CCGGAGGCCT CTGACCACCC CACTCATGCT
 451 CAGGGAGAGG GTCTTCTGGA TTTTTCCACC AGGCTCCGGG CAGCCACAGG
 501 CTGGATGCCC CTACCCCAGG CCCTGCGCAT ACAGGGGCAG GTGCTGCGCT
 551 CAGACCTGCC AAGAGCCATA TCCGGGAGGA CCCTGCCCCT GACCTAAGCC
 601 CACCCCAAAG GCCAAACTCT CCACTCCCTC AGCTCAGACA CCTTCTCTCC
 651 TCCCAGATCT GAGTAACTCC CAATCTTCTC TCTGCAGAGT CCAAATATGG
 701 TCCCCCATGC CCATCATGCC CAGGTAAGCC AACCCAGGCC TCGCCCTCCA
 751 GCTCAAGGCG GGACAGGTGC CCTAGAGTAG CCTGCATCCA GGGACAGGCC
 801 CCAGCCGGGT GCTGACGCAT CCACCTCCAT CTCTTCCTCA GCACCTGAGT
 851 TCCTGGGGGG ACCATCAGTC TTCCTGTTCC CCCCAAAACC CAAGGACACT
 901 CTCATGATCT CCCGGACCCC TGAGGTCACG TGCGTGGTGG TGGACGTGAG
 951 CCAGGAAGAC CCCGAGGTCC AGTTCAACTG GTACGTGGAT GGCGTGGAGG
1001 TGCATAATGC CAAGACAAAG CCGCGGGAGG AGCAGTTCAA CAGCACGTAC
1051 CGTGTGGTCA GCGTCCTCAC CGTCCTGCAC CAGGACTGGC TGAACGGCAA
1101 GGAGTACAAG TGCAAGGTCT CCAACAAAGG CCTCCCGTCC TCCATCGAGA
1151 AAACCATCTC CAAAGCCAAA GGTGGGACCC ACGGGGTGCG AGGGCCACAT
```

```
1201 GGACAGAGGT CAGCTCGGCC CACCCTCTGC CCTGGGAGTG ACCGCTGTGC

1251 CAACCTCTGT CCCTACAGGG CAGCCCCGAG AGCCACAGGT GTACACCCTG

1301 CCCCCATCCC AGGAGGAGAT GACCAAGAAC CAGGTCAGCC TGACCTGCCT

1351 GGTCAAAGGC TTCTACCCCA GCGACATCGC CGTGGAGTGG GAGAGCAATG

1401 GGCAGCCGGA GAACAACTAC AAGACCACGC CTCCCGTGCT GGACTCCGAC

1451 GGCTCCTTCT TCCTCTACAG CAGGCTAACC GTGGACAAGA GCAGGTGGCA

1501 GGAGGGGAAT GTCTTCTCAT GCTCCGTGAT GCATGAGGCT CTGCACAACC

1551 ACTACACACA GAAGAGCCTC TCCCTGTCTC TGGGTAAA
```

SEQ ID No: 2: The amino acid sequence of the wildtype $C_H$ region of human IgG4

```
  1 ASTKGPSVFP LAPCSRSTSE STAALGCLVK DYFPEPVTVS WNSGALTSGV

51 HTFPAVLQSS GLYSLSSVVT VPSSSLGTKT YTCNVDHKPS NTKVDKRVES

101 KYGPPCPSCP APEFLGGPSV FLFPPKPKDT LMISRTPEVT CVVVDVSQED

151 PEVQFNWYVD GVEVHNAKTK PREEQFNSTY RVVSVLTVX1H QDWLNGKEYK

201 CKVSNKGLPS SIEKTISKAK GQPREPQVYT LPPSQEEMTK NQVSLTCLVK

251 GFYPSDIAVE WESNGQPENN YKTTPPVLDS DGSFFLYSX2L TVDKSRWQEG

301 NVFSCSVMHE ALHNHYTQKS LSLSLGK
``` wherein X1 at position 189 is Leu and X2 at position 289 is Arg, or
wherein X1 at position 189 is Leu and X2 at position 289 is Lys, or
wherein X1 at position 189 is Val and X2 at position 289 is Arg.

SEQ ID No: 3: The nucleic acid sequence encoding the $C_H$ region of human IgG4 (SEQ ID No: 1) mutated in positions 714 and 722

```
  1 GCTAGCACCA AGGGCCCATC CGTCTTCCCC CTGGCGCCCT GCTCCAGGAG

51 CACCTCCGAG AGCACAGCCG CCCTGGGCTG CCTGGTCAAG GACTACTTCC

101 CCGAACCGGT GACGGTGTCG TGGAACTCAG GCGCCCTGAC CAGCGGCGTG

151 CACACCTTCC CGGCTGTCCT ACAGTCCTCA GGACTCTACT CCCTCAGCAG

201 CGTGGTGACC GTGCCCTCCA GCAGCTTGGG CACGAAGACC TACACCTGCA

251 ACGTAGATCA CAAGCCCAGC AACACCAAGG TGGACAAGAG AGTTGGTGAG

301 AGGCCAGCAC AGGGAGGGAG GGTGTCTGCT GGAAGCCAGG CTCAGCCCTC

351 CTGCCTGGAC GCACCCCGGC TGTGCAGCCC CAGCCCAGGG CAGCAAGGCA

401 TGCCCCATCT GTCTCCTCAC CCGGAGGCCT CTGACCACCC CACTCATGCT

451 CAGGGAGAGG GTCTTCTGGA TTTTTCCACC AGGCTCCGGG CAGCCACAGG

501 CTGGATGCCC CTACCCCAGG CCCTGCGCAT ACAGGGGCAG GTGCTGCGCT

551 CAGACCTGCC AAGAGCCATA TCCGGGAGGA CCCTGCCCCT GACCTAAGCC

601 CACCCCAAAG GCCAAACTCT CCACTCCCTC AGCTCAGACA CCTTCTCTCC

651 TCCCAGATCT GAGTAACTCC CAATCTTCTC TCTGCAGAGT CCAAATATGG
```

-continued

```
 701 TCCCCCATGC CCACCATGCC CGGGTAAGCC AACCCAGGCC TCGCCCTCCA
 751 GCTCAAGGCG GGACAGGTGC CCTAGAGTAG CCTGCATCCA GGGACAGGCC
 801 CCAGCCGGGT GCTGACGCAT CCACCTCCAT CTCTTCCTCA GCACCTGAGT
 851 TCCTGGGGGG ACCATCAGTC TTCCTGTTCC CCCCAAAACC CAAGGACACT
 901 CTCATGATCT CCCGGACCCC TGAGGTCACG TGCGTGGTGG TGGACGTGAG
 951 CCAGGAAGAC CCCGAGGTCC AGTTCAACTG GTACGTGGAT GGCGTGGAGG
1001 TGCATAATGC CAAGACAAAG CCGCGGGAGG AGCAGTTCAA CAGCACGTAC
1051 CGTGTGGTCA GCGTCCTCAC CGTCCTGCAC CAGGACTGGC TGAACGGCAA
1101 GGAGTACAAG TGCAAGGTCT CCAACAAAGG CCTCCCGTCC TCCATCGAGA
1151 AAACCATCTC CAAAGCCAAA GGTGGGACCC ACGGGGTGCG AGGGCCACAT
1201 GGACAGAGGT CAGCTCGGCC CACCCTCTGC CCTGGGAGTG ACCGCTGTGC
1251 CAACCTCTGT CCCTACAGGG CAGCCCCGAG AGCCACAGGT GTACACCCTG
1301 CCCCCATCCC AGGAGGAGAT GACCAAGAAC CAGGTCAGCC TGACCTGCCT
1351 GGTCAAAGGC TTCTACCCCA GCGACATCGC CGTGGAGTGG GAGAGCAATG
1401 GGCAGCCGGA GAACAACTAC AAGACCACGC CTCCCGTGCT GGACTCCGAC
1451 GGCTCCTTCT TCCTCTACAG CAGGCTAACC GTGGACAAGA GCAGGTGGCA
1501 GGAGGGGAAT GTCTTCTCAT GCTCCGTGAT GCATGAGGCT CTGCACAACC
1551 ACTACACACA GAAGAGCCTC TCCCTGTCTC TGGGTAAA
```

SEQ ID No: 4: The amino acid sequence of the hingeless $C_H$ region of a human IgG4.

```
  1 ASTKGPSVFP LAPCSRSTSE STAALGCLVK DYFPEPVTVS WNSGALTSGV
 51 HTFPAVLQSS GLYSLSSVVT VPSSSLGTKT YTCNVDHKPS NTKVDKRVAP
101 EFLGGPSVFL FPPKPKDTLM ISRTPEVTCV VVDVSQEDPE VQFNWYVDGV
151 EVHNAKTKPR EEQFNSTYRV VSVLTVLHQD WLNGKEYKCK VSNKGLPSSI
201 EKTISKAKGQ PREPQVYTLP PSQEEMTKNQ VSLTCLVKGF YPSDIAVEWE
251 SNGQPENNYK TTPPVLDSDG SFFLYSRLTV DKSRWQEGNV FSCSVMHEAL
301 HNHYTQKSLS LSLGK
```

SEQ ID NO: 5: The amino acid sequence of the lambda chain constant human (accession number S25751)

```
  1 qpkaapsvtl fppsseelqa nkativclis dfypgavtva wkadsspvka
 51 gvetttpskq snnkyaassy lsltpeqwks hrsyscqvth egstvektva
101 pteCs
```

SEQ ID NO: 6: The amino acid sequence of the kappa chain constant human (accession number P01834)

```
  1 tvaapsvfif ppsdeqlksg tasvvcllnn fypreakvqw kvdnalqsgn
 51 sqesvteqds kdstyslsst ltlskadyek hkvyacevth qglsspvtks
101 fnrgeC
```

SEQ ID NO: 7: The amino acid sequence of IgG1 constant region (accession number P01857)

```
  1 astkgpsvfp lapSskstsg gtaalgclvk dyfpepvtvs wnsgaltsgv
 51 htfpavlqss glyslssvvt vpssslgtqt yicnvnhkps ntkvdkkvep
101 kscdkthtcp pcpapellgg psvflfppkp kdtlmisrtp evtcvvvdvs
151 hedpevkfnw yvdgvevhna ktkpreeqyn styrvvsvlt vlhqdwlngk
201 eykckvsnka lpapiektis kakgqprepq vytlppsRDe mtknqvsltc
251 lvkgfypsdi avewesngqp ennyktttppv ldsdgsffly sKltvdksrw
301 qQgnvfscsv mhealhnhyt qkslslsPgk
```

SEQ ID NO: 8: The amino acid sequence of the IgG2 constant region (accession number P01859)

```
  1 astkgpsvfp lapcsrstse staalgclvk dyfpepvtvs wnsgaltsgv
 51 htfpavlqss glyslssvvt vpssnfgtqt ytcnvdhkps ntkvdktver
101 kccvecppcp appvagpsvf lfppkpdtl misrtpevtc vvvdvshedp
151 evqfnwyvdg vevhnaktkp reeqfnstfr vvsvltvvhq dwlngkeykc
201 kvsnkglpap iektisktkg qprepqvytl ppsReemtkn qvsltclvkg
251 fypsdiavew esngqpenny kttppMldsd gsfflysKlt vdksrwqQgn
301 vfscsvmhea lhnhytqksl slsPgk
```

SEQ ID NO: 9: The amino acid sequence of the IgG3 constant region (accession number A23511)

```
  1 astkgpsvfp lapcsrstsg gtaalgclvk dyfpepvtvs wnsgaltsgv
 51 htfpavlqss glyslssvvt vpssslgtqt ytcnvnhkps ntkvdkrvel
101 ktplgdttht cprcpepkse dtppcprcp epksedtppp cprcpepkse
151 dtpppcprcp apellggpsv flfppkpkdt lmisrtpevt cvvvdvshed
201 pevqfkwyvd gvevhnaktk preeqynstf rvvsvltvlh qdwlngkeyk
251 ckvsnkalpa piektisktk gqprepqvyt lppsReemtk nqvsltclvk
301 gfypsdiave wesSgqpenn yNttppMlds dgsfflysKl tvdksrwqQg
351 nIfscsvmhe alhnRFtqks lslsPgk
```

The invention claimed is:

1. A monovalent antibody comprising a single heavy chain and a single light chain, wherein the antibody is a human IgG4 isotype comprising a modified heavy chain constant region,
wherein the heavy chain constant region has been modified relative to the sequence set forth in SEQ ID NO: 4 by one or more of the following amino acid substitutions: Glu (E) in position 225 has been replaced by Ala (A) or Val (V); Ser (S) in position 232 has been replaced by Arg (R); Leu (L) in position 236 has been replaced by Glu (E), Gly (G), Ser (S), or Thr (T); Asp (D) in position 267 has been replaced by Ala (A) or Ser (S); Phe (F) in position 273 has been replaced by Asp (D), Thr (T), Arg (R), Gln (Q), or Tyr (Y); or Tyr (Y) in position 275 has been replaced by Glu (E), Gln (Q), or Lys (K); and
wherein the heavy chain constant region further comprises a hinge region modified such that all amino acid residues in the hinge region which are capable of forming a disulfide bond with an identical constant region in the presence of polyclonal human IgG have been deleted or substituted with other amino acid residues, including modification of all cysteine residues in the hinge region.

2. The monovalent antibody of claim 1, wherein all the listed amino acid substitutions relative, to the sequence set forth in SEQ ID NO: 4 are present.

3. The monovalent antibody of claim 1, wherein the heavy chain constant region has been modified relative to the sequence set forth in SEQ ID NO:4 by the following amino acid substitutions: Phe (F) in position 273 has been replaced by Asp (D) or Thr (T), and Tyr (Y) in position 275 has been replaced by Glu (E).

4. The monovalent antibody of claim 1, wherein the monovalent antibody is a human antibody.

5. The monovalent antibody of claim 1, wherein the heavy chain constant region has been modified such that all cysteine residues in the hinge region have been substituted with amino acid residues that have an uncharged polar side chain or a nonpolar side chain.

6. The monovalent antibody of claim 1, wherein the monovalent antibody binds to a target selected from erythropoietin, beta-amyloid, thrombopoietin, interferon-alpha (2a and 2b), -beta (1b), -gamma, TNFR I (CD120a), TNFR II (CD120b), IL-1R type 1(CD121a), IL-1R type 2(CD121b), IL-2, IL2R (CD25), IL-2R-beta (CD123), IL-3, IL-4, IL-3R (CD123), IL-4R (CD124), cMet, CD20, CD38, IL-8, CD25, CD74, FcalphaRl, FcepsilonRl, acetyl choline receptor, fas, fast, TRAIL, hepatitis virus, hepatitis C virus, envelope E2 of hepatitis C virus, tissue factor, a complex of tissue factor and Factor VII, EGFr, CD4, CD28, IL-5R (CD125), IL-6R-alpha (CD126), -beta (CD130), IL-10, IL-11, IL-15BP, IL-15R, IL-20, IL-21, TCR variable chain, RANK, RANK-L, CTLA4, CXCR4R, CCR5R, TGF-betal TGF-beta2, TGF-beta3, G-CSF, GM-CSF, MIF-R (CD74), M-CSF-R (CD115), GM-CSFR (CD116), soluble FcRI, sFcRII, sFcRIII, FcRn, Factor VII , Factor VIII, Factor IX, VEGF, anti-psychotic drug, anti-depressant drug, anti-Parkinson drug, anti-seizure agent, neuromuscular blocking drug, anti-epileptic drug, adrenocorticosteroid, insulin, incretins (GIP and GLP-1), Exenatide, sitagliptin, thyroid hormone, growth hormone, ACTH, oestrogen, testosterone, anti-diuretic hormone, diuretic, heparin, EPO, beta-blocking agent, cytotoxic agent, anti-viral drug, anti-bacterial agent, anti-fungal drug, anti-parasitic drug, anti-coagulation drug, anti-inflammatory drug, anti-asthma drug, anti-COPD drug, opiate, morphine, vitamin, LH, and FSH.

7. The monovalent antibody of claim 1, which is conjugated to a therapeutic moiety, an immunosuppressant or a radioisotope.

8. The monovalent antibody of claim 1, wherein the heavy chain constant region has been modified relative to the sequence set forth in SEQ ID NO: 4 such that Phe (F) in position 273 has been replaced by Asp (D).

9. The monovalent antibody of claim 1, wherein the heavy chain constant region has been modified relative to the sequence set forth in SEQ ID NO: 4 such that Phe (F) in position 273 has been replaced by Thr (T).

10. The monovalent antibody of claim 1, wherein the heavy chain constant region has been modified relative to the sequence set forth in SEQ ID NO: 4 such that Tyr (Y) in position 275 has been replaced by Glu (E).

11. The monovalent antibody of claim 1, wherein the heavy chain constant region has been modified relative to the sequence set forth in SEQ ID NO: 4 by the following amino acid substitutions: Asp (D) in position 267 has been replaced by Ser (S), and Tyr (Y) in position 275 has been replaced by Glu (E), Gln (Q), or Lys (K).

12. The monovalent antibody of claim 1, wherein the heavy chain constant region has been modified relative to the sequence set forth in SEQ ID NO: 4 such that Asp (D) in position 267 has been replaced by Ser (S).

13. The monovalent antibody of claim 1, wherein the heavy chain constant region has been modified relative to the sequence set forth in SEQ ID NO: 4 such that Tyr (Y) in position 275 has been replaced by Glu (E).

14. The monovalent antibody of claim 1, wherein the heavy chain constant region has been modified relative to the sequence set forth in SEQ ID NO: 4 such that Tyr (Y) in position 275 has been replaced by Gln (Q).

15. The monovalent antibody of claim 1, wherein the heavy chain constant region has been modified relative to the sequence set forth in SEQ ID NO: 4 such that Tyr (Y) in position 275 has been replaced by Lys (K).

16. A pharmaceutical composition comprising the monovalent antibody of claim 1 and one or more pharmaceutically acceptable excipients, diluents, and/or carriers.

17. The pharmaceutical composition of claim 16, wherein the composition further comprises one or more additional therapeutic agents.

* * * * *

UNITED STATES PATENT AND TRADEMARK OFFICE
CERTIFICATE OF CORRECTION

PATENT NO. : 10,000,570 B2
APPLICATION NO. : 14/739768
DATED : June 19, 2018
INVENTOR(S) : Aran Frank Labrijn et al.

It is certified that error appears in the above-identified patent and that said Letters Patent is hereby corrected as shown below:

In Claim 6, Column 71, Line 64, "FcalphaRl, FcepsilonRl," should read --FcalphaRI, FcepsilonRI,--.

In Claim 6, Column 71, Line 65, "fast," should read --fasl,--.

In Claim 6, Column 72, Line 18, "TGF-betal" should read --TGF-beta1,--.

Signed and Sealed this
Eighteenth Day of September, 2018

Andrei Iancu
*Director of the United States Patent and Trademark Office*